United States Patent
Asefa et al.

(10) Patent No.: US 9,283,545 B2
(45) Date of Patent: Mar. 15, 2016

(54) EFFICIENT AND RECYCLABLE HETEROGENEOUS NANOCATALYSTS

(75) Inventors: Tewodros Asefa, Somerset, NJ (US); Ankush V. Biradar, Pune (IN); Yanfei Wang, Beijing (CN)

(73) Assignee: Rutgers, The State University of New Jersey, New Brunswick, NJ (US)

(*) Notice: Subject to any disclaimer, the term of this patent is extended or adjusted under 35 U.S.C. 154(b) by 270 days.

(21) Appl. No.: 13/396,052

(22) Filed: Feb. 14, 2012

(65) Prior Publication Data

US 2012/0296124 A1  Nov. 22, 2012

Related U.S. Application Data

(60) Provisional application No. 61/447,913, filed on Mar. 1, 2011, provisional application No. 61/442,498, filed on Feb. 14, 2011.

(51) Int. Cl.

| | |
|---|---|
| B01J 21/08 | (2006.01) |
| C07C 45/64 | (2006.01) |
| C07C 45/58 | (2006.01) |
| C07C 209/36 | (2006.01) |
| B01J 31/06 | (2006.01) |
| B01J 31/28 | (2006.01) |
| B01J 23/44 | (2006.01) |
| C07C 5/11 | (2006.01) |
| C07C 5/03 | (2006.01) |
| C07C 29/145 | (2006.01) |
| B01J 31/26 | (2006.01) |
| C07C 29/132 | (2006.01) |
| C07C 5/08 | (2006.01) |
| B82Y 30/00 | (2011.01) |
| B82Y 40/00 | (2011.01) |
| B01J 21/06 | (2006.01) |
| B01J 23/06 | (2006.01) |
| B01J 23/24 | (2006.01) |
| B01J 23/32 | (2006.01) |
| B01J 23/72 | (2006.01) |
| B01J 23/74 | (2006.01) |
| B01J 33/00 | (2006.01) |
| B01J 35/00 | (2006.01) |
| B01J 35/08 | (2006.01) |
| B01J 37/00 | (2006.01) |
| B01J 37/02 | (2006.01) |
| B01J 35/10 | (2006.01) |

(52) U.S. Cl.
CPC .......... *B01J 21/08* (2013.01); *B01J 21/066* (2013.01); *B01J 23/06* (2013.01); *B01J 23/24* (2013.01); *B01J 23/32* (2013.01); *B01J 23/44* (2013.01); *B01J 23/72* (2013.01); *B01J 23/74* (2013.01); *B01J 33/00* (2013.01); *B01J 35/002* (2013.01); *B01J 35/006* (2013.01); *B01J 35/0013* (2013.01); *B01J 35/0086* (2013.01); *B01J 35/08* (2013.01); *B01J 35/1014* (2013.01); *B01J 35/1019* (2013.01); *B01J 35/1038* (2013.01); *B01J 37/0018* (2013.01); *B01J 37/0203* (2013.01); *B01J 37/0209* (2013.01); *B01J 37/0217* (2013.01); *B01J 37/0221* (2013.01); *B82Y 30/00* (2013.01); *B82Y 40/00* (2013.01); *C07C 5/03* (2013.01); *C07C 5/08* (2013.01); *C07C 29/132* (2013.01); *C07C 29/145* (2013.01); *C07C 45/64* (2013.01); *C07C 209/365* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 2010/0093013 A1 | 4/2010 | Asefa et al. | |
| 2010/0313937 A1 | 12/2010 | Asefa et al. | |
| 2011/0196164 A1 | 8/2011 | Asefa et al. | |
| 2011/0311635 A1* | 12/2011 | Stucky et al. | ................. 424/490 |

OTHER PUBLICATIONS

Wang, Y., et al. "Assembling Nanostructures for Effective Catalysis: Supported Pd Nanoparticles Multicores Coated by Hollow and Nanoporous ZrO2 Shell." ChemSusChem. 2012; 5:132-139.

Biradar, A., et al. "Continuous Henry Reaction to a Specific Product over Nanoporous Silica-Supported Amine Catalysts on Fixed Bed Reactor." Applied Catalysis A: General. 2010; 389:19-26.

Wang, Y., et al. "Silica nanosphere-Supported Shaped Pd Nanoparticles Encapsulated with Nanoporous Silica Shell: Efficient and Recyclable Nanocrystals." J. Mater. Chem. 2010; 20:7834-7841.

Biradar, A.V., et al. "Silica-Dendrimer Core—Shell Microspheres with Encapsulated Ultrasmall Palladium Nanoparticles: Efficient and Easily Recyclable Heterogenous Nanocrystals." Langmuir. 2011; 27:14408-14418.

Lee, J., et al. "Precise Tuning of Porosity and Surface Functionality in Au@SiO2 Nanoreactors for High Catalytic Efficiency," Chem. Mater. 2008, 20:5839-5844.

Knecht, M.R., et al. "Dendrimer-Mediated Formation of Multicomponent Nanospheres" Chem. Mater. 2004, 16:4890-4895.

Hagiwara, H., et al. "Immobilization of Pd on Nanosilica Dendrimer as SILC: Highly Active and Sustainable Cluster Catalyst for Suzuki-Miyaura Reaction" Synlett 2010 13:1990-1996.

Arnal, P.M., et al. "High-Temperature-Stable Catalysts by Hollow Sphere Encapsulation" Angew. Chem. 2006, 118:8404-8407.

(Continued)

*Primary Examiner* — Rebecca Anderson
*Assistant Examiner* — Po-Chih Chen
(74) *Attorney, Agent, or Firm* — Robert C. Netter, Jr.; Dann, Dorfman, Herrell & Skillman

(57) ABSTRACT

Efficient and recyclable heterogeneous nanocatalysts and methods of synthesizing and using the same are provided.

25 Claims, 53 Drawing Sheets

(56) References Cited

OTHER PUBLICATIONS

Figure 1:
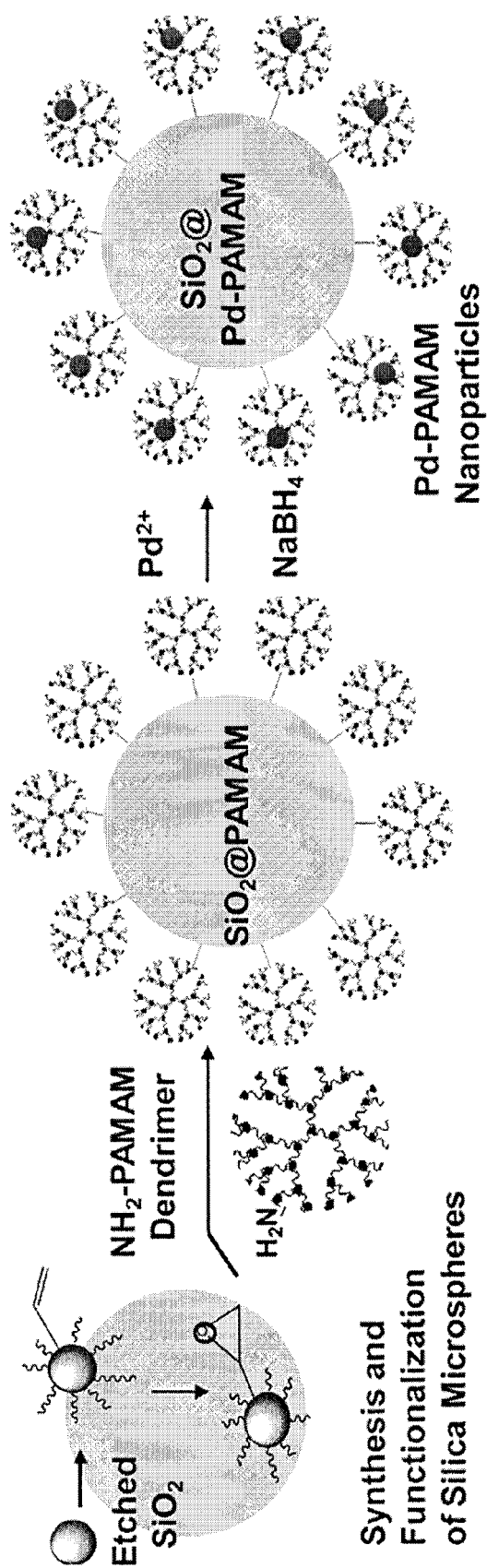

Asefa, T., et al. "Corrugated and Nanoporous Silica Microspheres: Synthesis by Controlled Etching, and Improving Their Chemical Adsorption and Application in Biosensing" J. Mater. Chem. 2008, 18:5604-5614.

Huang, X., et al. "An Assembly Route to Inorganic Catalytic Nanoreactors Containing Sub-10-nm Gold Nanoparticles with Anti-Aggregation Properties" Small 2009, 5(3):361-365.

Joo, S.H., et al. "Thermally Stable Pt/mesoporous Silica Core—Shell Nanocatalysts for High-Temperature Reactions" Nature Materials 2009, 8:126-131.

Park, J.N., et al. "Highly Active and Sinter-Resistant Pd-Nanoparticle Catalysts Encapsulated in Silica" Small 2008 4 (10):1694-1697.

Jiang, Y., et al. "Heterogeneous Hydrogenation Catalyses over Recyclable Pd(0) Nanoparticle Catalysts Stabilized by PAMAM-SBA-15 Organic-Inorganic Hybrid Composites" J. Am. Chem. Soc. 2006, 128:716-717.

\* cited by examiner

US 9,283,545 B2

EFFICIENT AND RECYCLABLE HETEROGENEOUS NANOCATALYSTS

This application claims priority under 35 U.S.C. §119(e) to U.S. Provisional Patent Application No. 61/447,913, filed on Mar. 1, 2011 and U.S. Provisional Patent Application No. 61/442,498, filed on Feb. 14, 2011. The foregoing applications are incorporated by reference herein.

This invention was made with government support under Grant Nos: CAREER NSF CHE-1004218 and NSF DMR-0968937 awarded by the National Science Foundation (NSF). The government has certain rights in the invention.

FIELD OF THE INVENTION

The present invention relates to the field of catalysts. Specifically, efficient and recyclable nanocatalysts, methods of synthesis, and methods of use thereof are disclosed.

BACKGROUND OF THE INVENTION

Several publications and patent documents are cited throughout the specification in order to describe the state of the art to which this invention pertains. Each of these citations is incorporated herein by reference as though set forth in full.

The use of metal nanoparticles (MNPs) in catalysis has rapidly increased in recent years because of their efficient and intrinsic size-dependent catalytic properties as well as their ability to catalyze a range of chemical reactions (Nishihata et al. (2002) Nature 418:164-167; Astruc et al. (2005) Angew. Chem., Int. Ed., 44:7852-7872; Moreno-Manas et al. (2003) Acc. Chem. Res., 36:638-643; Li et al. (2002) Langmuir 18:4921-4925; Ranu et al. (2009) Pure Appl. Chem., 81:2337-2354; Barbaro et al. (2010) Dalton Trans., 39:8391-8402; Migowski et al. (2006) Chem. Eur. J., 1:32-39; Durand et al. (2008) Eur. J. Inorg. Chem., 23:3577-3586). For many MNPs to catalyze reactions or result in efficient catalysis, the reacting substrates must directly interact with the metal surfaces. This metal-substrate interaction would be greater if the MNPs were synthesized "naked". Unfortunately, however, atoms of "naked" MNPs have a greater tendency to aggregate into a bulk material due to their high surface energies, which results in loss of, or decrease in, their intrinsic catalytic activity and selectivity over time (Moulijn, et al. (2001) Appl. Catal. A: Gen., 212:3-16; Xing et al. (2007) Chem. Mater., 19:4820-4826). In particular, Pd nanoparticles (PdNPs), which are well known for their catalytic activities, can easily aggregate to form Pd-black because of the very high surface energy of palladium (Iwasawa et al. (2004) J. Am. Chem. Soc., 126:6554-6555). Although the degree of aggregation of PdNP or other MNP catalysts can be overcome or minimized by passivating the metals' surfaces with organic ligands, this too will, unfortunately, be accompanied by the loss of catalytic activity because the very sites on the metals where catalysis takes place will be covered by these surface passivating organic groups (Jayamurugan et al. (2009) J. Mol. Catal. A: Chem., 307:142-148). Accordingly, there is a strong need for efficient and recyclable nanocatalysts.

SUMMARY OF THE INVENTION

In accordance with the present invention, efficient and recyclable catalytic-active nanoparticles are provided. In a particular embodiment, the catalytic nanoparticle comprises a silica nanoparticle core covalently attached to at least one dendrimer encompassing at least one catalyst. In a particular embodiment, the silica core is etched (e.g., with a base such as KOH or NaOH). The dendrimer may be covalently attached to the silica core directly or via a linker. In a particular embodiment, the dendrimer is an amine-terminated poly(amido amine) (PAMAM) dendrimer. The catalyst may be a metal catalyst such as Pd nanoparticles. Methods of synthesizing these catalytic nanoparticles are also provided. In a particular embodiment, the method comprises etching a silica nanoparticle, covalently attaching at least one dendrimer to the etched silica microsphere, and entrapping at least one catalyst in the dendrimer.

In accordance with another aspect of the instant invention, the catalytic nanoparticles comprise a silica nanoparticle coated with at least one catalyst and an etched silica outer layer. In a particular embodiment, the catalyst is a metal catalyst such as palladium nanoparticles. Methods of synthesizing these catalytic nanoparticles are also provided. In a particular embodiment, the method comprises coating at least one catalyst on a silica nanoparticle, adding a silica shell onto the catalyst coated silica nanoparticle, and etching the silica shell to create a nanoporous outer shell.

In accordance with another aspect of the instant invention, the catalytic nanoparticles comprise a silica nanoparticle coated with at least one catalyst encompassed by a hollow, nanoporous shell. The catalyst may be a metal catalyst such as palladium nanoparticles. In a particular embodiment, the hollow, nanoporous shell comprises zirconia. Methods of synthesizing these catalytic nanoparticles are also provided. In a particular embodiment, the method comprises coating at least one catalyst on a silica nanoparticle, adding a silica shell onto the catalyst coated silica nanoparticle, coating the silica shell with zirconia, and removing the silica shell (e.g., by etching with a base).

In accordance with another aspect of the instant invention, methods of catalyzing a chemical reaction are provided. In a particular embodiment, the methods comprise adding at least one catalytic nanoparticle of the instant invention to the chemical reaction. In a particular embodiment, the method comprises performing multiple rounds (e.g., 2 or more, 3 or more, 4 or more, 5 or more, etc.) of the chemical reaction with the same catalytic nanoparticles.

BRIEF DESCRIPTIONS OF THE DRAWING

FIG. 1 provides a schematic of the synthesis of $SiO_2$@Pd-PAMAM dendrimer core-shell microsphere catalysts.

Figure 2A:
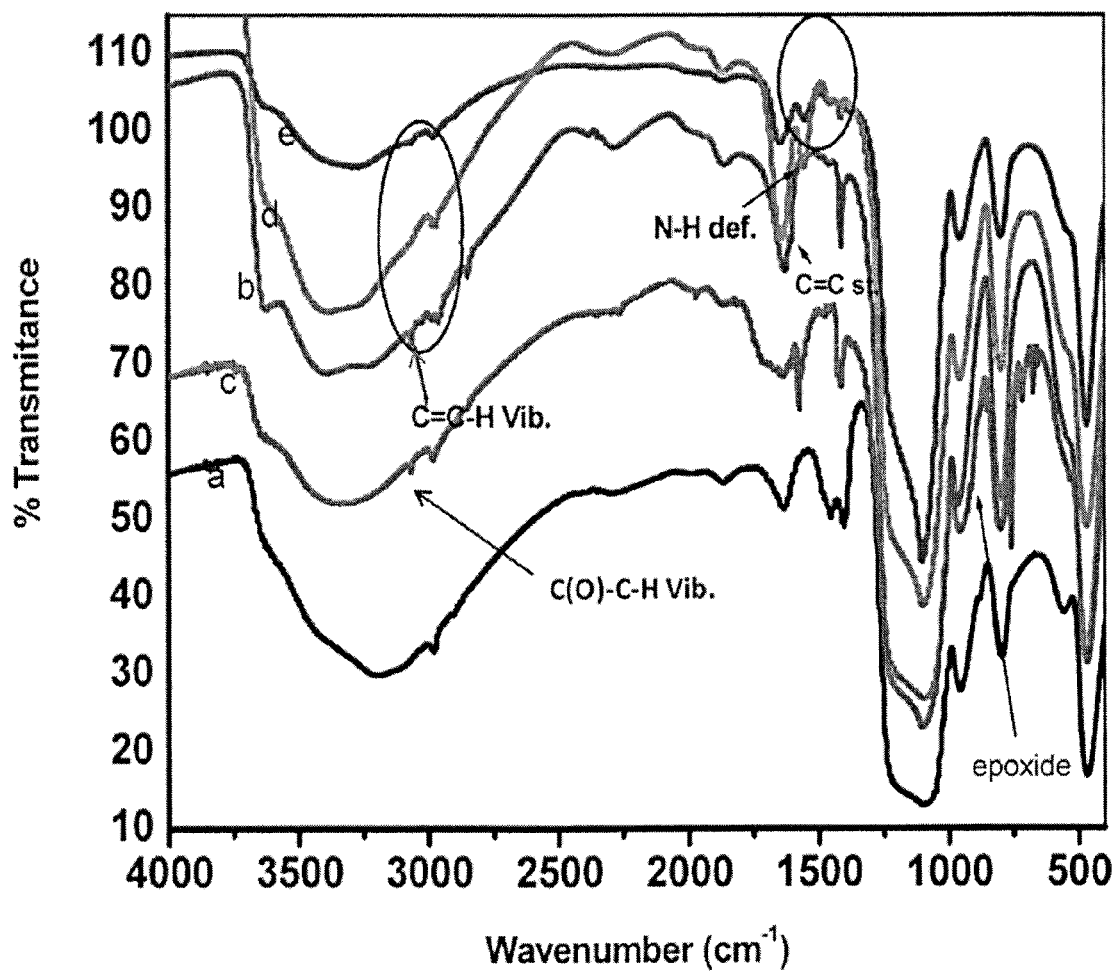
Figure 2B:
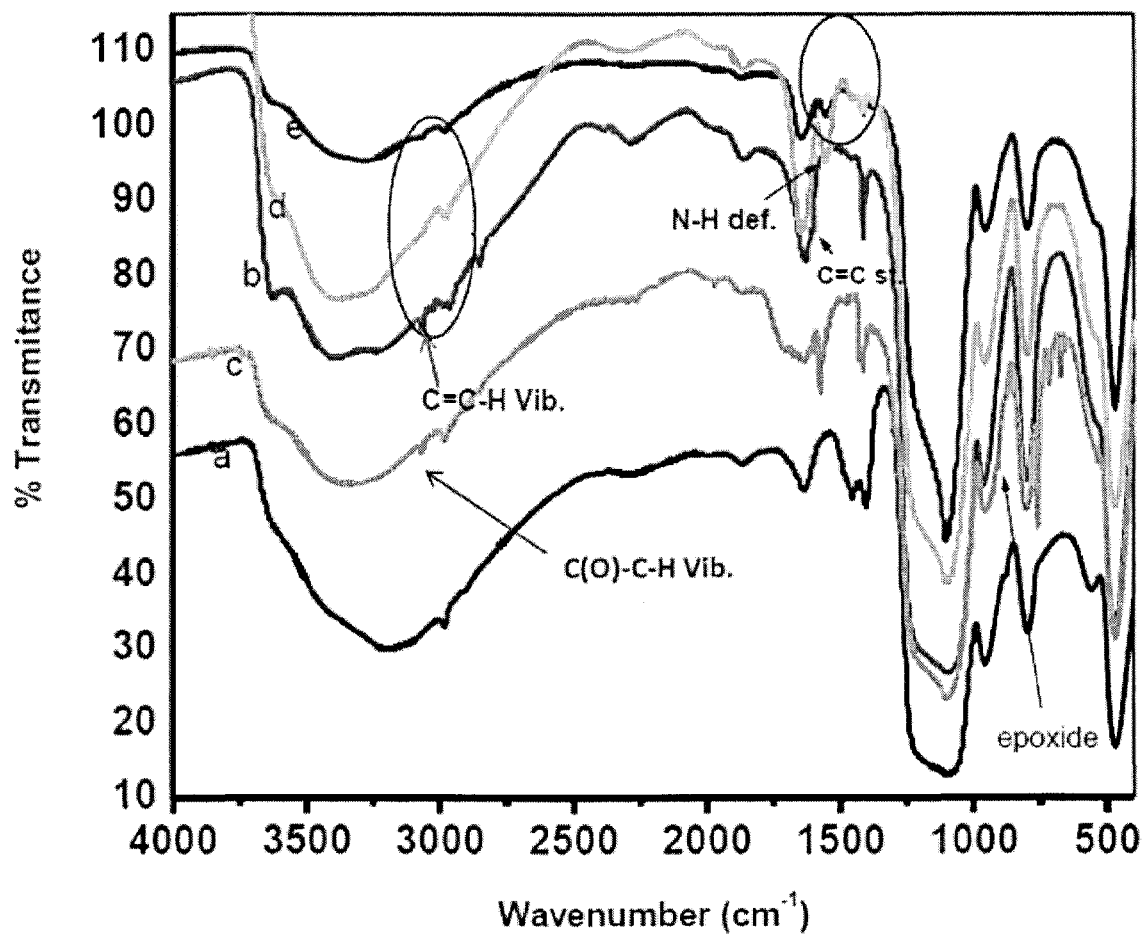

FIG. 2A provides FT-IR spectra of (a) $SiO_2$, (b) vinylsilica, and (c) epoxysilica microspheres and (d) $SiO_2$@PAMAM and (e) SiO2@Pd-PAMAM core-shell microspheres. FIG. 2B provides enlarged FT-IR spectra of the microspheres.

Figure 2C:
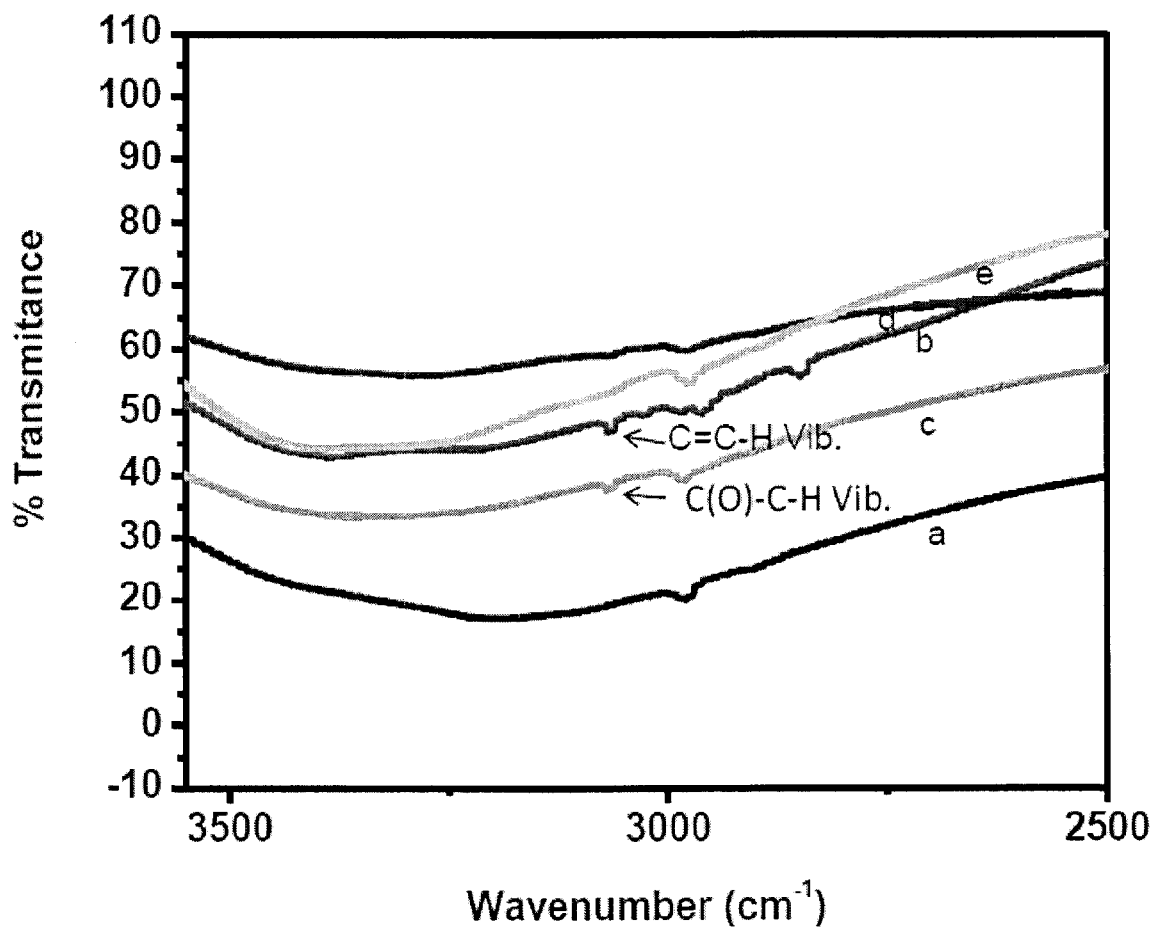
Figure 2D:
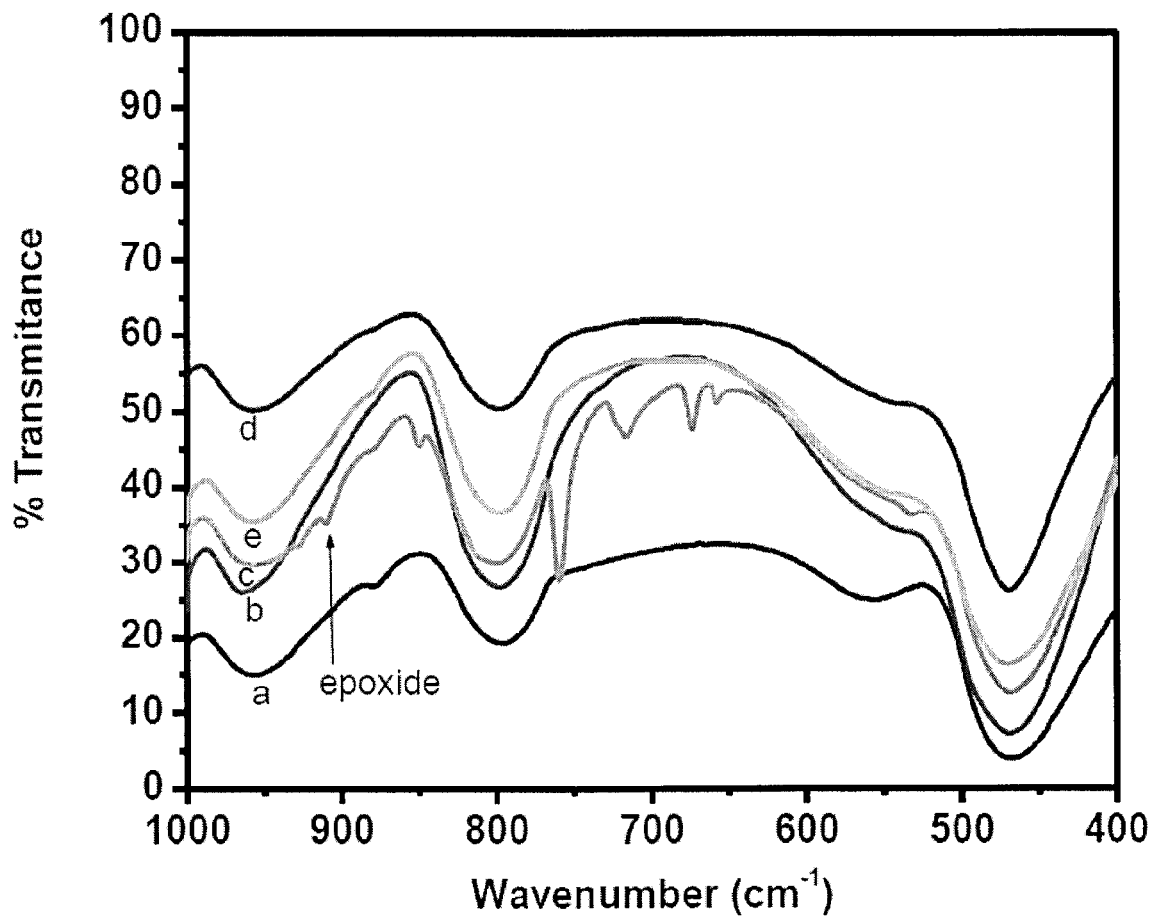
Figure 2E:
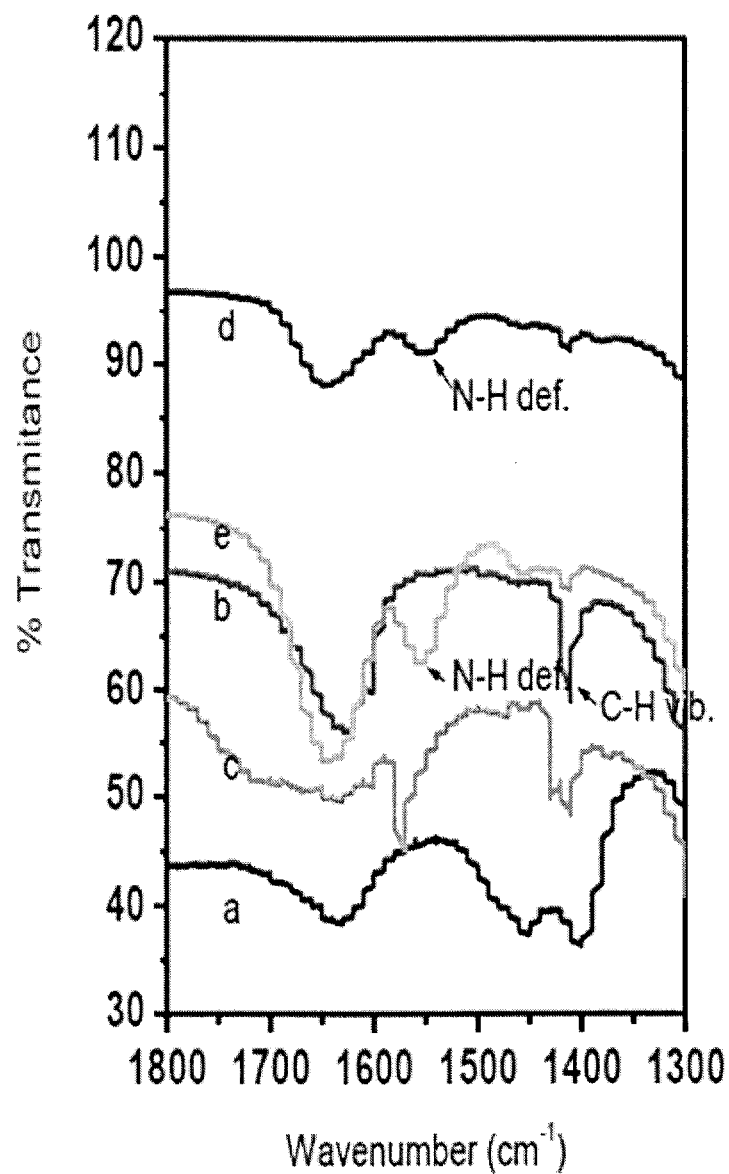
Figure 2F:
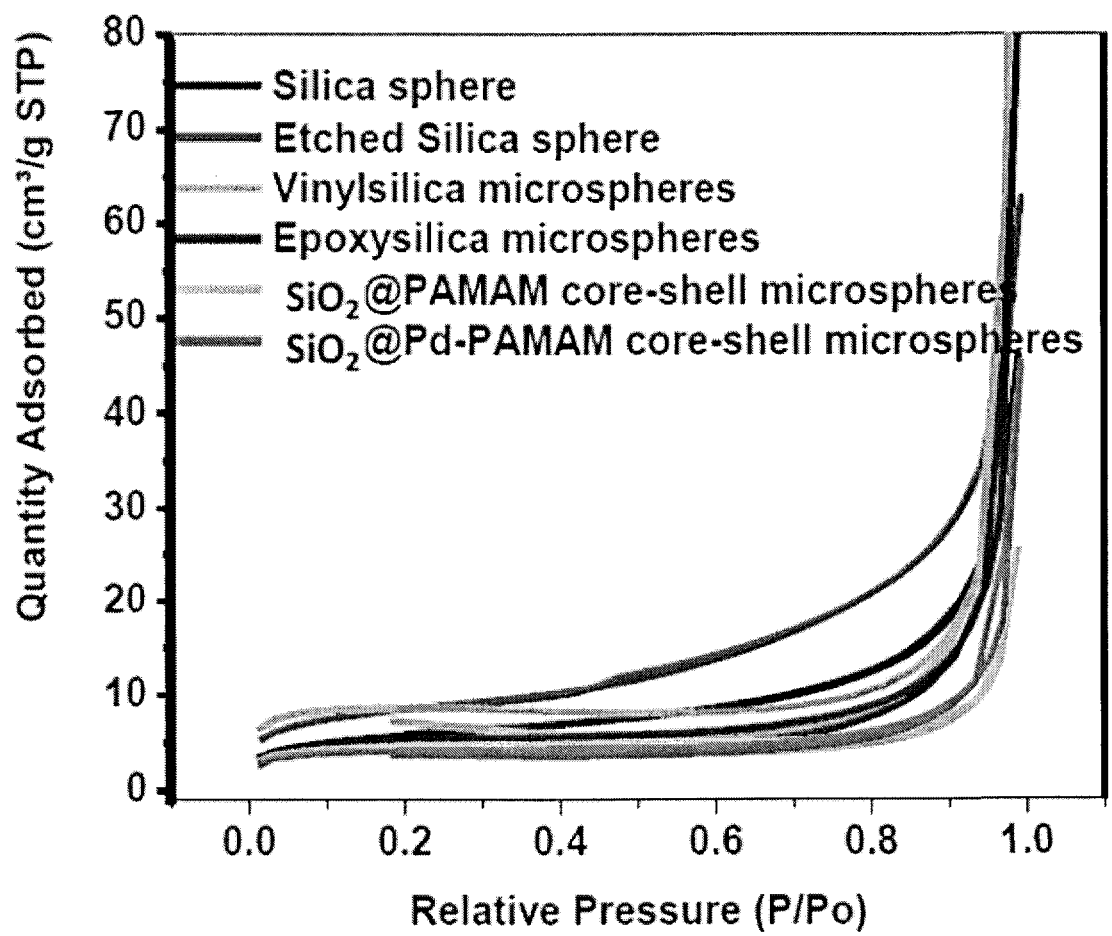

FIG. 2C provides expanded FT-IR spectra between 2500-3550 $cm^{-1}$ of the microspheres. FIG. 2D provides an expanded view of FT-IR spectra between 400-1000 $cm^{-1}$ of the microspheres. FIG. 2E provides an expanded view of FT-IR spectra 1300-1800 $cm^{-1}$ of the microspheres. FIG. 2F provides $N_2$ gas adsorption-desorption isotherms of the microspheres.

Figure 3:
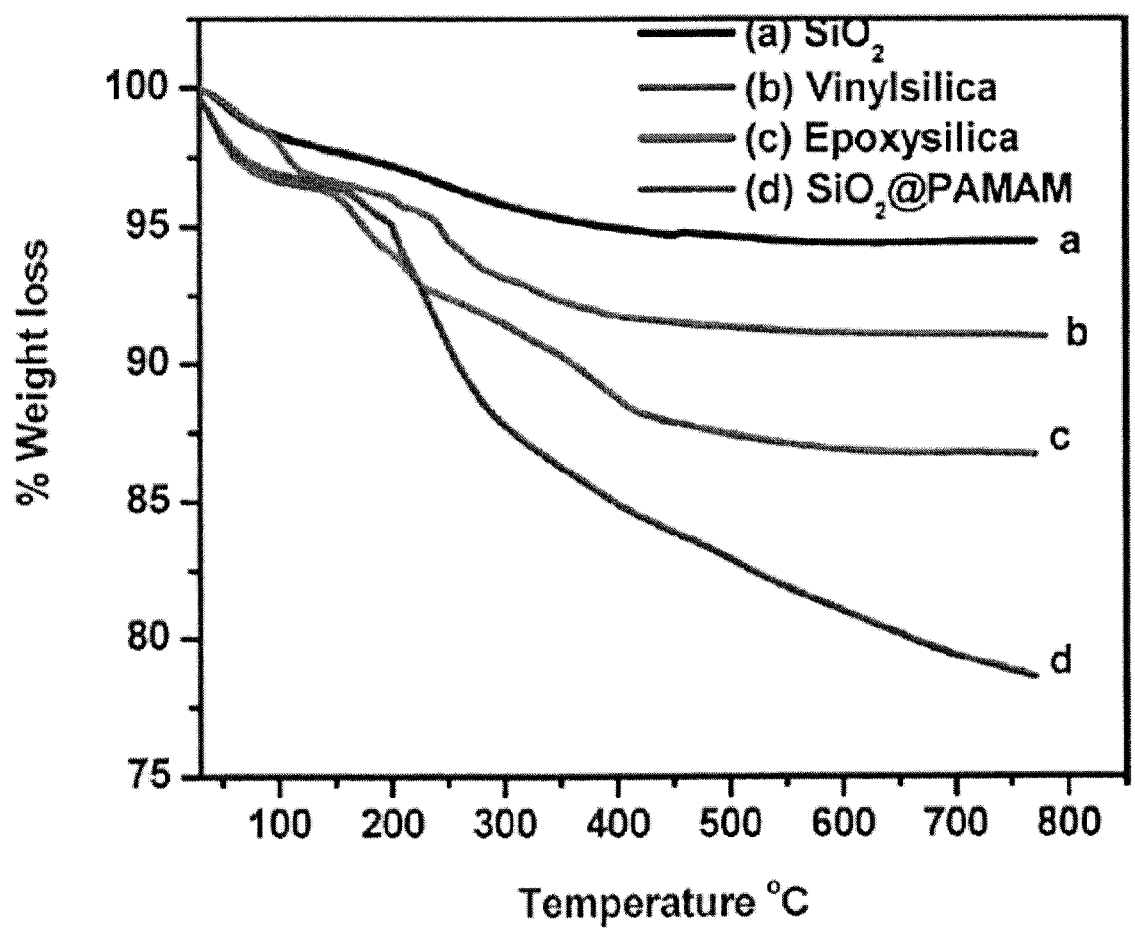

FIG. 3 provides the TGA of (a) etched silica, $SiO_2$, (b) vinylsilica, and (c) epoxysilica microspheres and (d) $SiO_2$@PAMAM core-shell microspheres.

FIGS. 4A and 4B provide low magnification and FIG. 4C provides high magnification TEM images of etched $SiO_2$ microspheres. FIGS. 4D and 4E provide enlarged TEM images of $SiO_2$@Pd-PAMAM core-shell microspheres. FIG. 4F provides the size distribution of Pd nanoparticles in $SiO_2$@Pd-PAMAM core-shell microspheres. FIG. 4G provides TEM images of the etched $SiO_2$ microsphere cores that were used as a support for PAMAM dendrimers as well as Pd-PAMAM nanoparticles prepared by etching $SiO_2$ microspheres with dilute KOH solution. FIG. 4H provides enlarged TEM images $SiO_2$@Pd-PAMAM core-shell microspheres.

FIGS. 5A-5E provide TEM images of different views of the control samples, $SiO_2$@Pd core-shell microspheres that were prepared without using G4 PAMAM dendrimer shells. The images show that much fewer Pd nanoparticles than those in the $SiO_2$@Pd-PAMAM core-shell microspheres.

Figure 6:
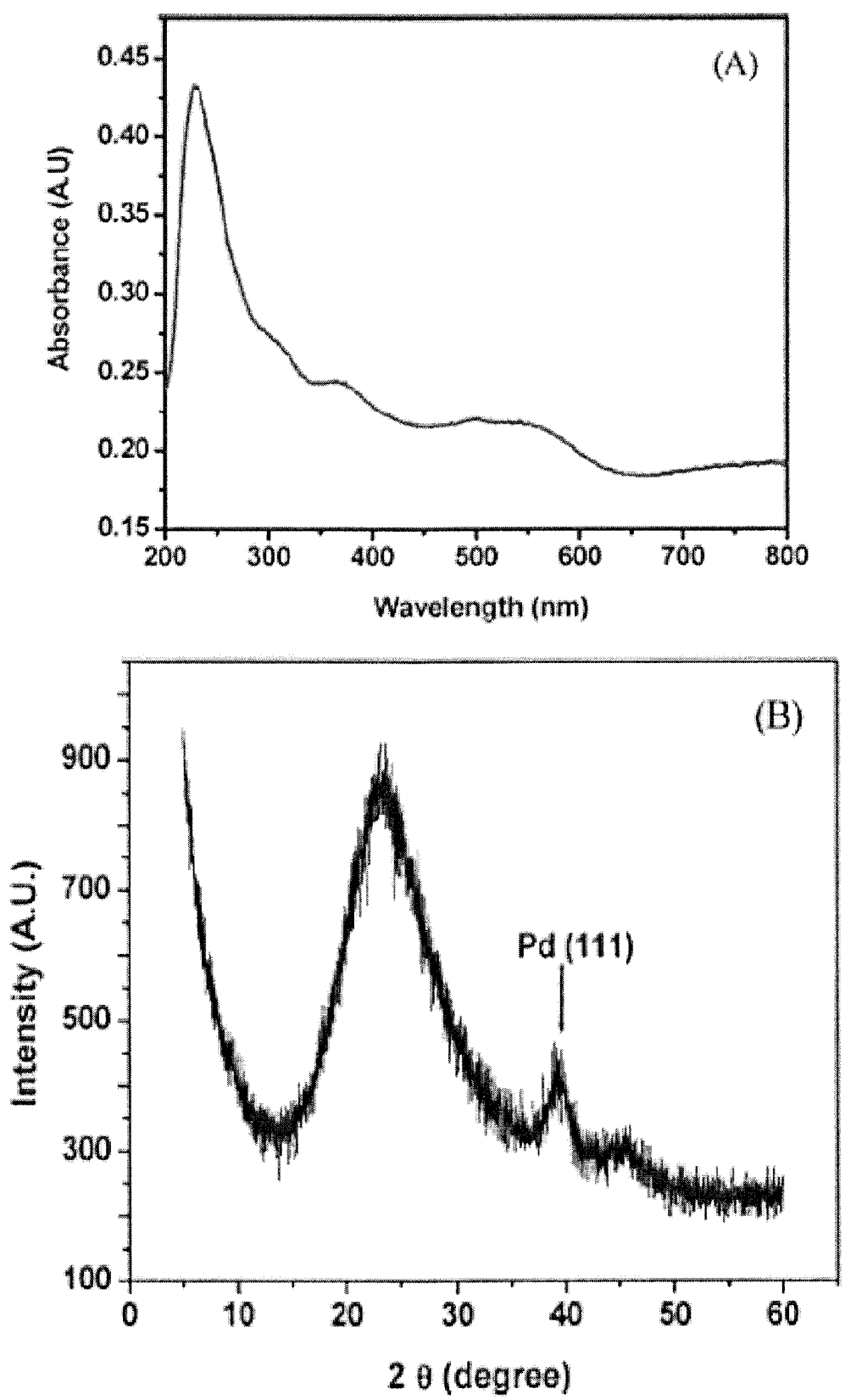
Figure 7A:
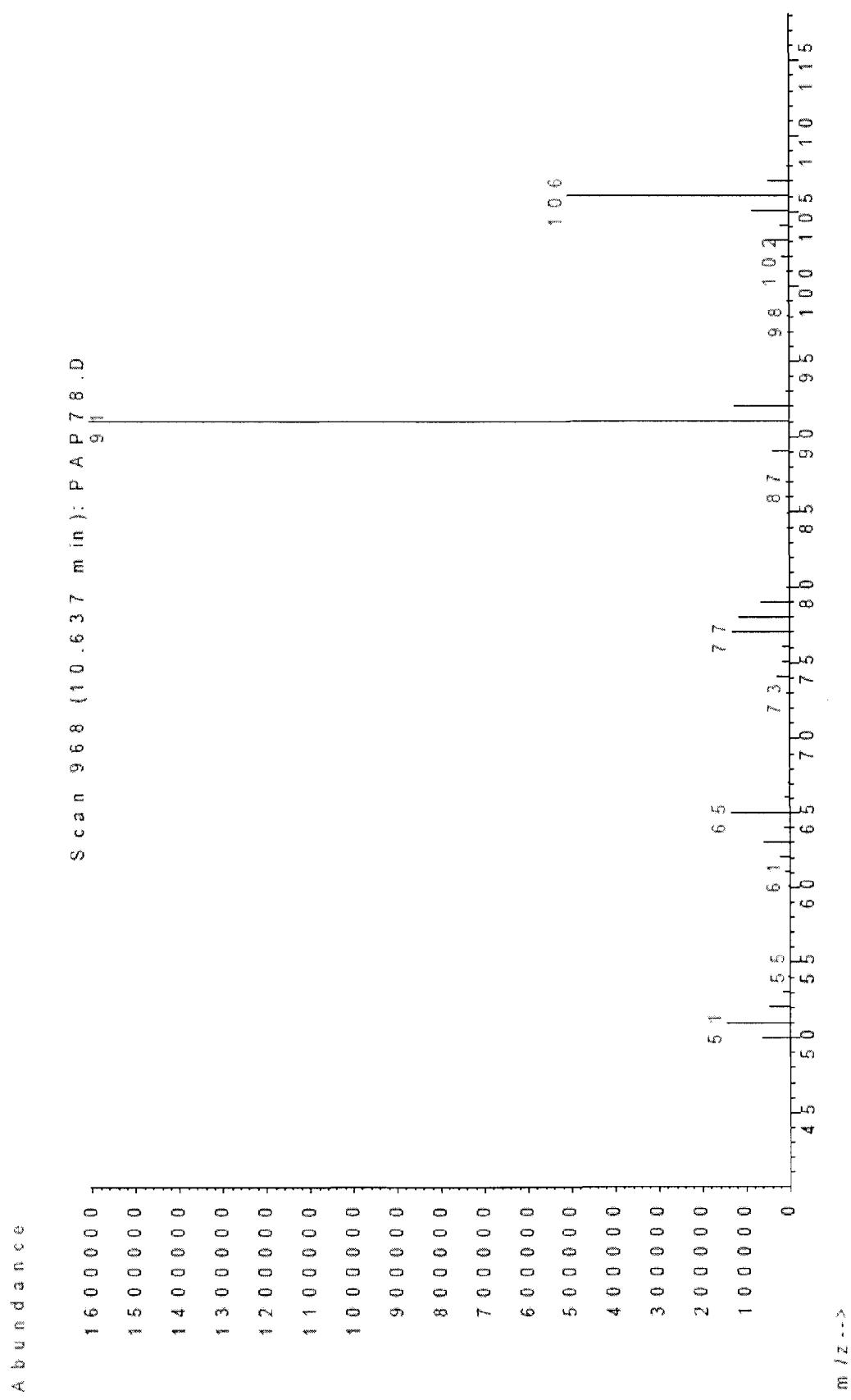
Figure 7B:
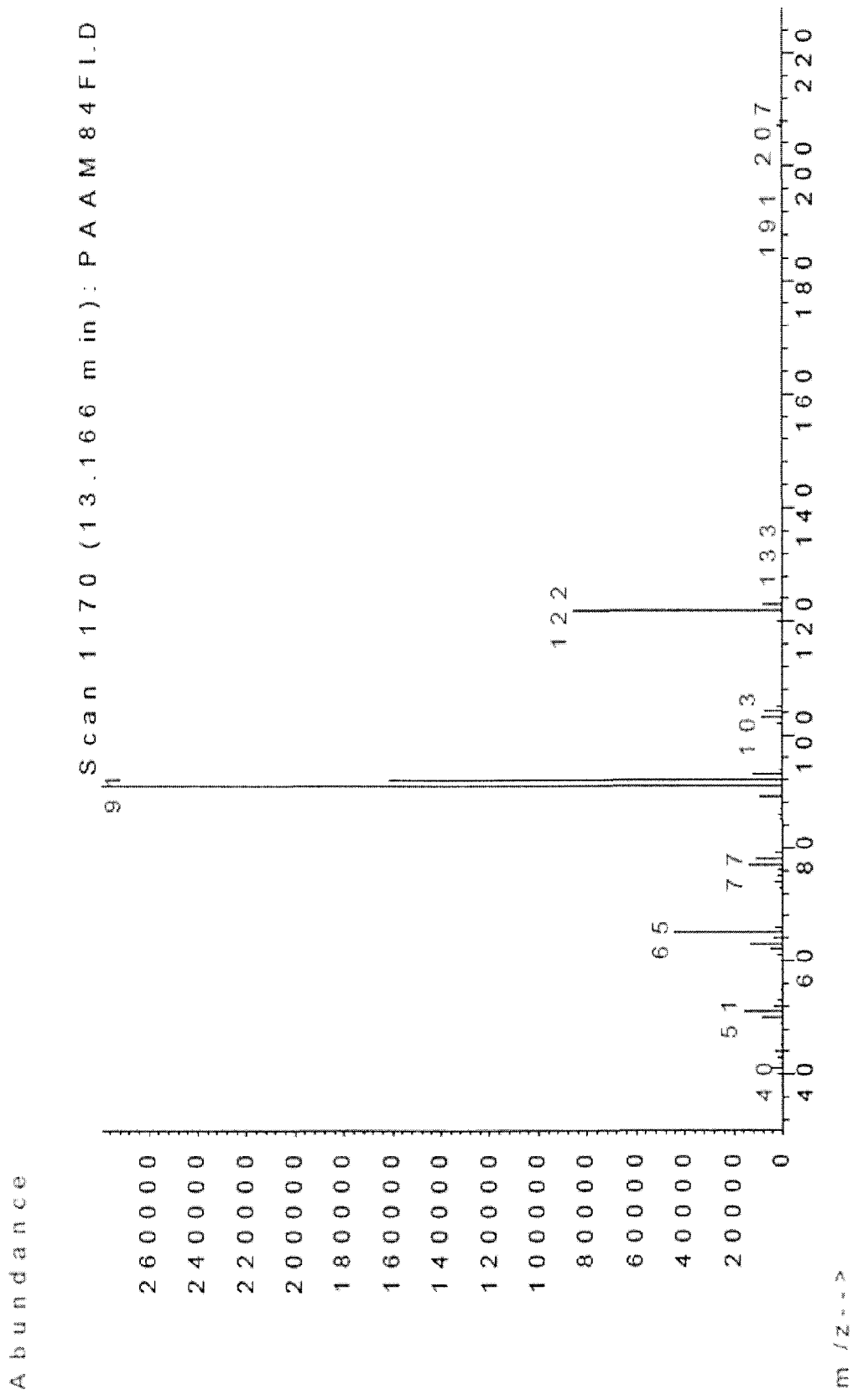
Figure 7C:
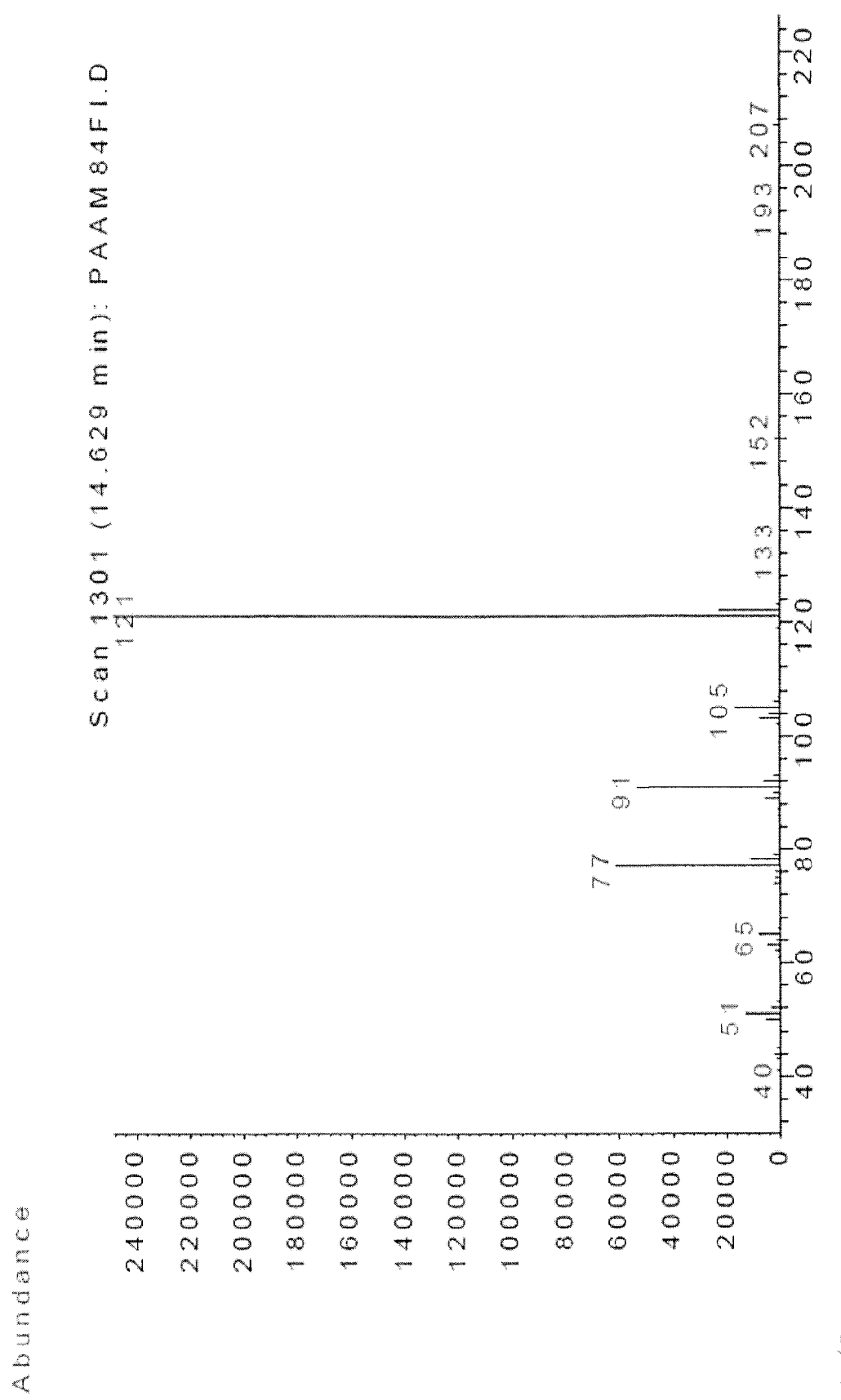
Figure 7D:
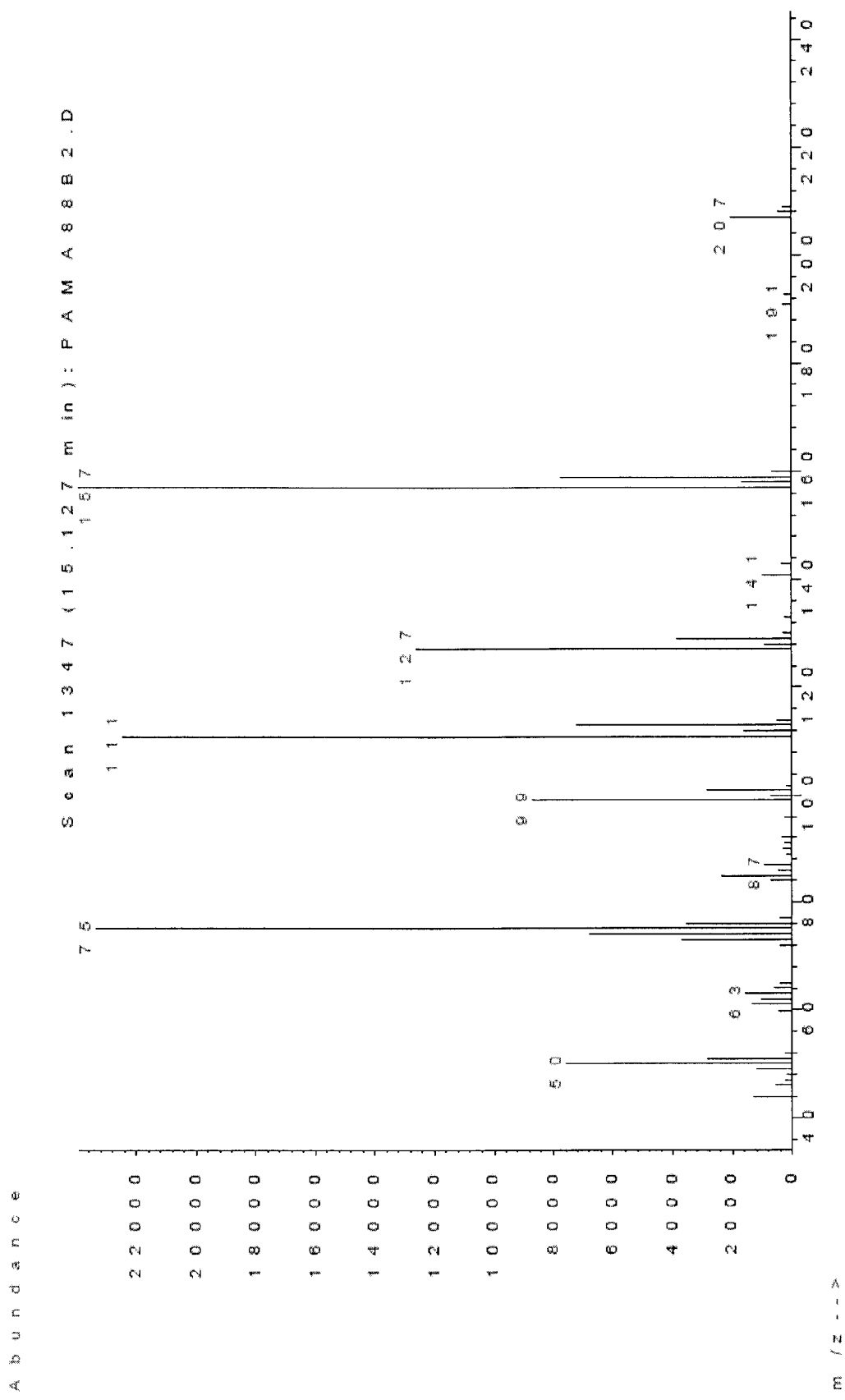
Figure 7E:
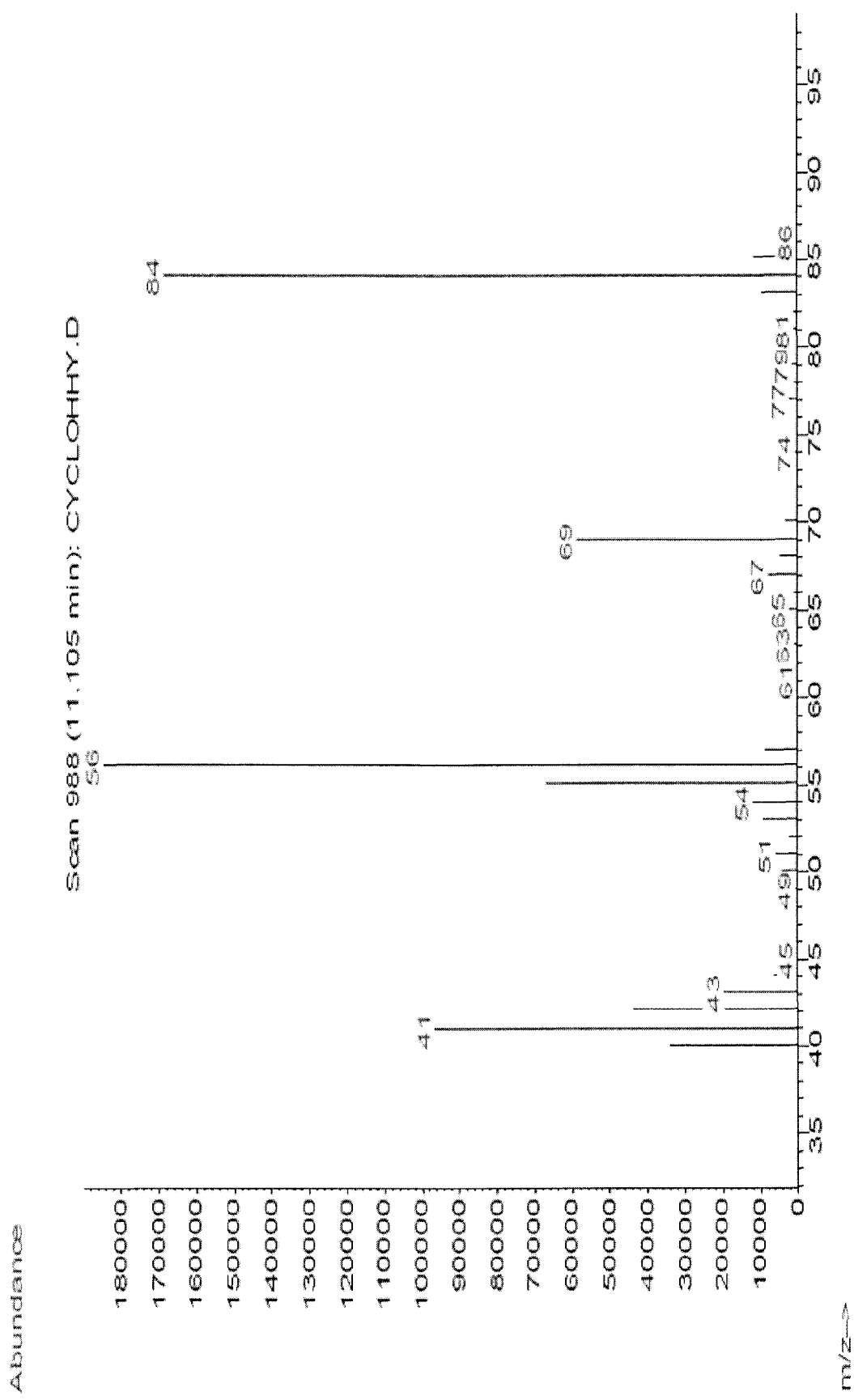
Figure 7F:
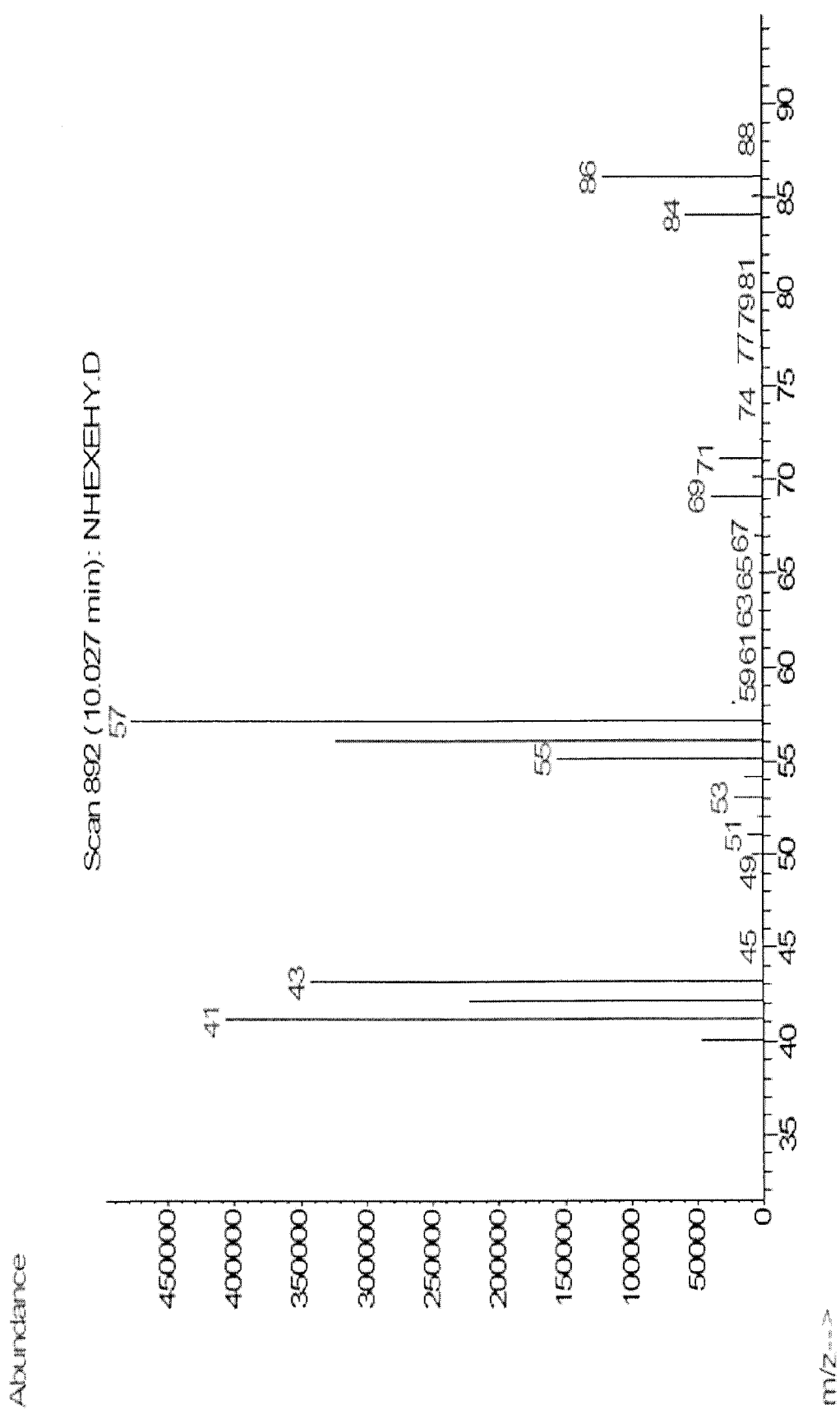
Figure 7G:
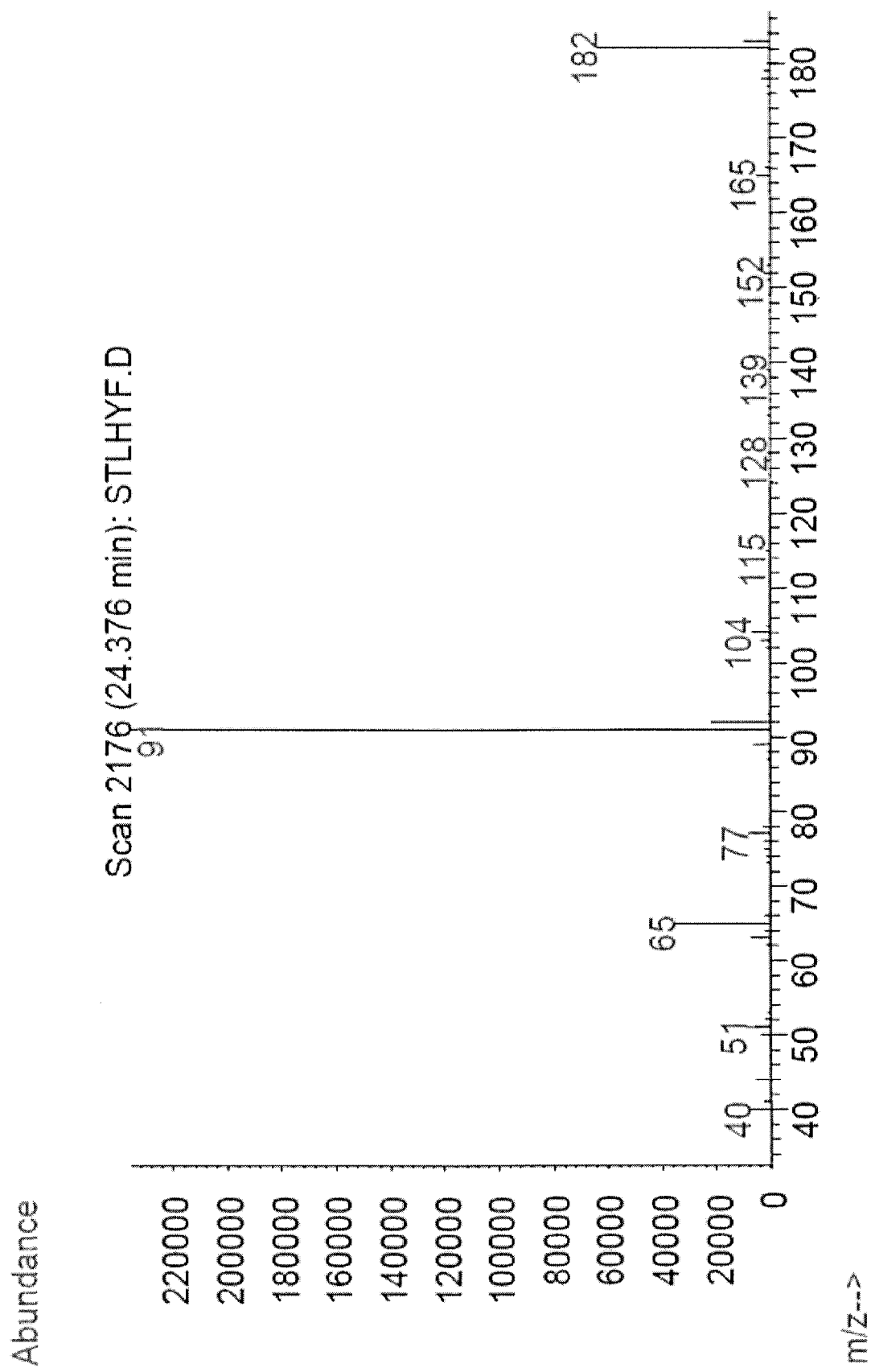
Figure 7H:
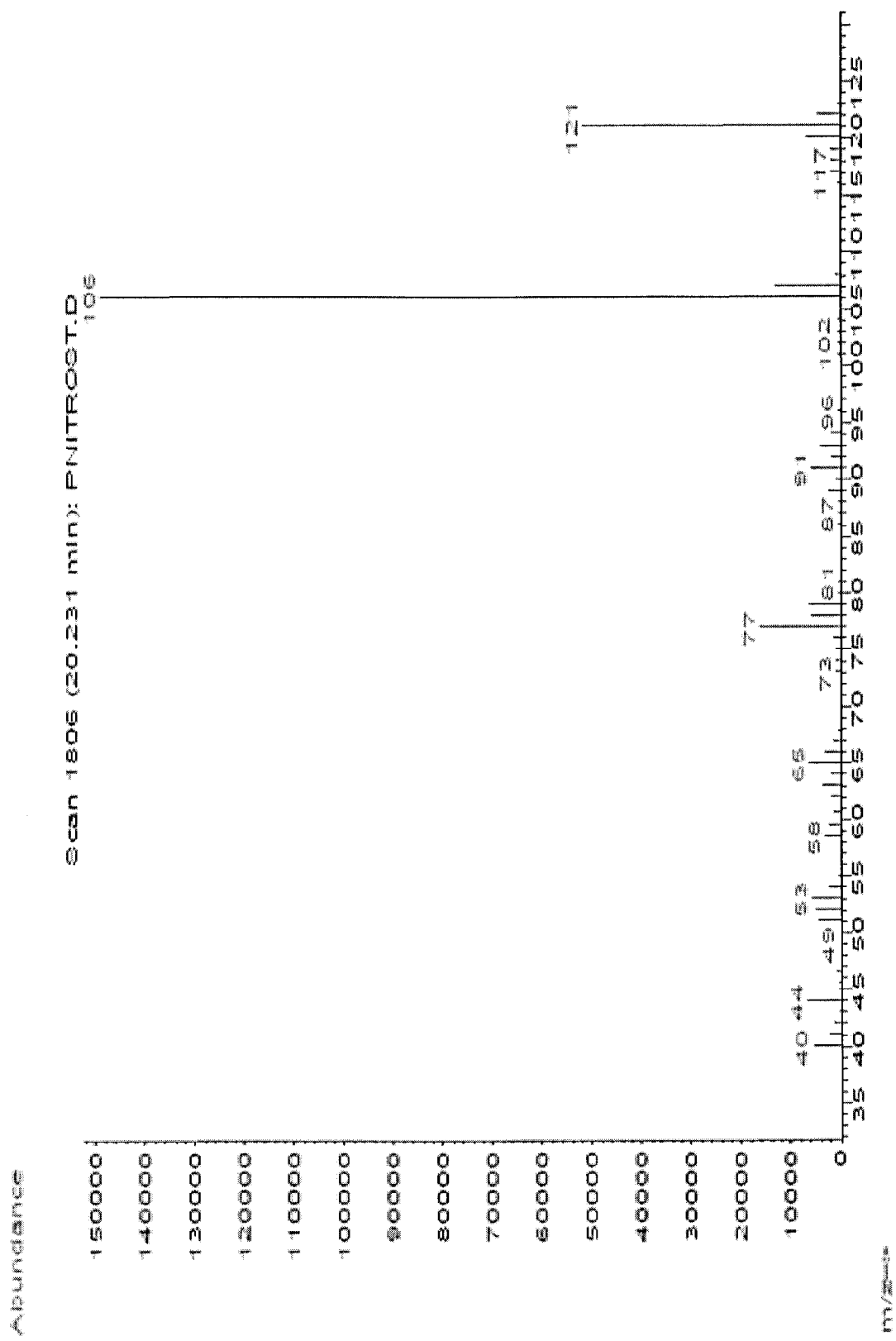
Figure 7I:
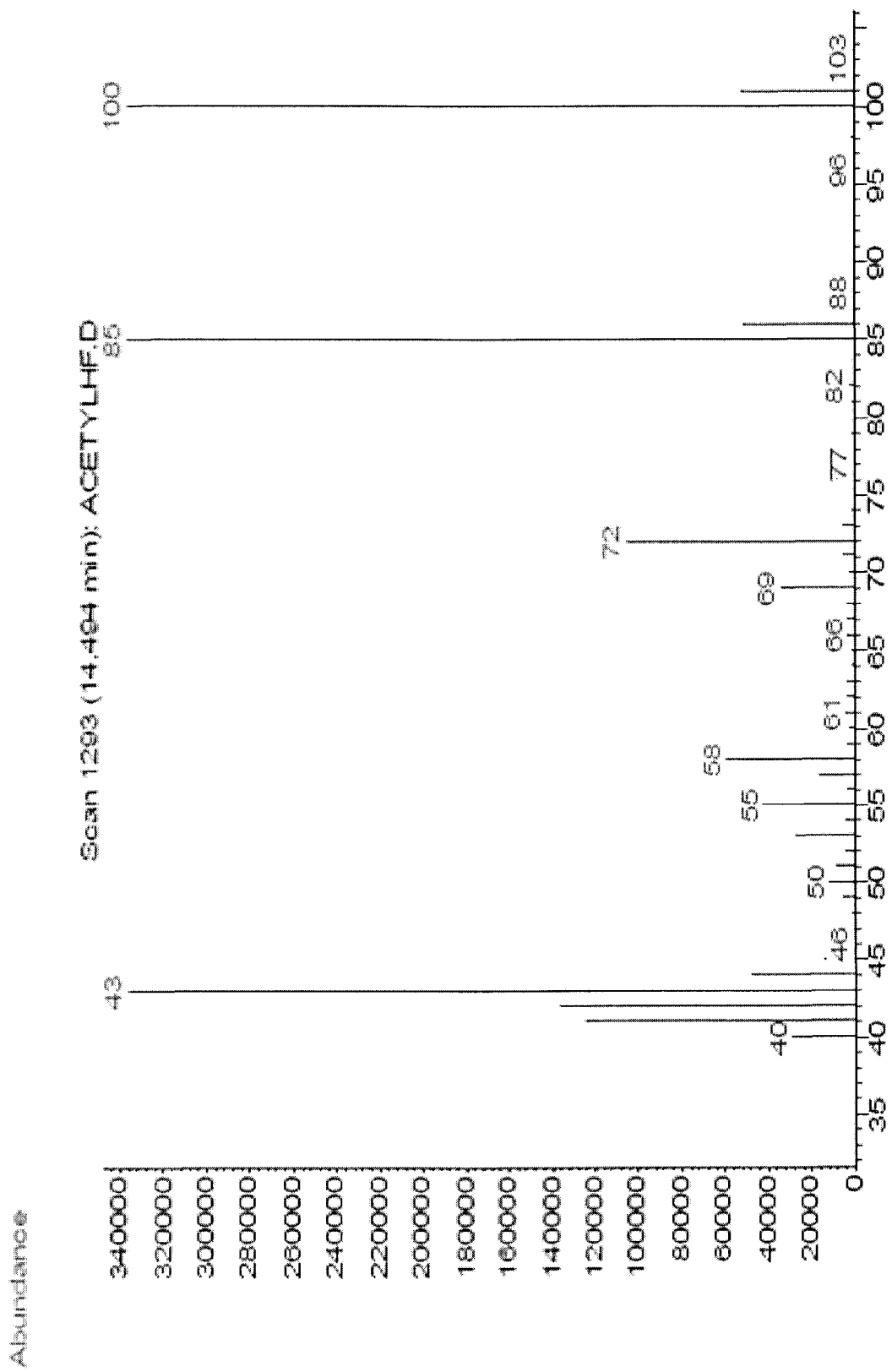

FIG. 6A provides the UV-vis spectra of $SiO_2$@Pd-PAMAM core-shell microspheres. FIG. 6B provides the powder X-ray diffraction pattern of $SiO_2$@Pd-PAMAM core-shell microspheres.

FIG. 7 provides GC-MS spectra of certain products from $SiO_2$/Pd-PAMAM core-shell nanospheres catalyzed hydrogenation reactions: (FIG. 7A) ethylbenzene from styrene, (FIG. 7B) phenylethanol from styrene oxide, (FIG. 7C) phenylacetaldehyde from styrene oxide, (FIG. 7D) 4-chloroaniline from 4-chloronitrobenzene, (FIG. 7E) cyclohexane from cyclohexene, (FIG. 7F) hexane from n-hexene, (FIG. 7G) 1,2-diphenylethane from trans-stilbene, (FIG. 7H) 4-ethylaniline from nitrostyrene, and (FIG. 7I) 4-hydroxypentane-2-one from acetyleacetone.

Figure 8:
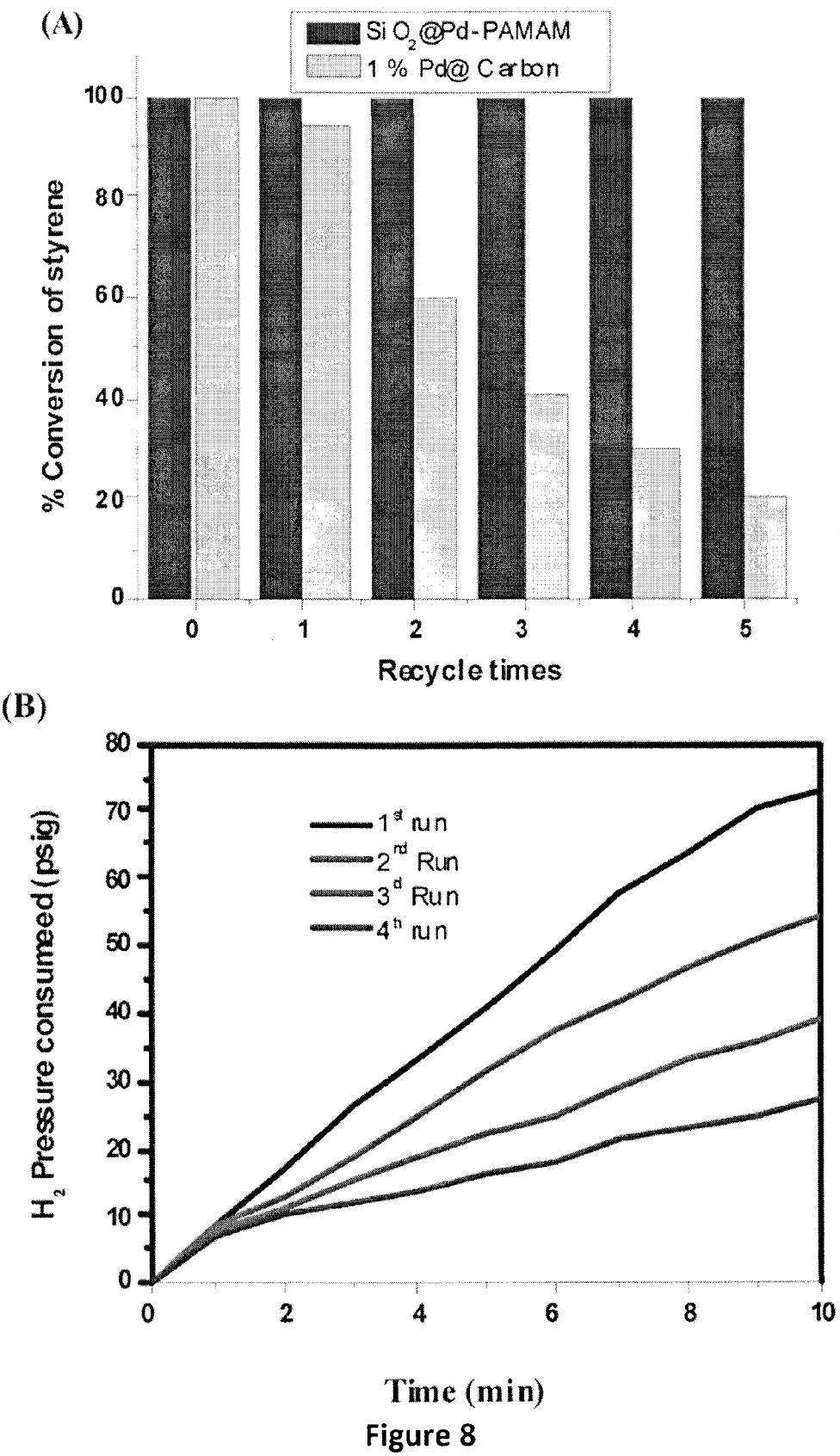

FIG. 8A provides a comparative graph for % conversion of styrene in 10 minutes versus recycle time of $SiO_2$@Pd-PAMAM core-shell catalysts and commercial Pd/C (1%) catalyst. FIG. 8B provides the catalytic efficiency of recycled Pd/C catalyst showing significant catalytic activity loss after recycling. A similar graph for $SiO_2$@Pd-PAMAM core-shell catalysts was difficult to plot because of the materials' very high catalytic activities and the fast $H_2$ consumption by the reaction.

Figure 9:
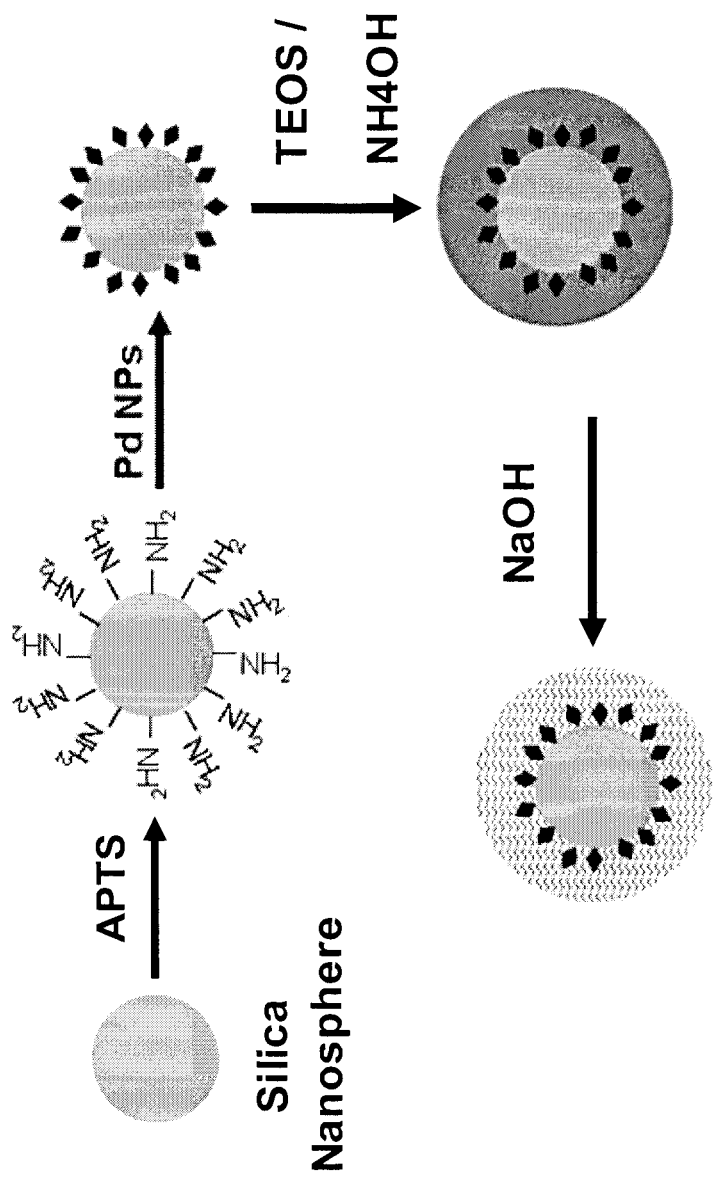

FIG. 9 is a schematic representation of the synthesis of $SiO_2$/Pd-NP/Porous-$SiO_2$ core-shell-shell nanospheres.

FIGS. 10A-10C provide representative TEM images of Pd nanoparticles (20 nm) supported on amino-modified silica nanospheres (FIG. 10A), $SiO_2$/Pd-NP/$SiO_2$ core-shell-shell nanospheres (FIG. 10B), and etched $SiO_2$/Pd-NP/Porous-$SiO_2$ core-shell-shell nanospheres (FIG. 10C). FIG. 10D provides a TEM image of octahedral shaped Pd nanoparticles (~20 nm) synthesized by following the procedure reported by Lim et al. (Angew. Chem. Int. Ed. (2007) 46:9279).

FIGS. 11A-11C provide TEM images of $SiO_2$/Pd-NP core-shell nanospheres with 20 nm Pd-NP chemisorbed on aminopropyl-modified silica nanospheres (FIG. 11A) and the corresponding $SiO_2$/Pd-NP/$SiO_2$ core-shell-shell nanospheres (FIG. 11B), and $SiO_2$/Pd-NP/Porous-$SiO_2$ core-shell-shell nanospheres etched for 120 minutes (FIG. 11C).

Figure 11:
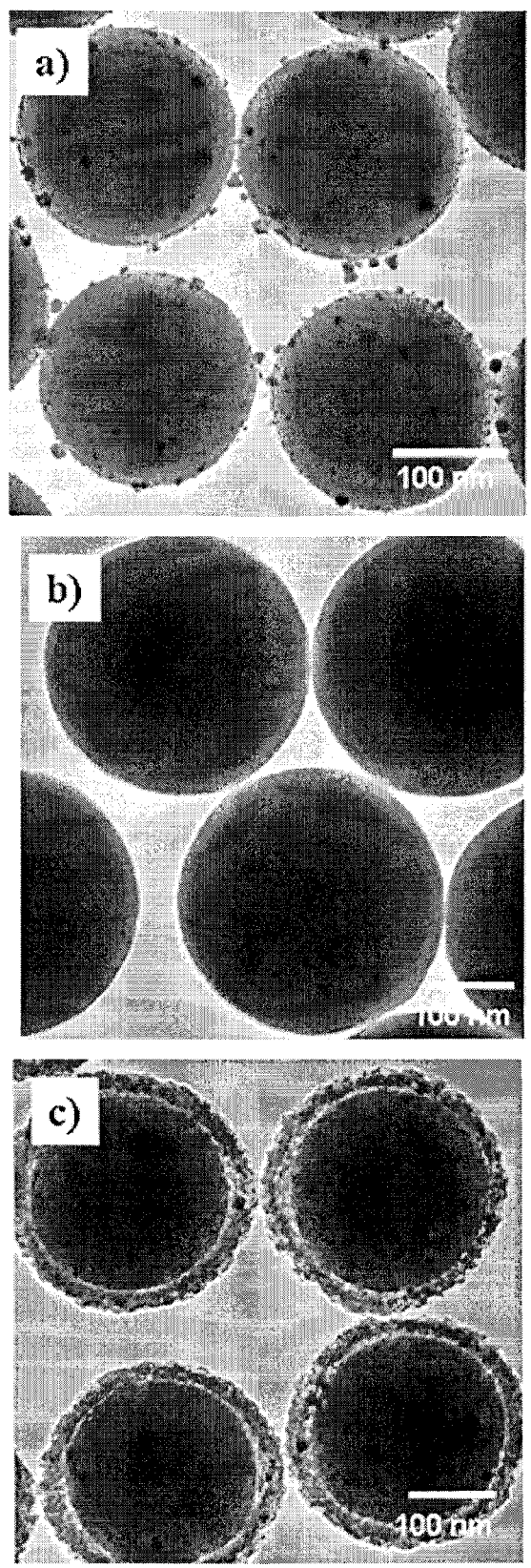
Figure 12:
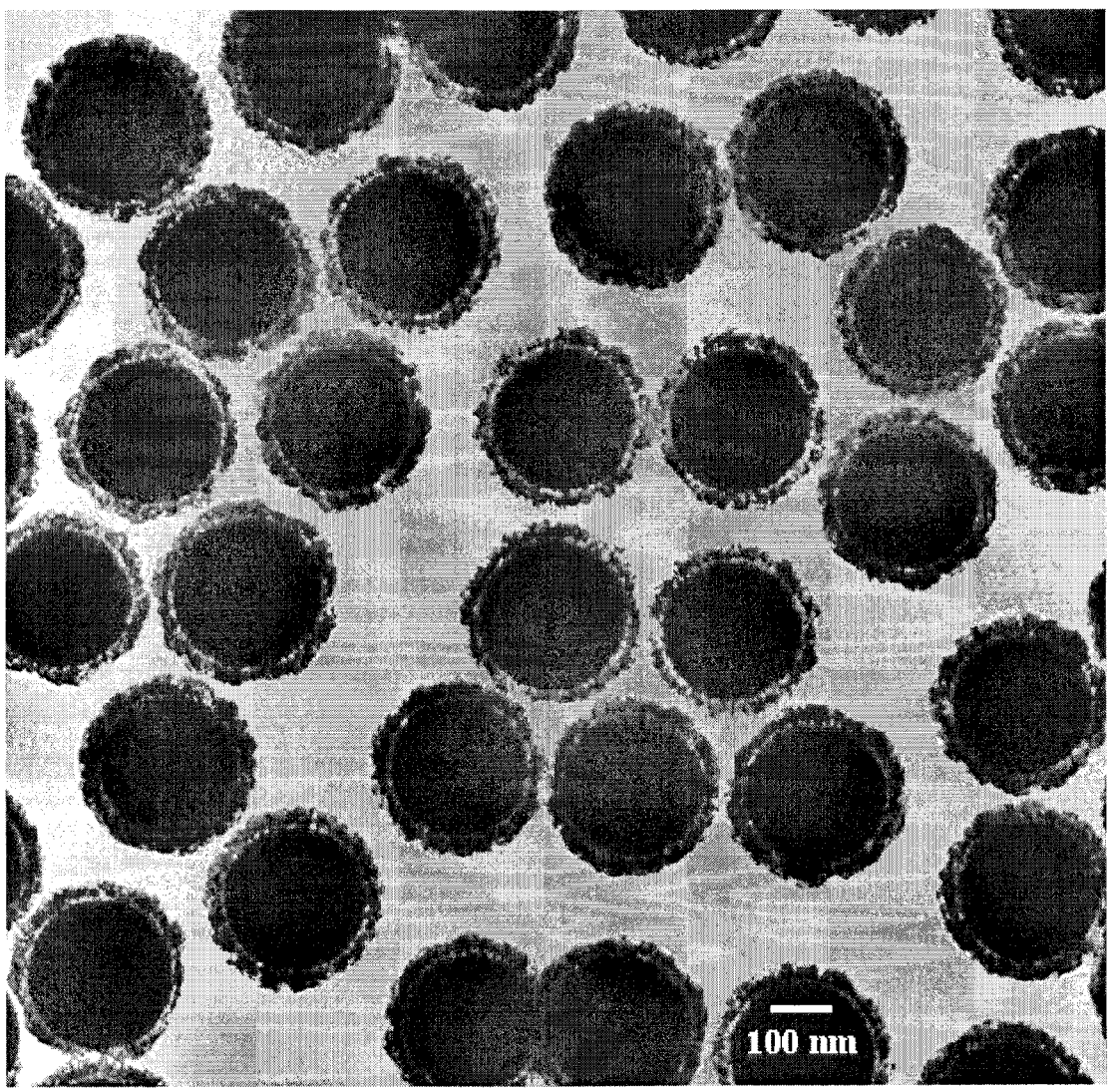

FIG. 12 provides a representative TEM image of etched $SiO_2$/Pd—NP/Porous $SiO_2$ core-shell-shell nanospheres (same sample as the one in FIG. 11C except more magnified).

Figure 13:
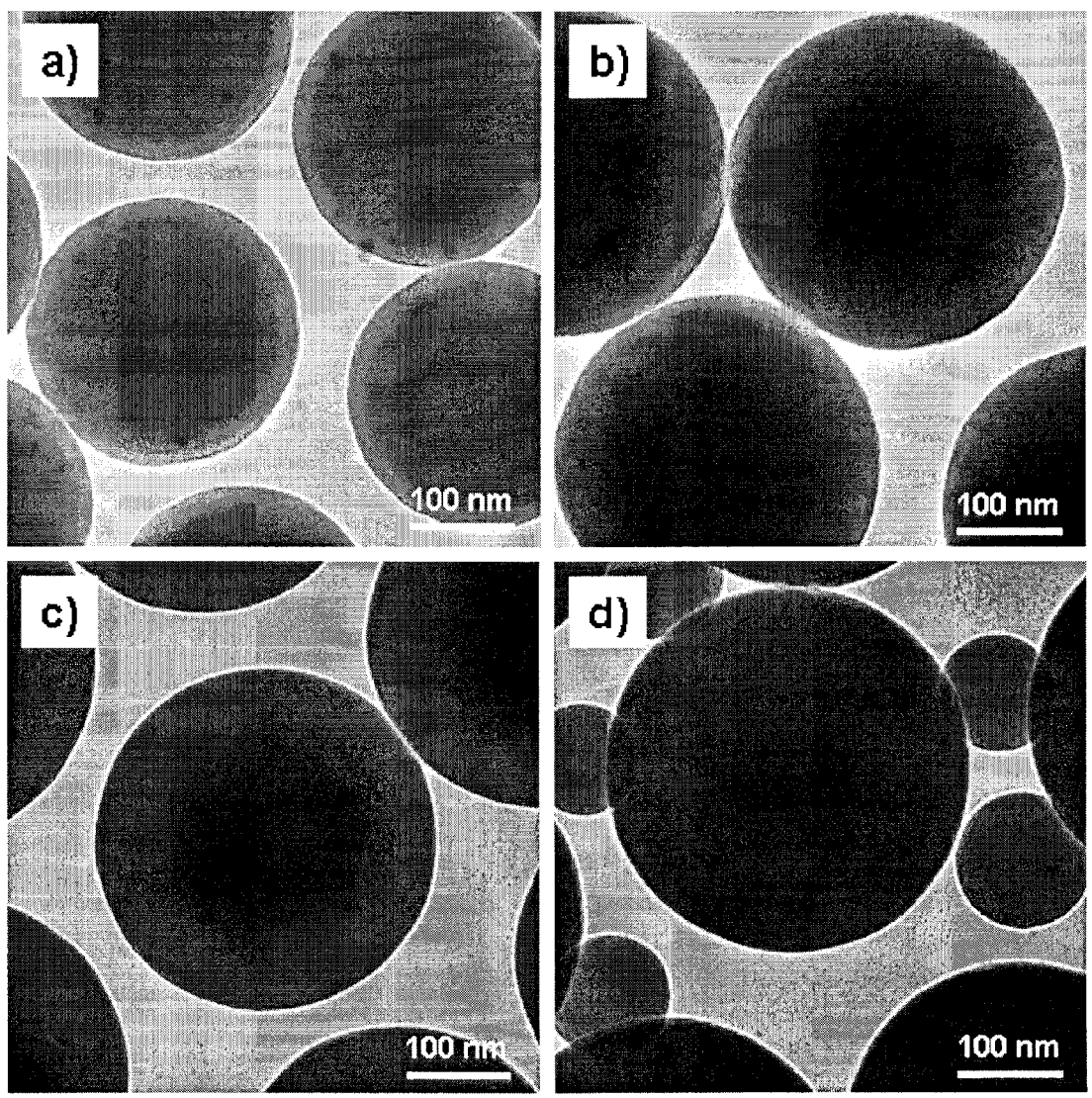
Figure 13:
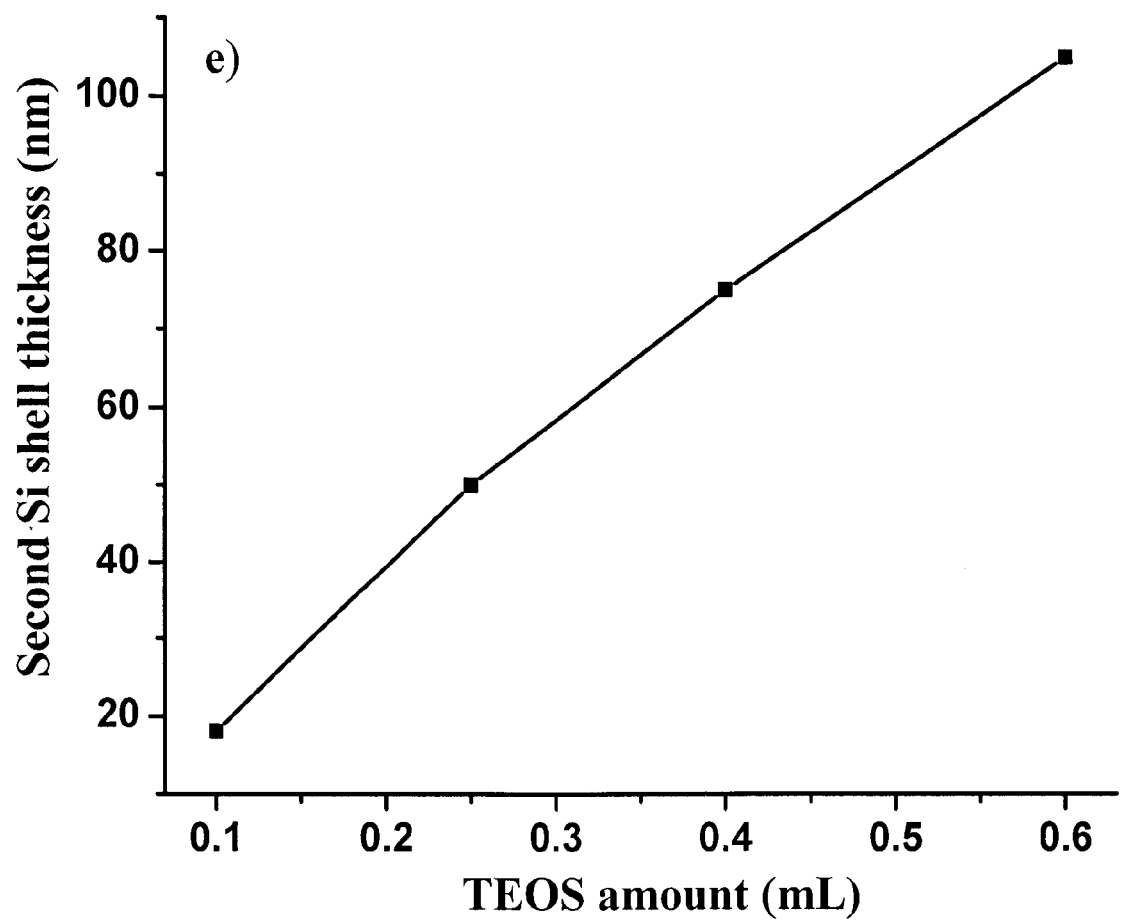

FIG. 13 provides representative TEM images of $SiO_2$/Pd-NP/$SiO_2$ core-shell-shell nanospheres possessing different thickness of silica shell made by using different amounts of TEOS: 0.1 mL TEOS (FIG. 13A), 0.25 mL TEOS (FIG. 13B), 0.4 mL TEOS (FIG. 13C), and 0.6 mL TEOS (FIG. 13D). FIG. 13E provides a graph showing a linear relationship between the thickness of the silica shell and the amount of TEOS used at a given $NH_4OH$ concentration and deposition time.

Figure 14:
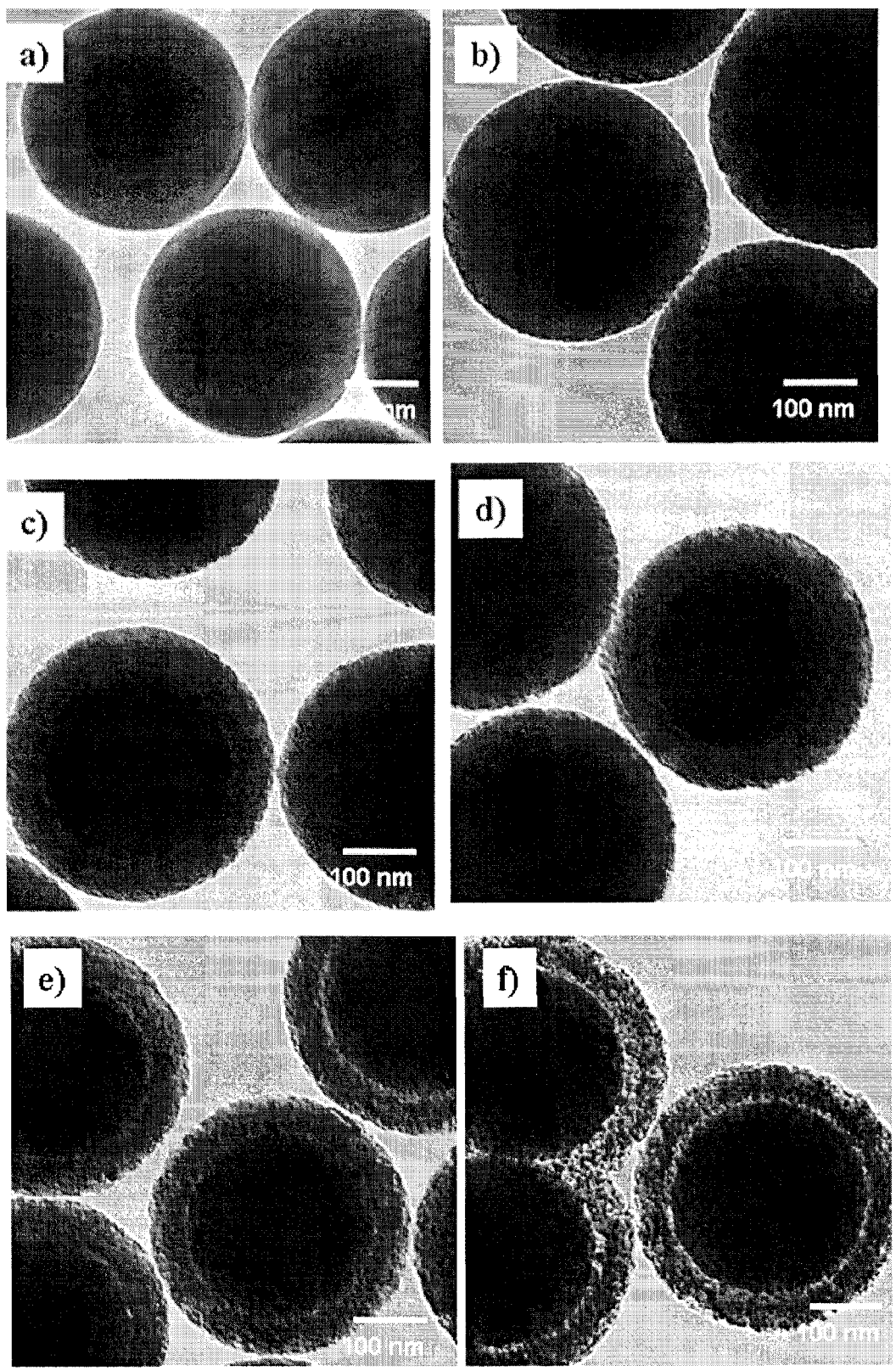

FIG. 14 provides TEM images of $SiO_2$/Pd-NP/$SiO_2$ core-shell-shell nanospheres (FIG. 14A) and the corresponding $SiO_2$/Pd-NP/Porous-$SiO_2$ core-shell-shell nanospheres after etching for: 50 (FIG. 14B), 60 (FIG. 14C), 70 (FIG. 14D), 80 (FIG. 14E) and 100 minutes (FIG. 14F). Scale bars=100 nm in all images.

Figure 15:
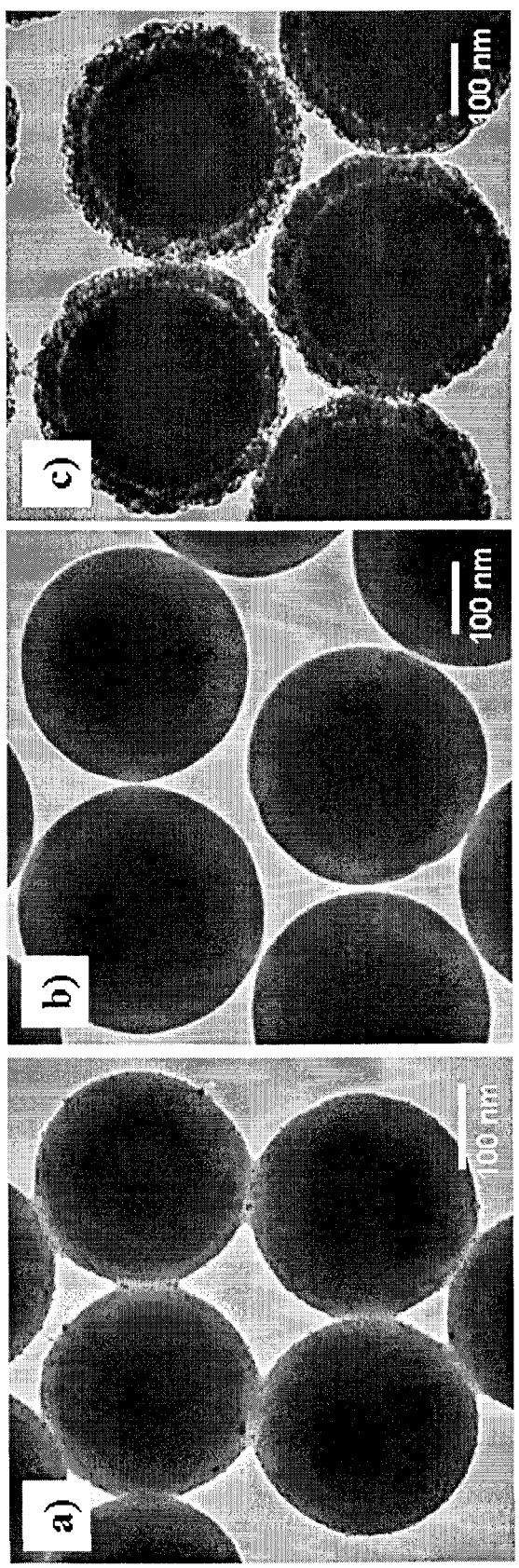

FIG. 15 provides large area TEM images of Pd-NP (5 nm) supported onto amino-modified silica nanospheres (FIG. 15A), $SiO_2$/Pd-NP/$SiO_2$ core-shell-shell nanospheres (FIG. 15B), and etched $SiO_2$/PdNP/Porous $SiO_2$ core-shell-shell nanospheres etched for 80 minutes (FIG. 15C).

Figure 16:
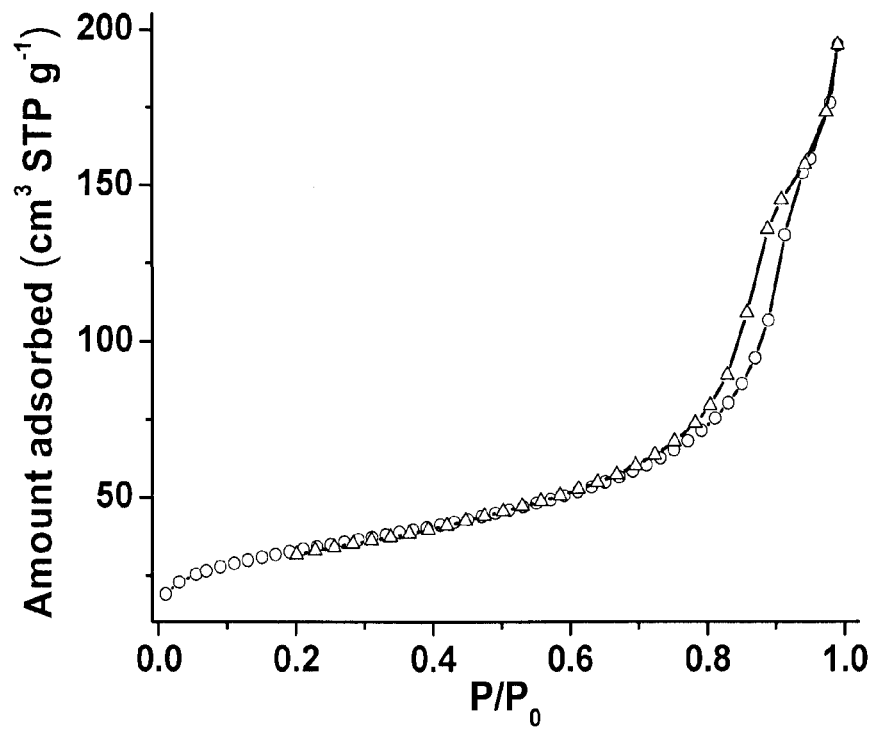
Figure 16:
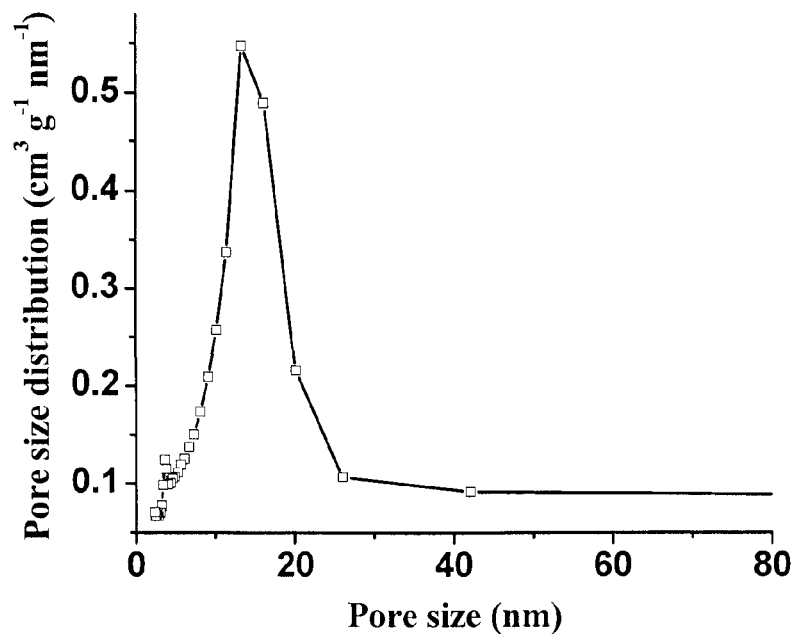

FIG. 16 provides nitrogen adsorption-desorption isotherms of $SiO_2$/Pd—NP/Porous-$SiO_2$ core-shell-shell nanospheres that were synthesized by etching in aqueous NaOH solution for 80 minutes (FIG. 16A) and their corresponding pore size distribution (FIG. 16B).

Figure 17:
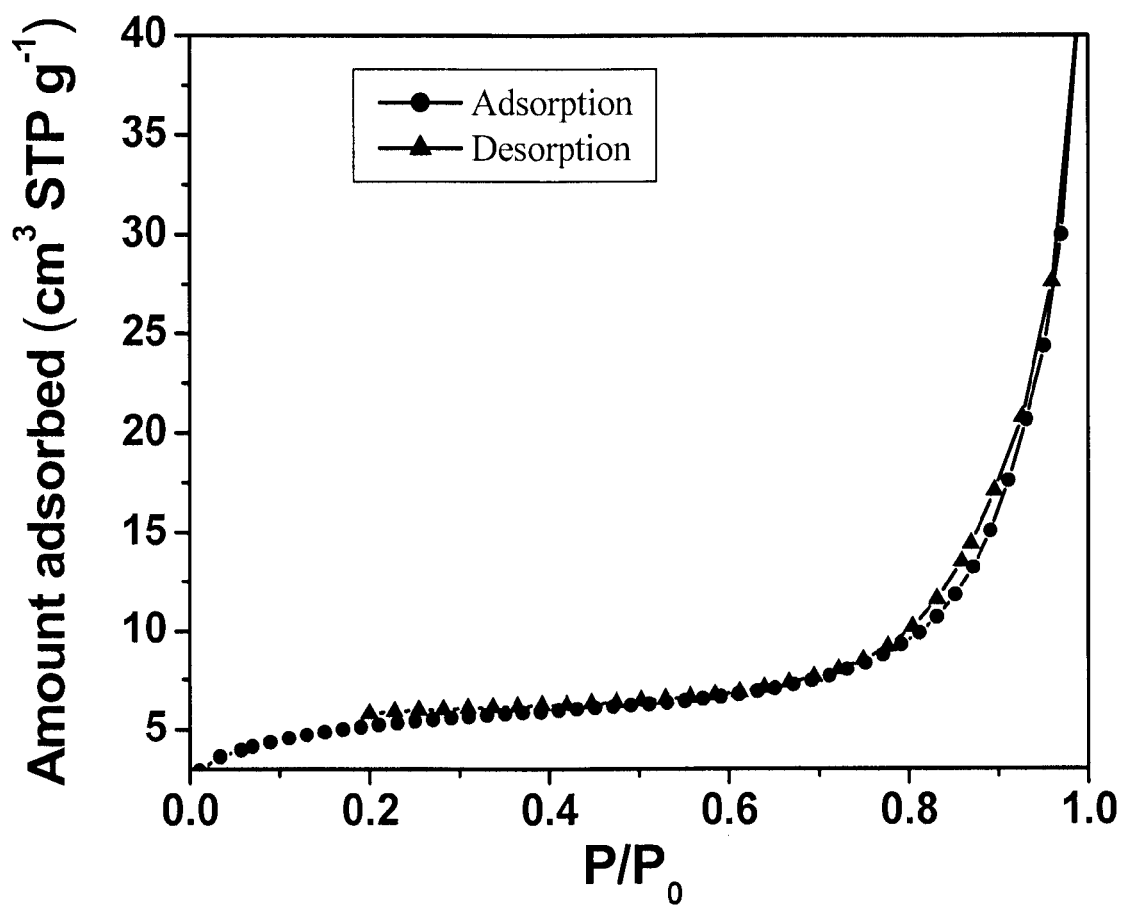

FIG. 17 provides nitrogen adsorption-desorption isotherms of $SiO_2$/Pd—NP/Porous-$SiO_2$ nanospheres that were etched for 100 minutes.

Figure 18:
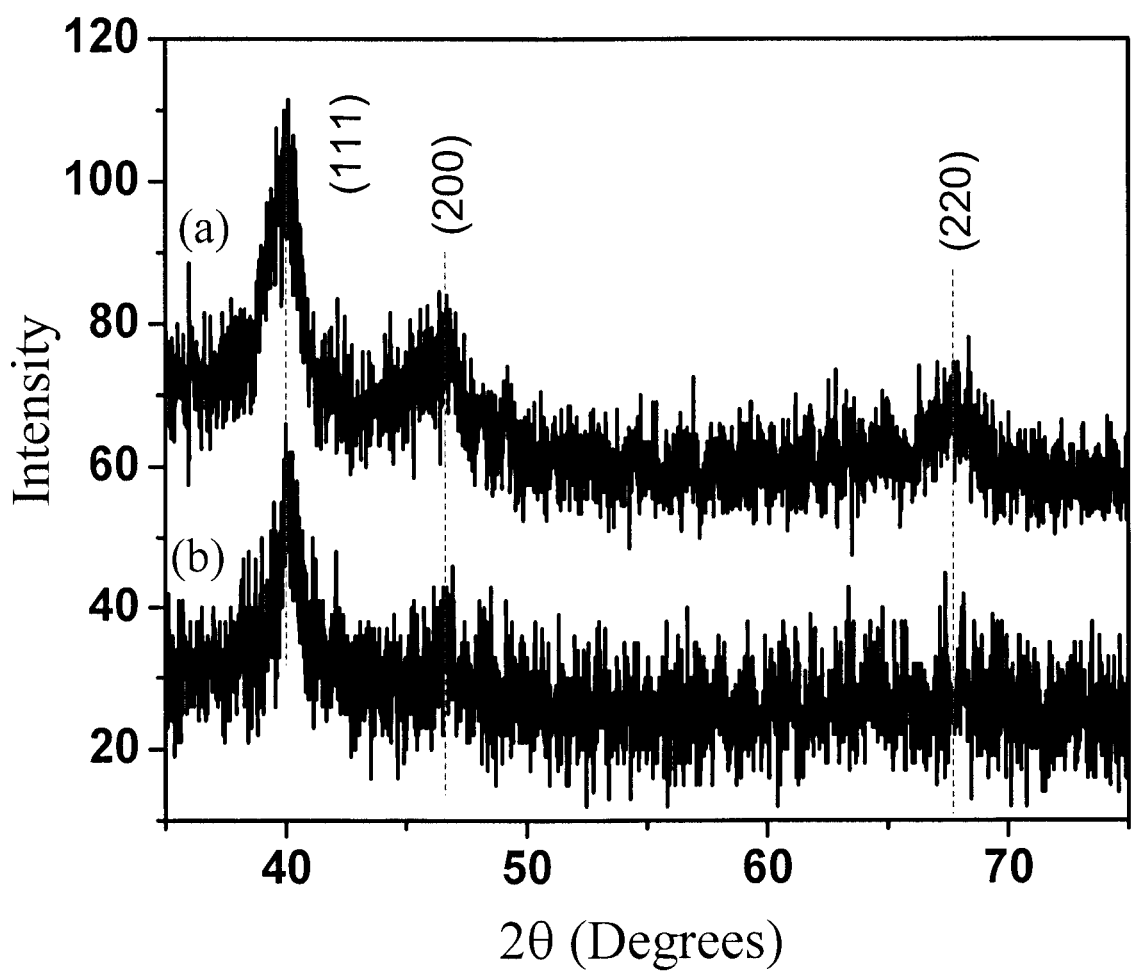

FIG. 18 provides powder XRD patterns of as-prepared $SiO_2$/Pd-NP core-shell nanospheres with 5 nm Pd-NP (line (a)) and $SiO_2$/Pd-NP/Porous-$SiO_2$ core-shell-shell nanospheres etched for 80 minutes with 5 nm Pd-NP (line (b)).

Figure 19:
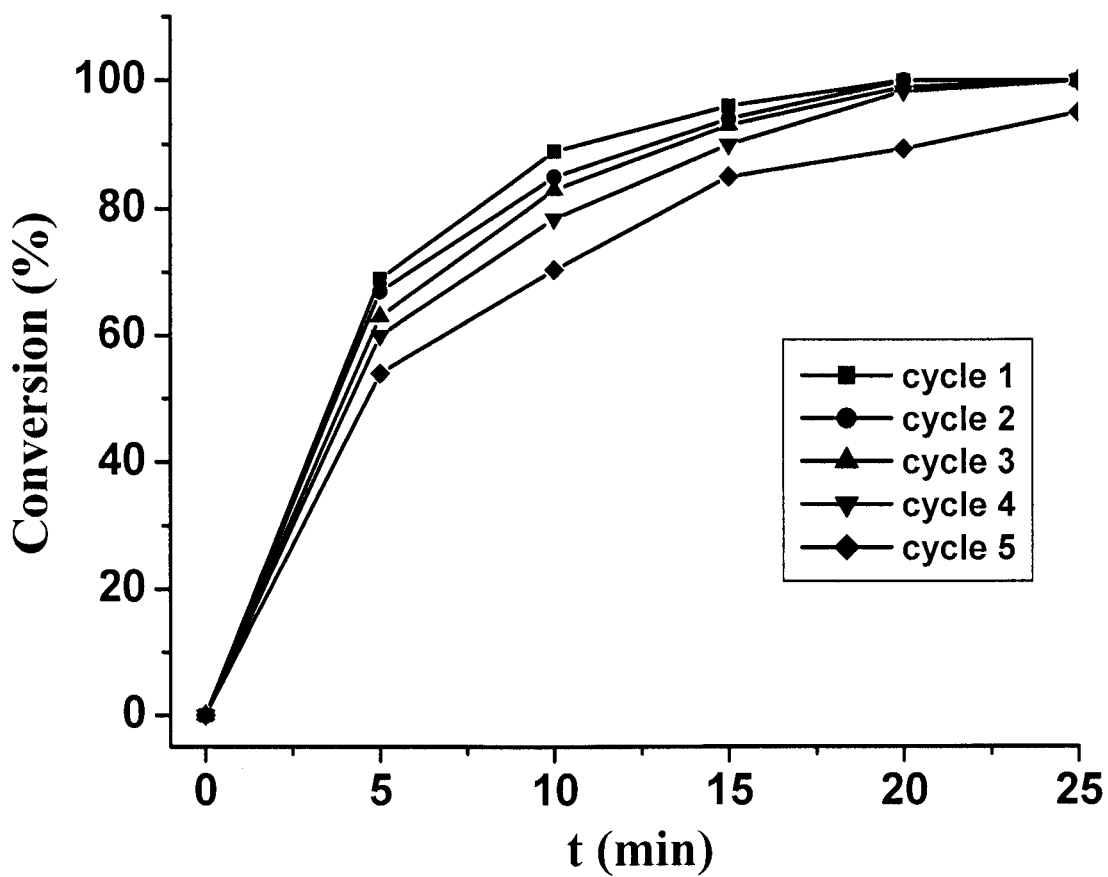

FIG. 19 provides a plot of conversion of styrene as a function of reaction time in five successive cycles of reaction using the etched $SiO_2$/Pd-NP/Porous-$SiO_2$ core-shell-shell nanosphere catalyst.

Figure 20:
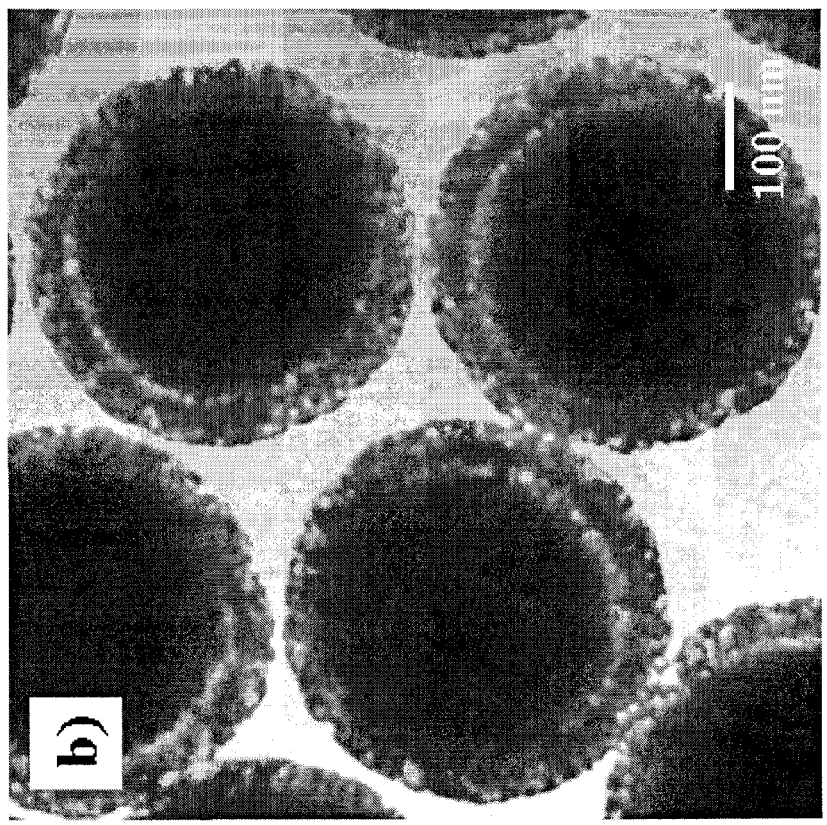
Figure 20:
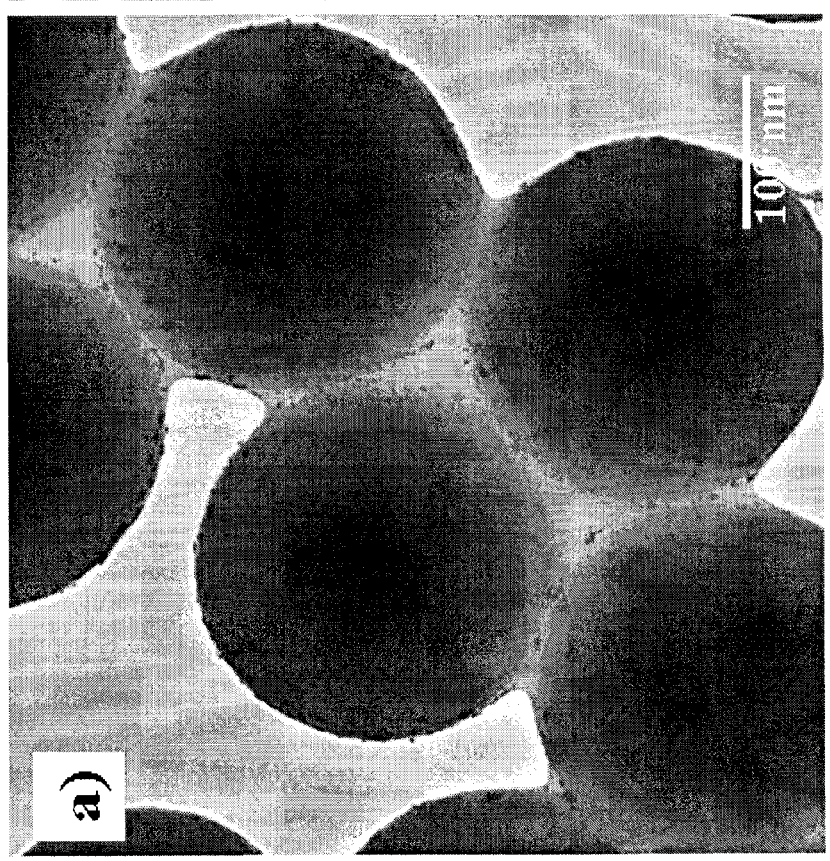

FIG. 20 provides TEM images of $SiO_2$/Pd-NP core-shell nanospheres (FIG. 20A) and $SiO_2$/Pd-NP/Porous-$SiO_2$ nanospheres after five cycles of catalysis in hydrogenation reaction (FIG. 20B).

Figure 21:
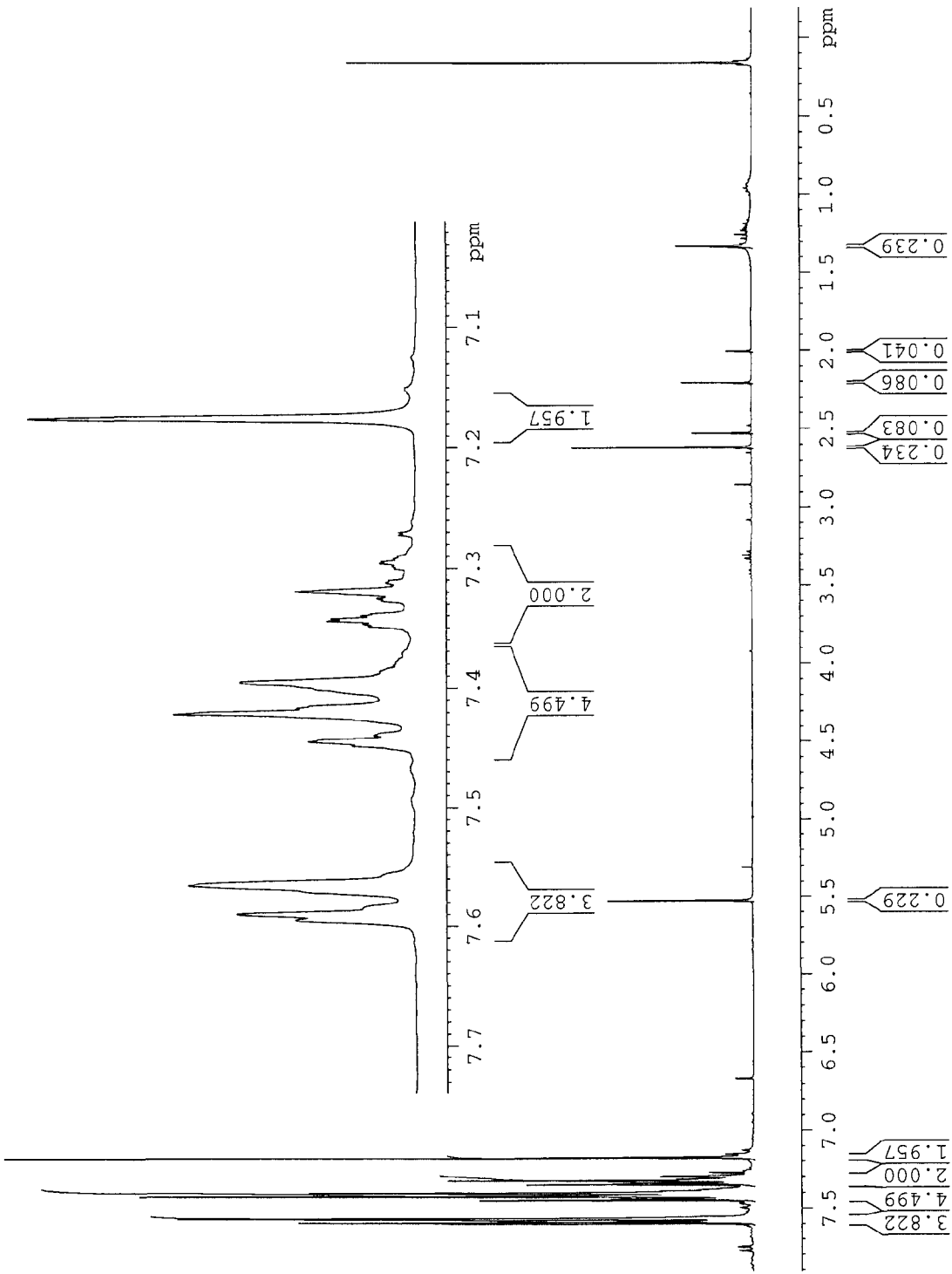

FIG. 21 provides the $^1H$ NMR spectra of the Heck coupling product of trans-stilbene by using $SiO_2$/Pd-NP/Porous-$SiO_2$ nanospheres as catalyst in the Heck coupling reaction between iodobenzene and styrene. The formation of trans-stilbene was monitored by GC-MS, GC and $^1H$ NMR. $^1H$ NMR ($CDCl_3$, 300 MHz): $\delta$ 7.60-7.55 (m, 4H), 7.45-7.37 (m, 4H), 7.35-7.29 (m, 2H), and 7.18 (s, 2H).

Figure 22:
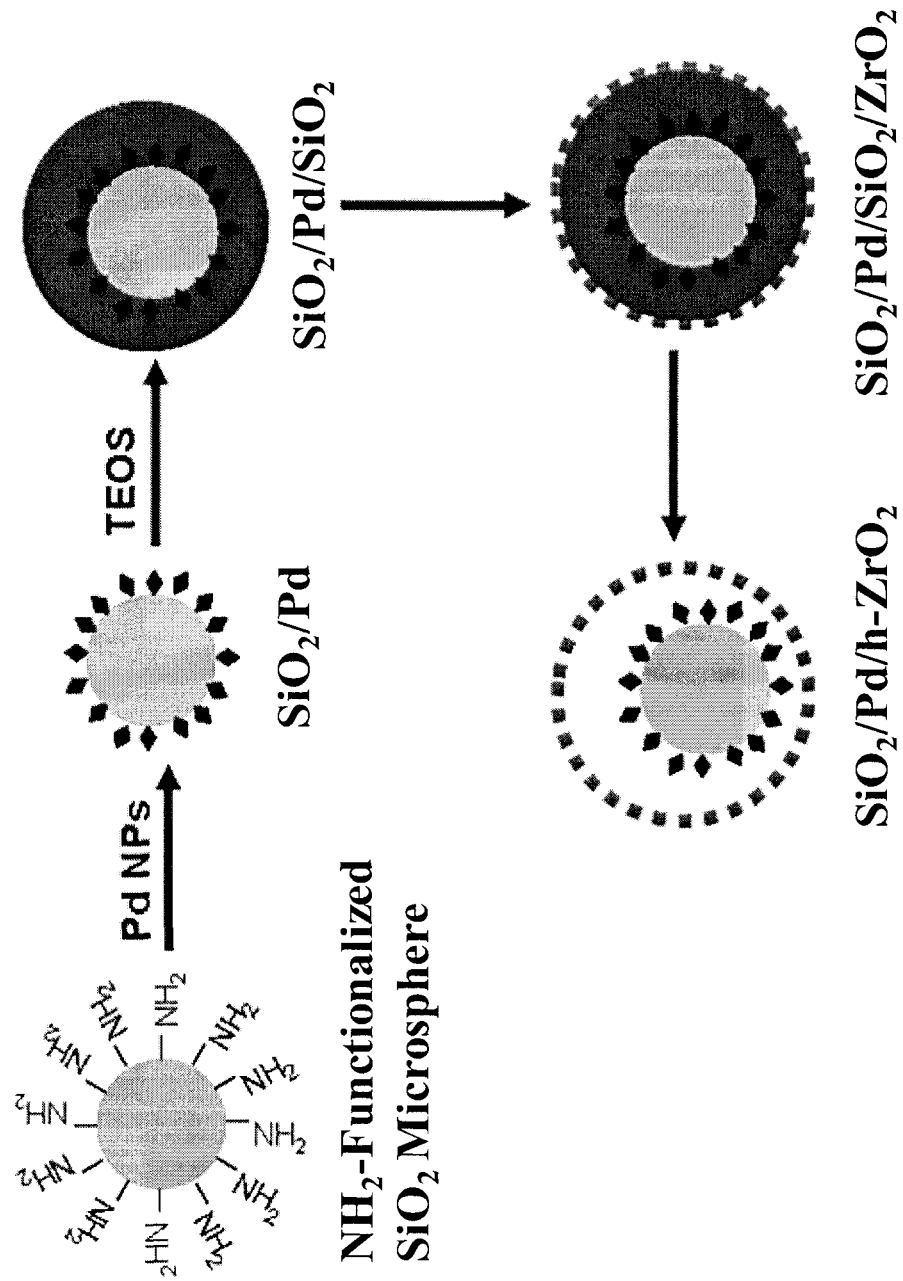

FIG. 22 provides a schematic representation of the synthesis of $SiO_2$/Pd/h-$ZrO_2$ core-shell-shell nanostructures. Premade shaped Pd nanoparticles are assembled on the surface of aminopropyl-functionalized $SiO_2$ microsphere cores, producing $SiO_2$/Pd core-shell microspheres. Then, by the sol-gel process, $SiO_2$ shell is coated over $SiO_2$/Pd core-shell microspheres, producing $SiO_2$/Pd/$SiO_2$ core-shell-shell microspheres. Deposition of $ZrO_2$ over $SiO_2$/Pd/$SiO_2$ core-shell-shell microspheres using Zr-butoxide results in $SiO_2$/Pd/$SiO_2$/$ZrO_2$ core-shell-shell-shell microspheres. Upon controlled etching of the inner $SiO_2$ shell of $SiO_2$/Pd/$SiO_2$/$ZrO_2$ microspheres using dilute aqueous NaOH solution, hollow $SiO_2$/Pd/h-$ZrO_2$ microspheres having different size hollow and nanoporous $ZrO_2$ shell are produced.

Figure 23:
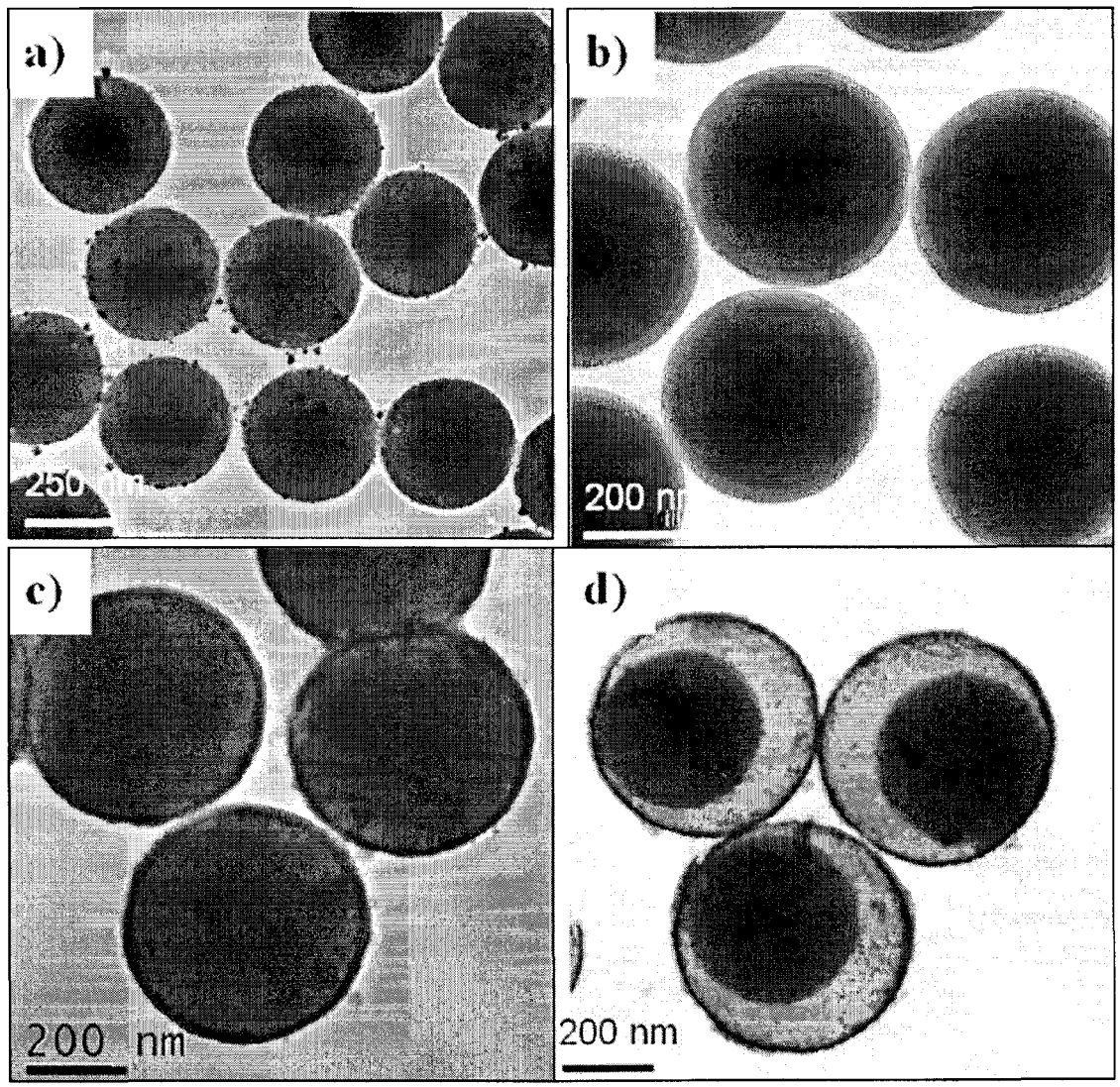

FIG. 23 provides representative low magnification TEM images of Pd nanoparticles (~5 nm) supported on aminopropyl-functionalized $SiO_2$ microspheres (or $SiO_2$/Pd core-shell microspheres) (FIG. 23A), $SiO_2$/Pd/$SiO_2$ core-shell-shell microspheres (FIG. 23B), $SiO_2$/Pd/$SiO_2$/$ZrO_2$ core-shell-shell-shell microspheres (FIG. 23C), and hollow $SiO_2$/Pd/h-$ZrO_2$ core-shell-shell microspheres (FIG. 23D). The hollow $SiO_2$/Pd/h-$ZrO_2$ core-shell-shell microspheres are resulted from calcination of the Brij 30 surfactant in $ZrO_2$, followed by etching of the inner $SiO_2$ shell, of the $SiO_2$/Pd/$SiO_2$/$ZrO_2$ core-shell-shell-shell microspheres.

Figure 24:
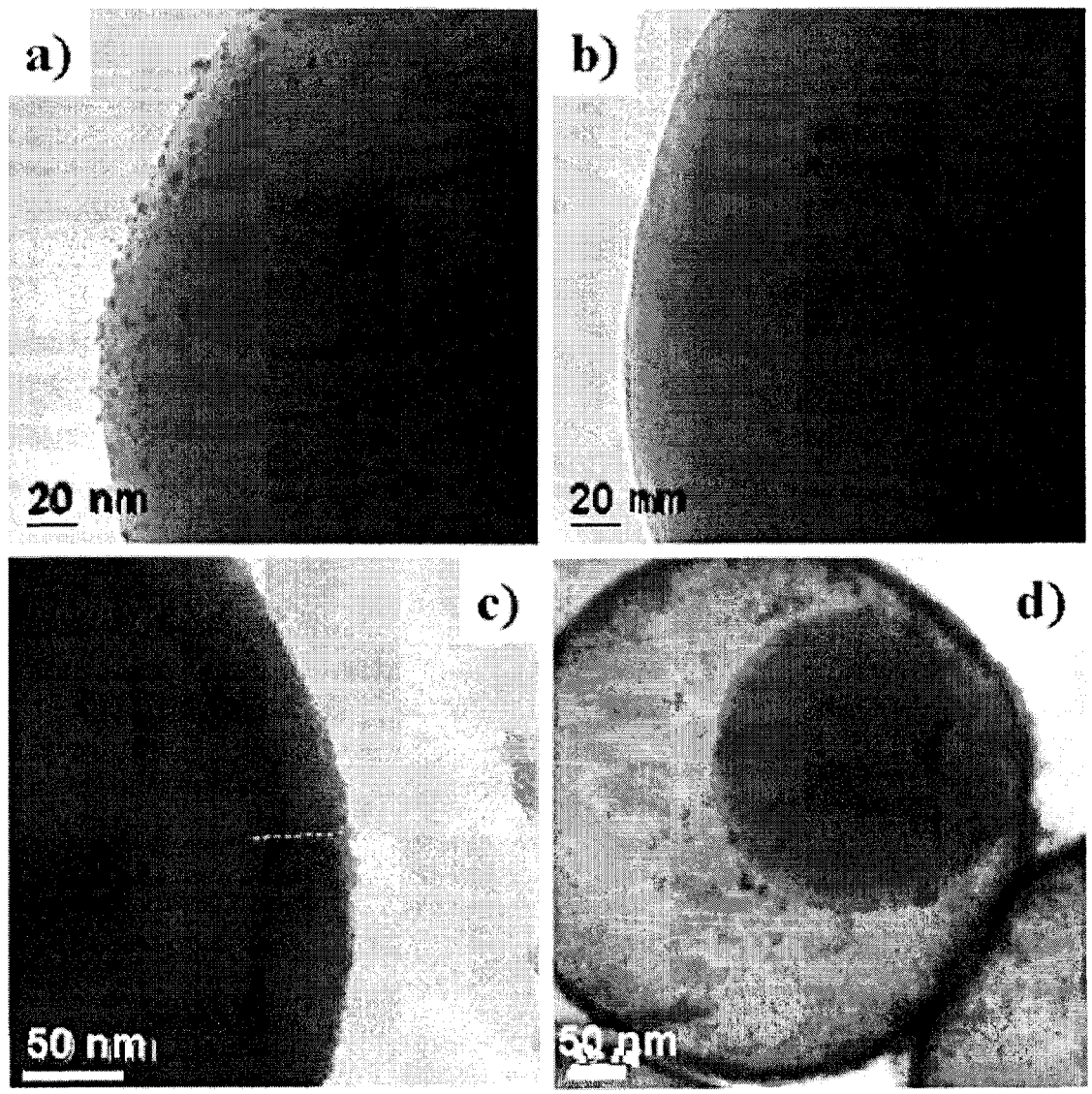

FIG. 24 provides representative high magnification TEM images for samples shown in FIG. 23, which includes Pd nanoparticles (~5 nm) supported on aminopropyl-functionalized $SiO_2$ microspheres, producing $SiO_2$/Pd core-shell microspheres (FIG. 24A), $SiO_2$/Pd/$SiO_2$ core-shell-shell microspheres (FIG. 24B), $SiO_2$/Pd/$SiO_2$/$ZrO_2$ core-shell-shell-shell microspheres (FIG. 24C) and hollow $SiO_2$/Pd/h-$ZrO_2$ core-shell-shell microspheres (FIG. 24D).

Figure 25:
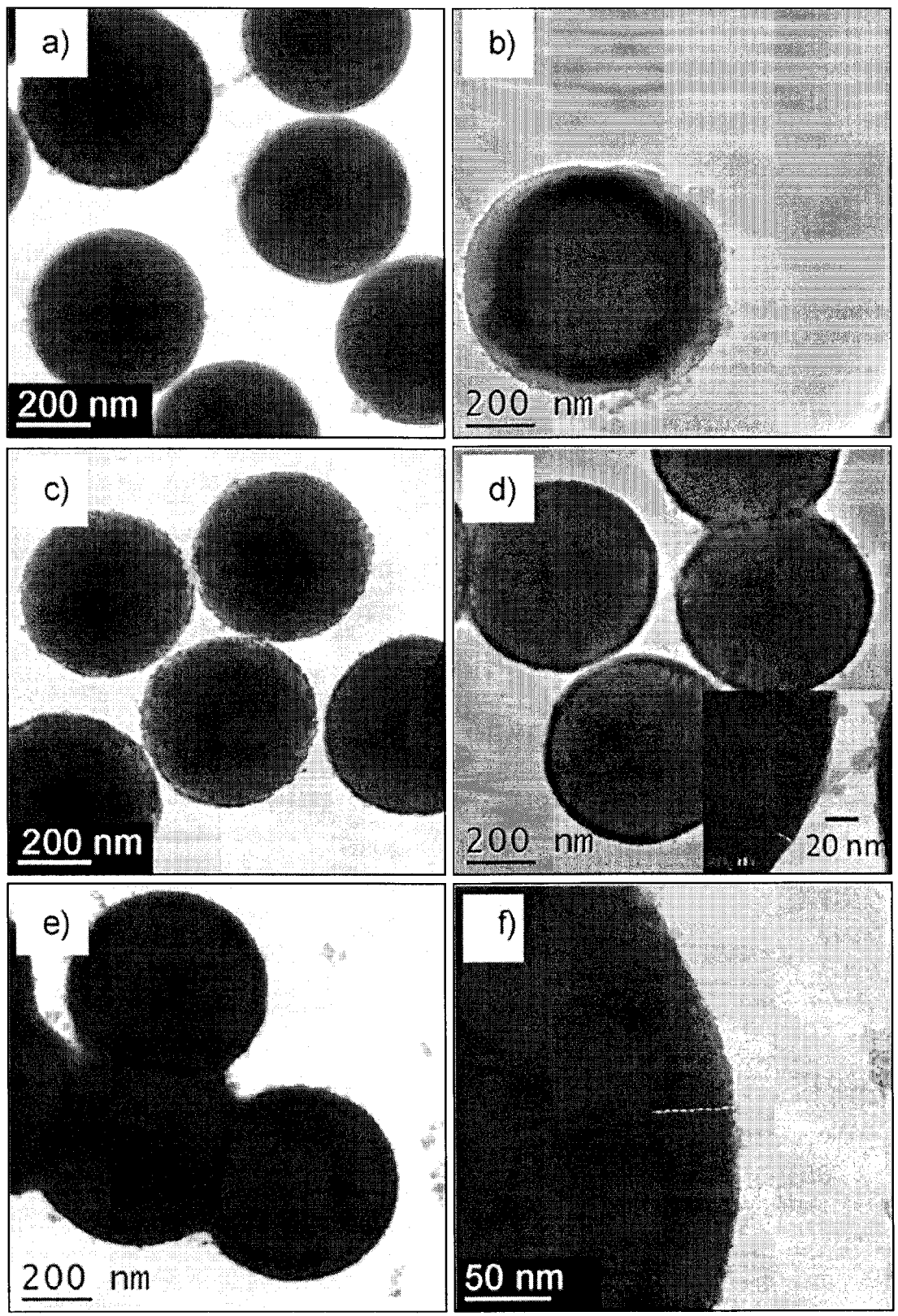

FIG. 25 provides TEM images showing the effect of the amount of $Zr(OBu)_4$ on the thickness of the $ZrO_2$ shell forming around the given amount of $SiO_2$/Pd/$SiO_2$ core-shell-shell microspheres. FIG. 25A: 0.2 mL, FIG. 25B: 1 mL, FIG. 25C:

0.4 mL, FIG. 25D: 0.45 mL, and FIG. 25E: 0.5 mL Zr(OBu)$_4$. The inset within FIG. 25D and FIG. 25F show an enlarged image of the ZrO$_2$ shell and its size.

Figure 26:
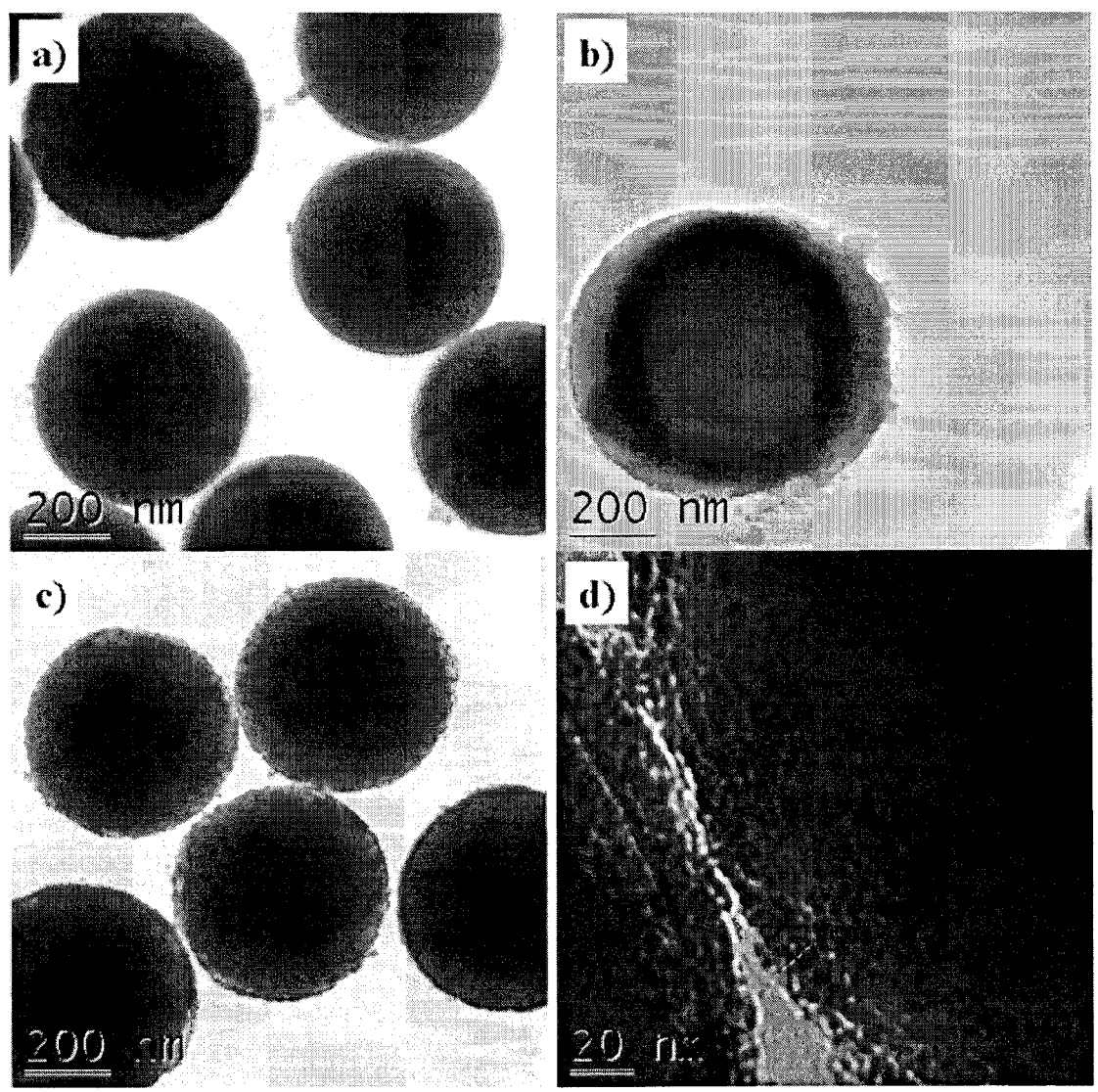
Figure 26:
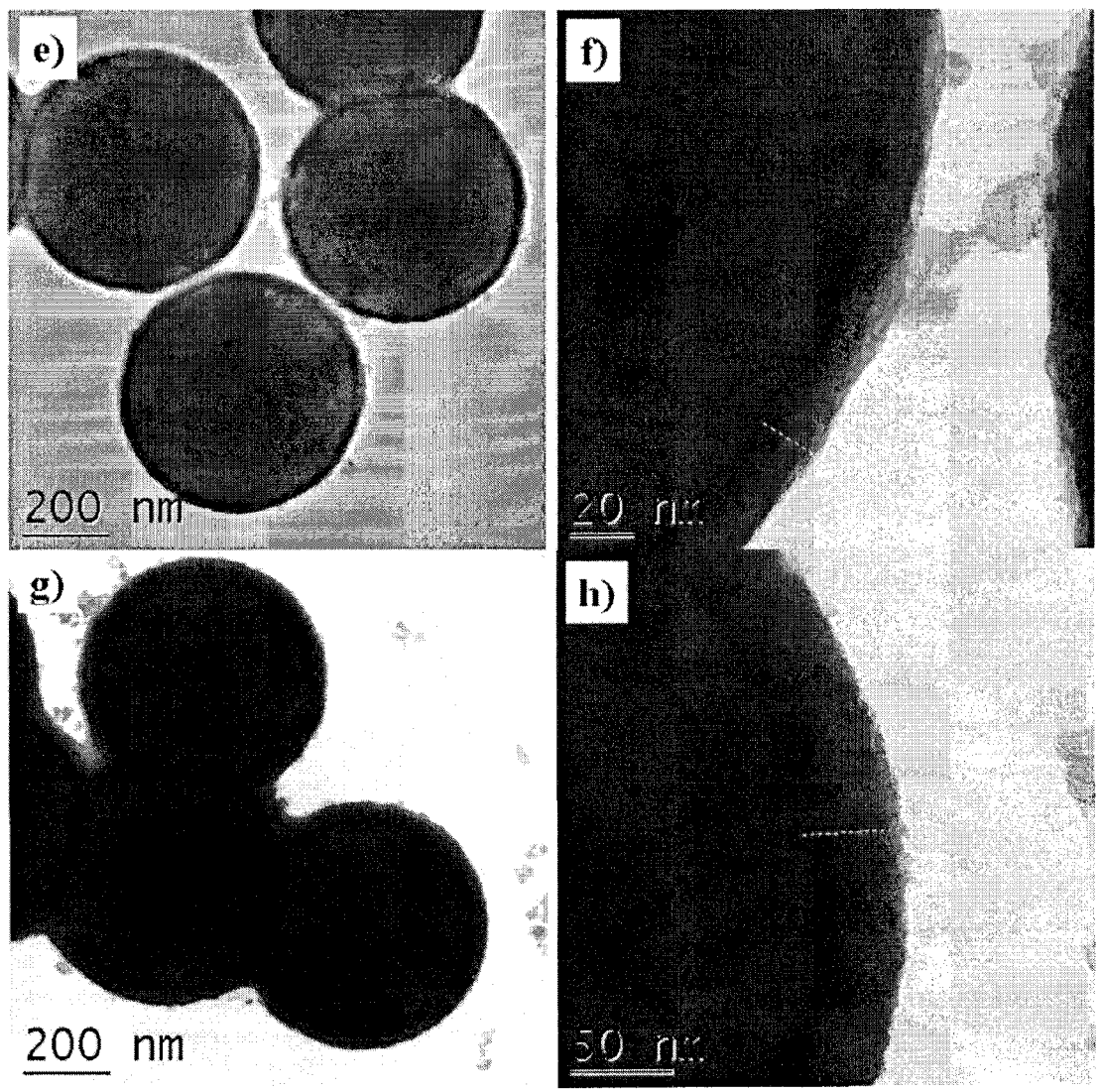

FIG. 26 provides Enlarged representative TEM images of SiO$_2$/Pd/SiO$_2$/ZrO$_2$ core-shell-shell-shell microspheres possessing different thickness of ZrO$_2$ shell made by using different amounts of Zr(OBu)$_4$: FIG. 26A: 0.2 mL Zr(OBu)$_4$, FIG. 26B: 1 mL Zr(OBu)$_4$, FIGS. 26C and 26D: 0.4 mL Zr(OBu)$_4$, FIGS. 26E and 26F: 0.45 mL Zr(OBu)$_4$ and FIGS. 26G and 26H: 0.5 mL Zr(OBu)$_4$ for a given amount of SiO$_2$/Pd/SiO$_2$ core-shell-shell microspheres.

Figure 27:
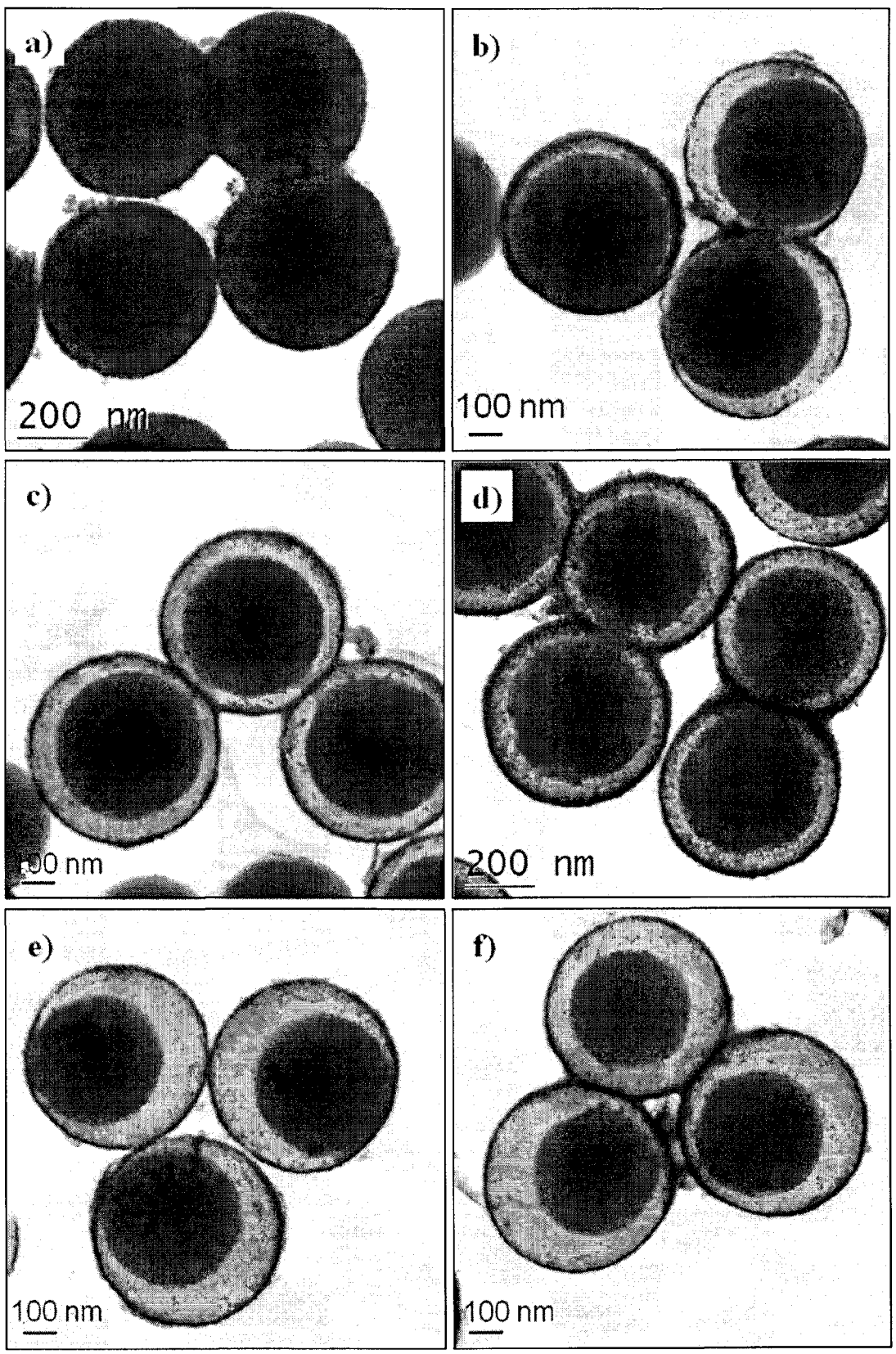
Figure 27:
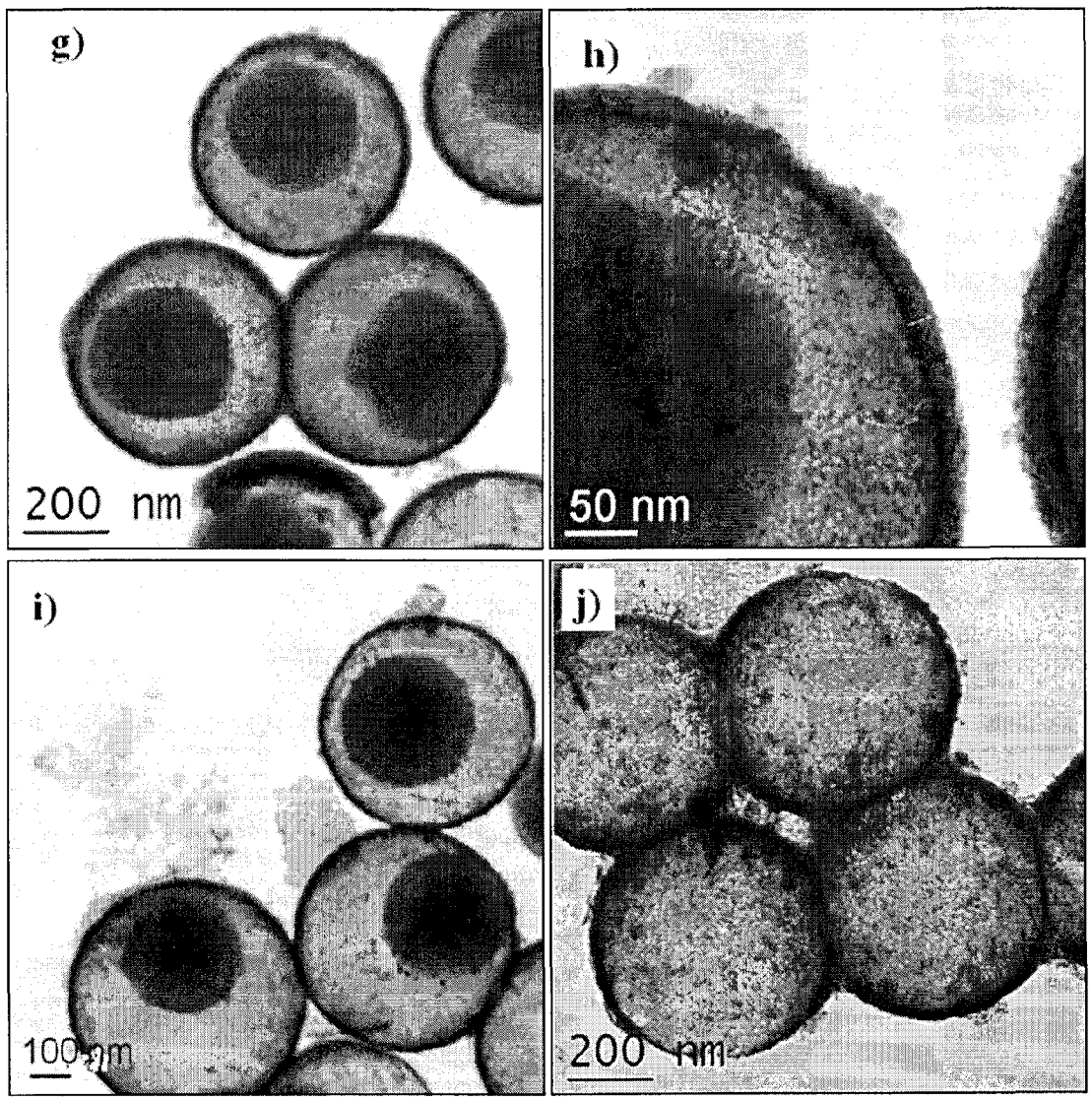

FIG. 27 provides TEM images showing the structural evolution of etched SiO$_2$/Pd/SiO$_2$/ZrO$_2$ core-shell-shell-shell microsphere, after etching with dilute NaOH solution for different etching times: FIG. 27A: 2 hours; FIG. 27B: 6 hours; FIG. 27C: 9 hours; FIG. 27D: 12 hours; FIG. 27E: 15 hours; FIG. 27F: 20 hours; FIGS. 27G and 27H: 24 hours; FIG. 27I: 27 hours; and FIG. 27J: 48 hours.

Figure 28:
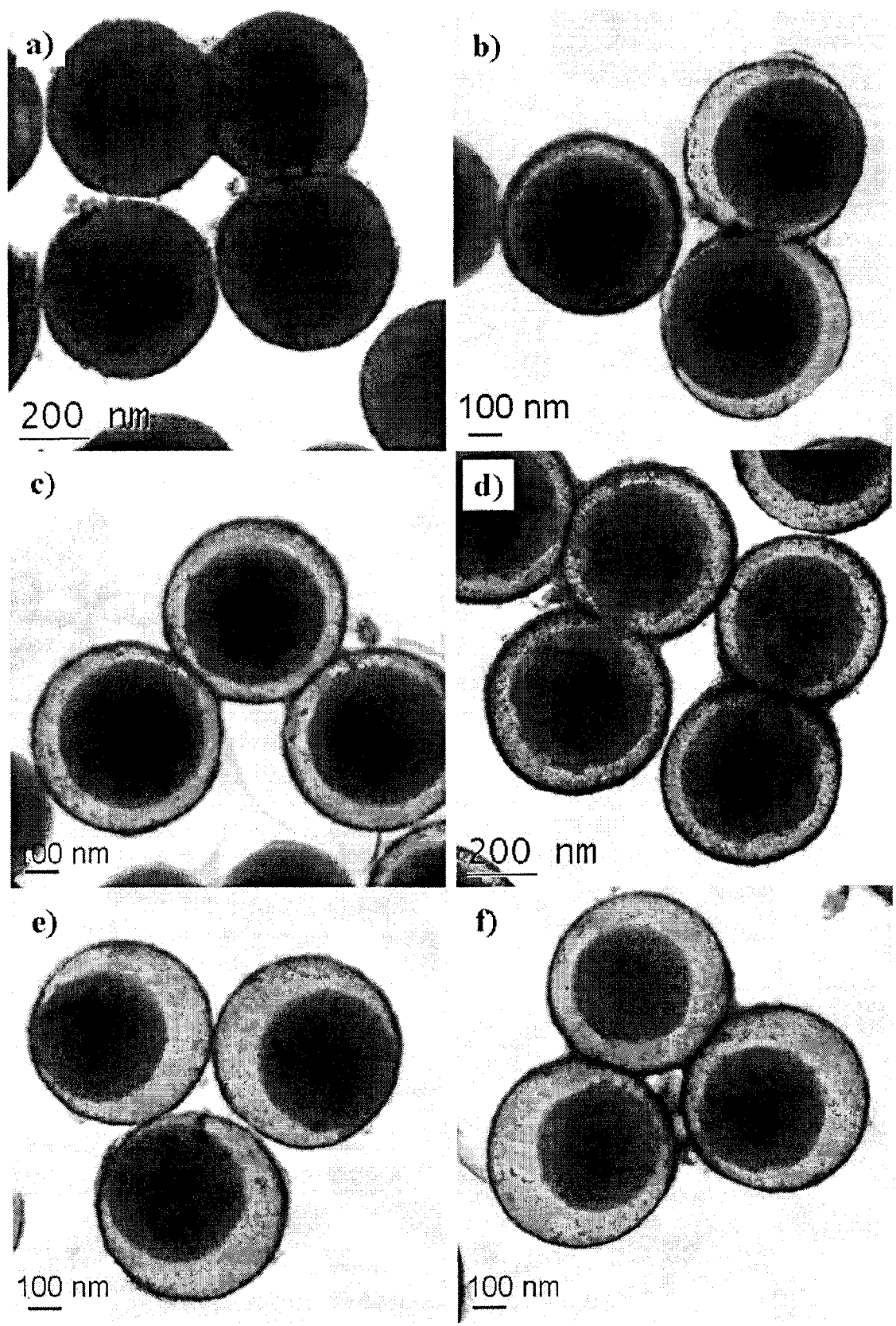
Figure 28:
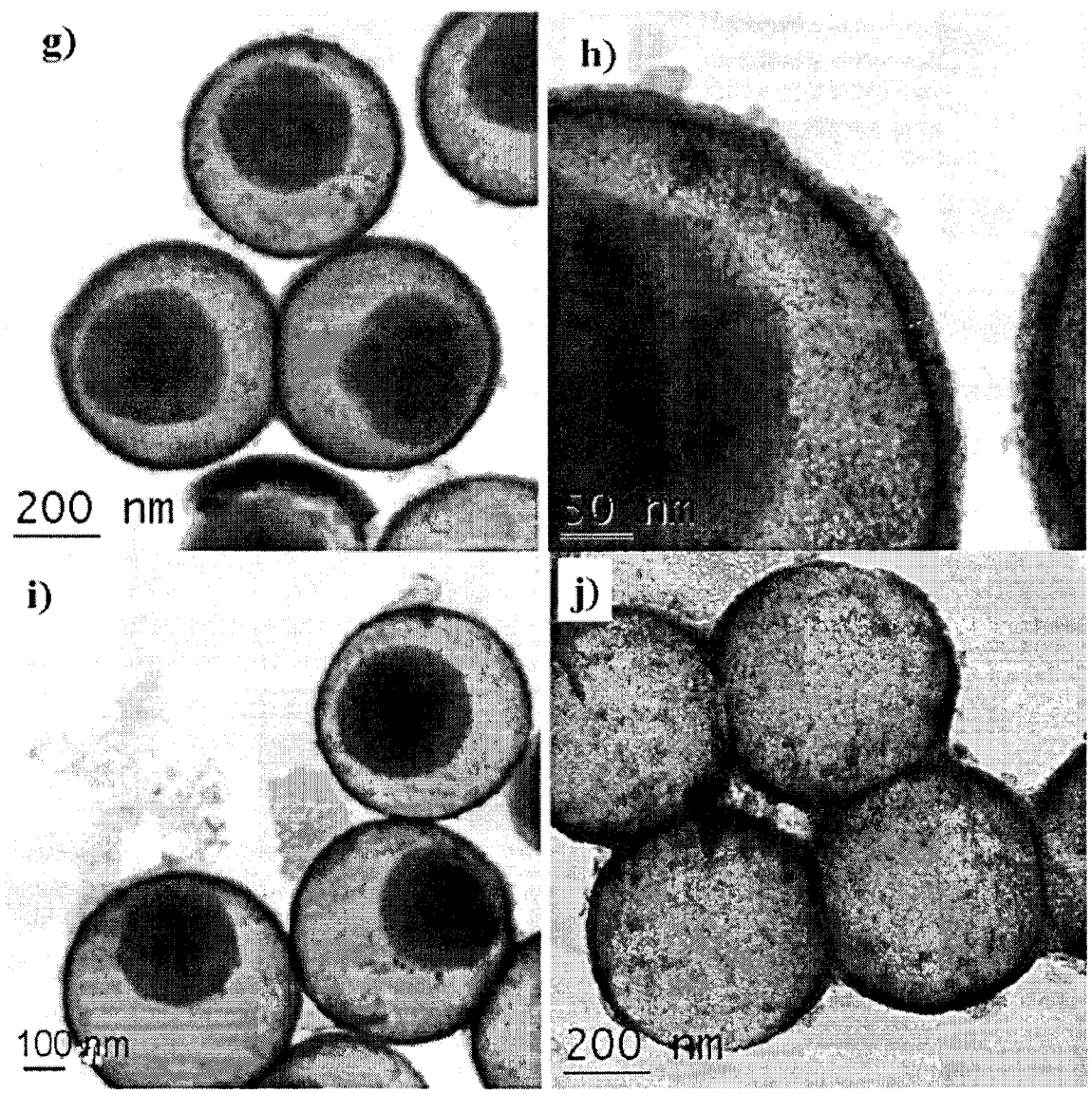

FIG. 28 provides highly magnified TEM images showing the structural evolution of etched SiO$_2$/Pd/SiO$_2$/ZrO$_2$ core-shell-shell microspheres, after etching with dilute NaOH solution for different etching times: FIG. 28A: 2 hours; FIG. 28B: 6 hours; FIG. 28C: 9 hours; FIG. 28D: 12 hours; FIG. 28E: 15 hours; FIG. 28F: 20 hours; FIGS. 28G and 28H: 24 hours; FIG. 28I: 27 hours; and FIG. 28J: 48 hours.

Figure 29:
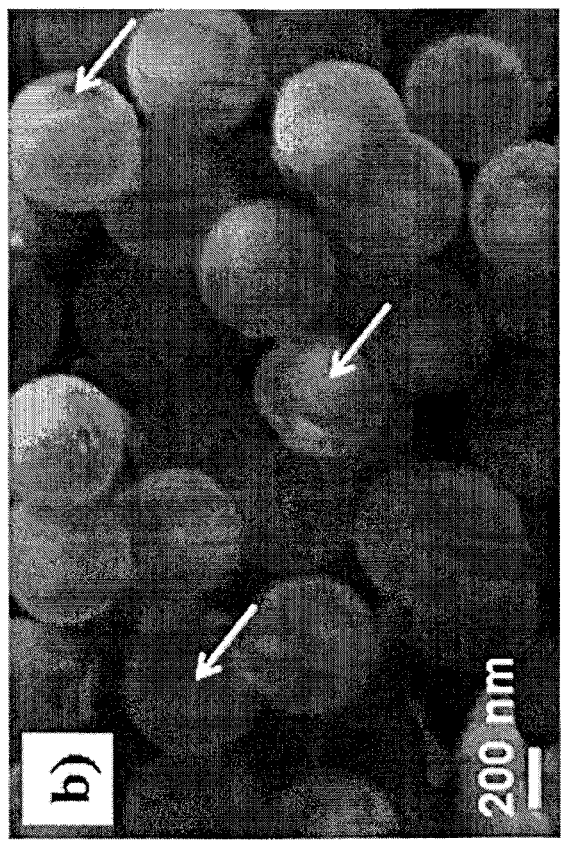
Figure 29:
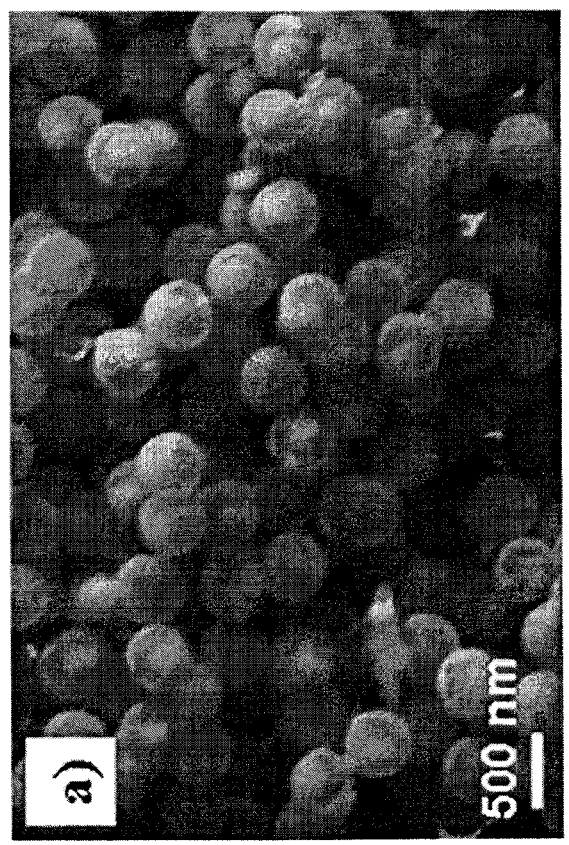

FIG. 29 provides SEM images of hollow SiO$_2$/Pd/h-ZrO$_2$ core-shell-shell microspheres prepared from SiO$_2$/Pd/SiO$_2$/ZrO$_2$ core-shell-shell-shell microsphere after etching in dilute NaOH solution for 24 hours. The arrows indicate partially broken SiO$_2$/Pd/h-ZrO$_2$ core-shell-shell microspheres.

Figure 30A:
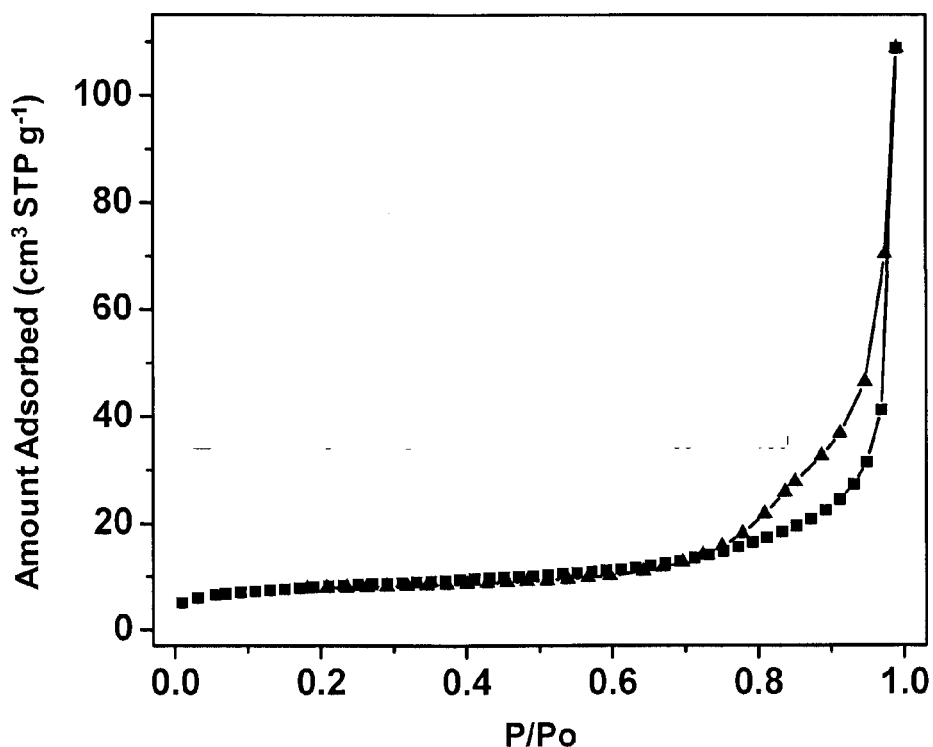
Figure 30B:
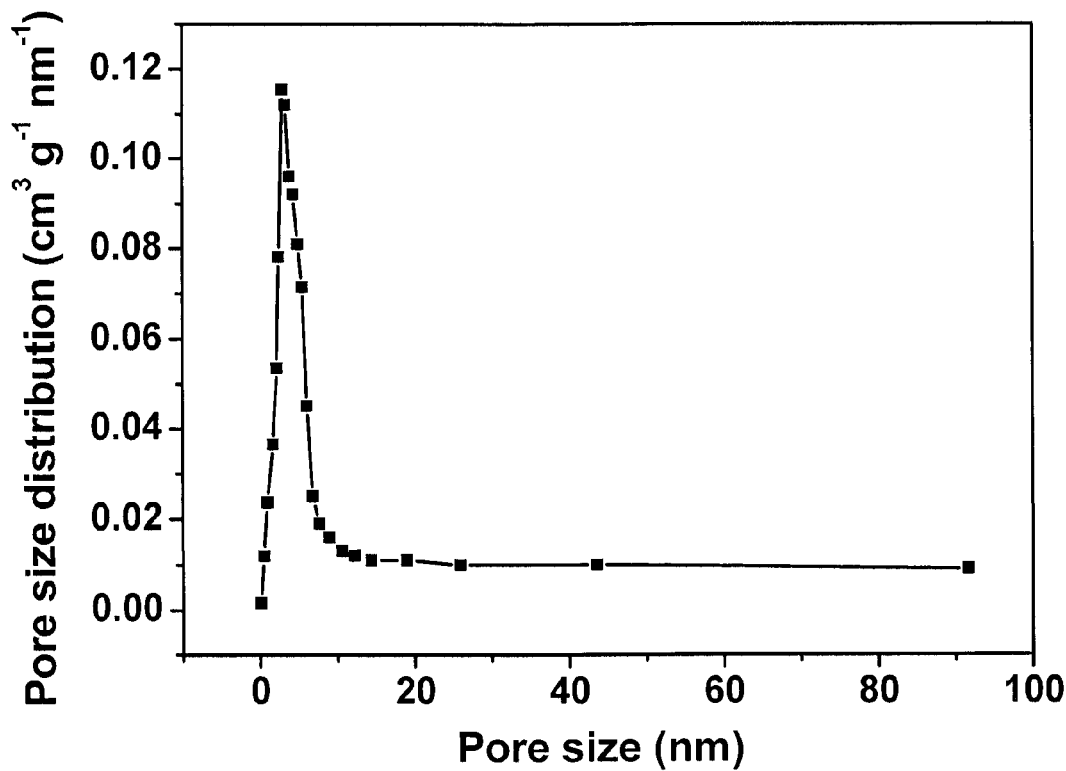

FIG. 30A provides nitrogen adsorption/desorption isotherms of hollow SiO$_2$/Pd/h-ZrO$_2$ core-shell-shell microspheres and FIG. 30B provides pore size distribution in the nanoporous ZrO$_2$ shell of the material.

Figure 31:
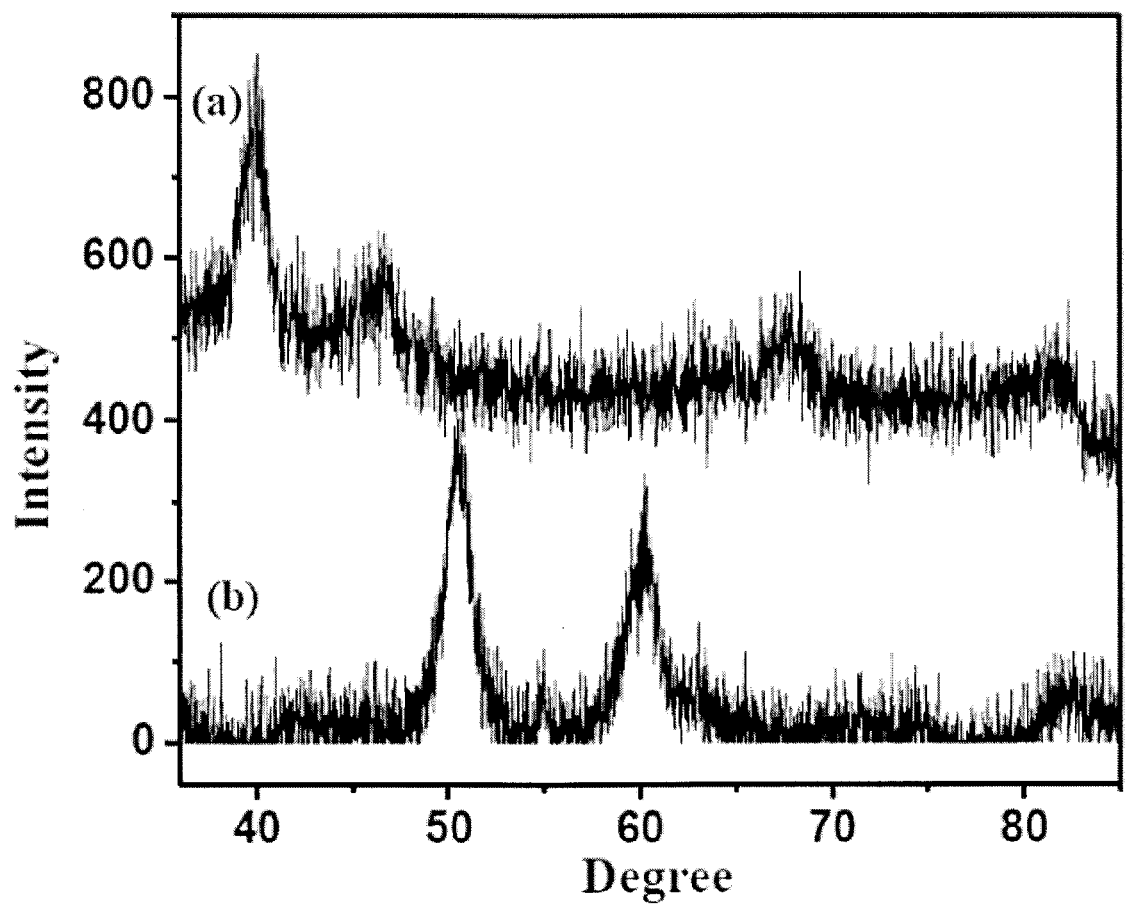

FIG. 31 provides powder XRD patterns of the as-prepared SiO$_2$/Pd core-shell microspheres (FIG. 31A) and SiO$_2$/Pd/h-ZrO$_2$ core-shell-shell microspheres (FIG. 31B).

Figure 32:
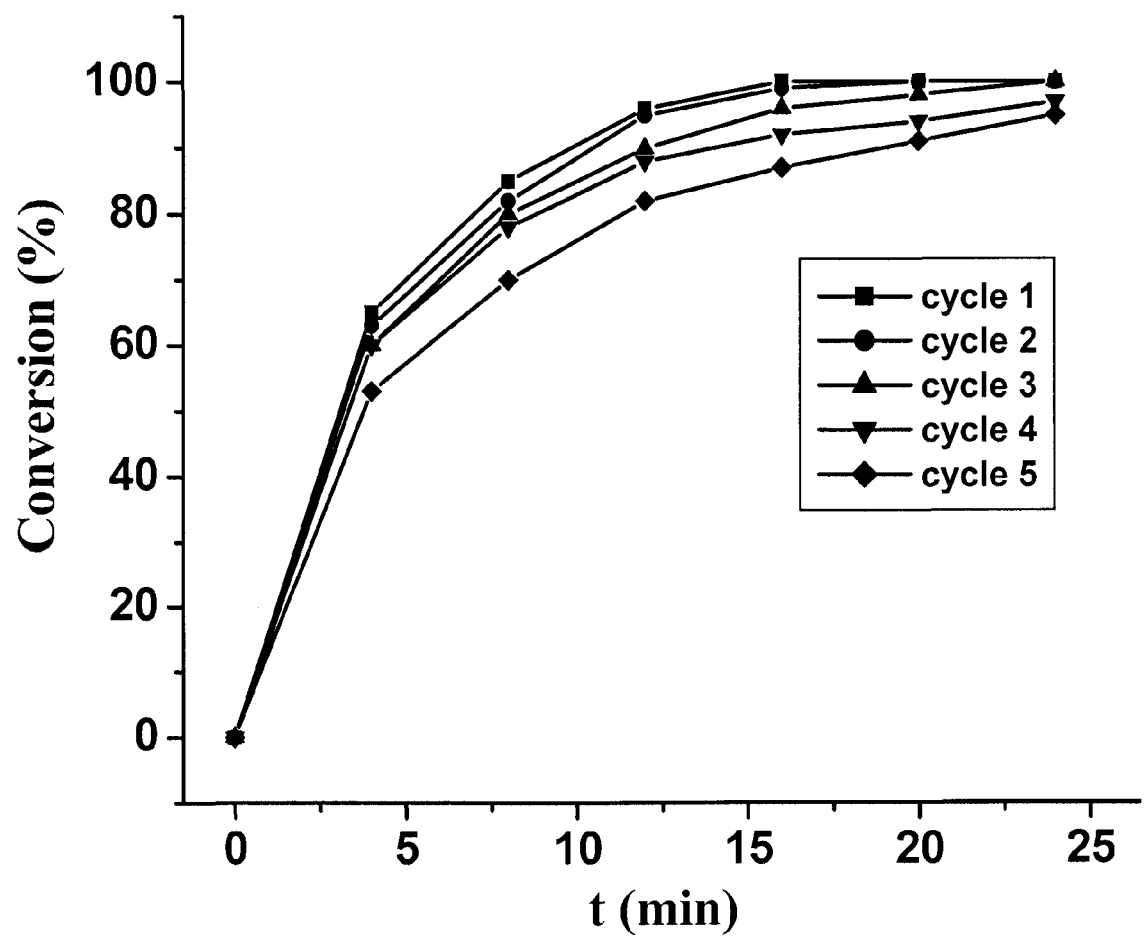

FIG. 32 provides a plot of % conversion of styrene versus reaction time for five successive cycles of catalytic hydrogenation reactions using SiO$_2$/Pd/h-ZrO$_2$ core-shell-shell microspheres as catalysts.

Figure 33:
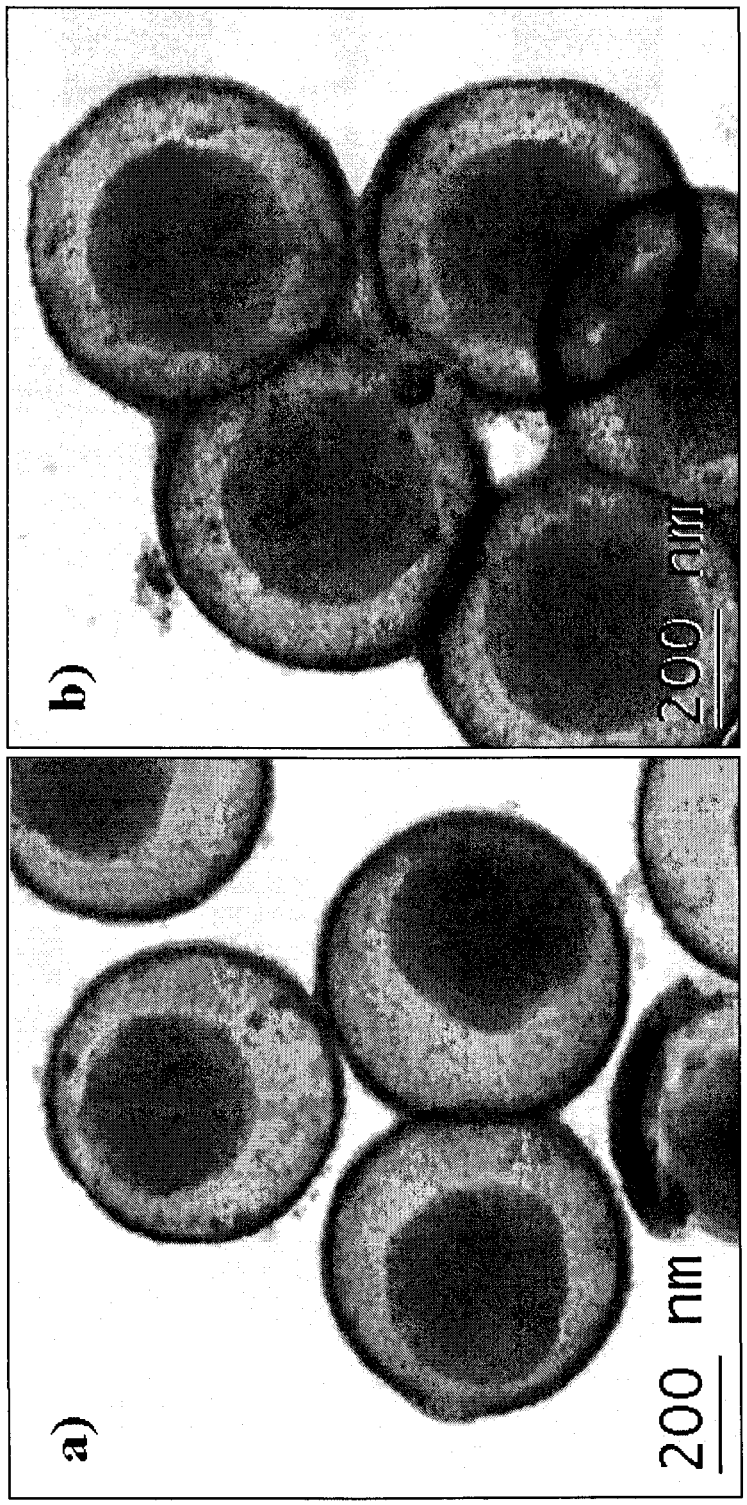

FIG. 33 provides TEM images of SiO$_2$/Pd/h-ZrO$_2$ core-shell-shell microspheres before (FIG. 33A) and after five cycles of catalysis (FIG. 33B).

DETAILED DESCRIPTION OF THE INVENTION

The instant invention provides nanoparticles that with unexpectedly superior properties. The nanoparticles provided herein are efficient catalysts that are recyclable without the loss of catalytic activity. The nanoparticles and methods of synthesis are described in more detail hereinbelow. While the nanoparticles are described herein with a silicon dioxide (SiO$_2$) core, the instant invention encompasses nanoparticles with other metal oxide cores, such as titania, alumina, and the like. Further, the terms nanoparticle, nanosphere, microsphere, and nanostructure are used interchangeably throughout the application. Typically, the nanoparticles of the instant invention have a diameter of less than 1000 nm, particularly less than 500 nm. Compositions comprising at least one nanoparticle of the instant invention and at least one carrier are also encompassed by the instant invention.

The instant invention also encompasses methods of catalyzing a chemical reaction with the catalyst containing nanoparticles described herein. The nanoparticles may be used to catalyze, for example, hydrogenation reactions, Heck coupling reactions, and the like. Furthermore, based on the excellent recyclable properties of the nanoparticles of the instant invention, methods comprising multiple rounds of chemical reactions without the need to replace or re-charge the catalyst are encompassed herein.

I. Silica-Dendrimer Core-Shell Microspheres

The synthesis, characterization, and catalytic properties of novel monodisperse SiO$_2$@Pd-PAMAM core-shell microspheres containing SiO$_2$ microsphere cores and PAMAM dendrimer-encapsulated Pd nanoparticle (Pd-PAMAM) shells is described herein. Briefly, SiO$_2$ microspheres were functionalized with vinyl groups by grafting their surfaces with vinyltriethoxysilane (VTS). The vinyl groups were then converted into epoxides by using m-chloroperoxybenzoic acid. Upon treatment with amine-terminated G4 poly(amidoamine) (PAMAM) dendrimers, the SiO$_2$-supported epoxides underwent ring-opening and gave SiO$_2$@PAMAM core-shell microspheres. Pd nanoparticles within the cores of the SiO$_2$-supported PAMAM dendrimers were synthesized by letting Pd(II) ions complex with the amine groups in the cores of the dendrimers and then reducing them into Pd(0) with NaBH$_4$. This produced the SiO$_2$@Pd-PAMAM core-shell microspheres. The presence of the different functional groups on the materials was monitored by following the changes in FTIR spectra, elemental analyses, and weight losses on thermogravimetric traces. Transmission electron microscopy (TEM) images showed the presence of Pd nanoparticles with average size of 1.56±0.67 nm on the surface of the monodisperse SiO2@Pd-PAMAM core-shell microspheres. The SiO$_2$@Pd-PAMAM core-shell microspheres were successfully used as an easily recyclable catalyst for hydrogenation of various olefins, alkynes, keto, and nitro groups, giving ~100% conversion and high turnover numbers (TONs) under 10 bar H$_2$ pressure, at room temperature and in times ranging from 10 minutes to 3 hours. In addition, the SiO$_2$@Pd-PAMAM core-shell microspheres were proven to be recyclable catalysts up to five times with barely any leaching of palladium into the reaction mixture.

The degree of passivation of the surface of metallic nanoparticles can become more optimized for catalysis with dendrimers as stabilizing agents. This is because the branching and porous structures of dendrimers will inhibit them from forming a well-packed self-assembled monolayer (SAM)-like structure that alkanethiol and alkylamine groups typically form around the metallic nanoparticles. Thus, dendrimer-encapsulated metallic nanoparticles can exhibit better catalytic activities compared to other types of ligand-stabilized nanoparticles.

Dendrimers have indeed been successfully used to stabilize a number of MNPs including PdNPs (Zhao et al. (1998) J. Am. Chem. Soc., 120:4877-4878; Zhao et al. (1999) Angew. Chem., Int. Ed., 38:364-366; Balogh et al. (1998) J. Am. Chem. Soc., 120:7355-7356; Esumi et al. (1998) Langmuir 14:3157-3159; Scott et al. (2003) Chem. Mater., 15:3873-3878). Furthermore, the resulting dendrimer-encapsulated nanoparticles (DENs) were shown to have various applications in sensing, molecular electronics, photonics, and nanomedicine (Astruc et al. (2005) Angew. Chem., Int. Ed., 44:7852-7872; Crooks et al. (2001) Acc. Chem. Res., 34:181-190; Kuhn et al. (2008) J. Am. Chem. Soc., 130:14026-14027; Balogh et al. (2001) Nano Lett., 1:18-21; Astruc et al. (2010) Chem. Rev., 110:1857-1959). In addition, DENs consisting of transition metal nanoparticles within their cores were shown to serve as stable nanocatalysts (Zhao et al. (1999) Angew. Chem., Int. Ed., 38:364-366). DEN catalysts, also known as dendrimer-encapsulated catalysts (DECs), have branching structures that allow reactants to diffuse in and reach the entrapped nanoparticle catalytic sites while at the same time stabilize the nanoparticles from aggregation. For instance, the synthesis and catalytic properties of PAMAM dendron-stabilized PdNPs for hydrogenation of dienes and acetylenes to monoenes has recently been demonstrated (Mizugaki et al. (2008) Chem. Commun., 2:241-243). In another example, triethoxybenzamide-terminated poly(propyleneimine) (PPI) dendrimer-stabilized PdNPs were synthesized and used as substrate specific catalysts for hydrogenation reactions (Ooe et al. (2002) Nano Lett., 2:999-1002).

Although the synthesis and catalytic activities of various DECs have been successfully demonstrated, dendrimers, even those with many generations, are relatively too small to easily separate from solutions and reuse after catalytic reactions—a feature that is often sought for "true" heterogeneous catalysts (Iwasawa et al. (2004) J. Am. Chem. Soc., 126: 6554-6555). Thus, research in the past several years has also focused on developing easier ways for recycling DECs. Solvent precipitation and membrane filtration were among the common methods considered to separate and recycle DECs; however, they were shown to result in some losses of the materials as well as their catalytic activities (Mizugaki et al. (1999) J. Mol. Catal. A: Chem., 145:329-333; de Groot et al. (2001) J. Am. Chem. Soc., 123:8453-8458; Eggeling et al. (2000) J. Org. Chem., 65:8857-8865). Surface modification of the surfaces of DECs by multi-step chemical reactions in order to tune the DECs' solubility and help their separation from solutions have also been reported (Frechet et al., Eds. Dendrimers and Other Dendritic Polymers; J. Wiley & Sons: New York, 2001; Ooe et al. (2004) J. Am. Chem. Soc., 126: 1604-1605). Similarly, dialysis was used to separate dendrimers from solutions (Niu et al. (2001) J. Am. Chem. Soc., 123:6840-6846). However, both surface modification and dialysis involve time-intensive processes and relatively costly reagents and membranes. Although separation of dendrimers by electrophoresis and chromatography is also possible, it is complicated by interaction of dendrimers with the stationary support materials, leading to the retention and incomplete separation of the dendrimers (Sedlakova et al. (2006) J. Chromatogr., B, 841:135-139). Additionally, selective solution phase extraction was used to separate a mixture of DENs containing Ag and Au nanoparticles from each other from an aqueous solution (Wilson et al. (2004) Chem. Mater., 16:4202-4204). Similarly, the separation of different generations (G1-G9) of amino-, acetamide-, hydroxyl-, and carboxylate-terminated dendrimers has been reported using reversed-phase HPLC (Islam et al. (2005) Anal. Chem., 77:2063-2070). Although these methods separate a mixture of two or more types of dendrimers (or DENs), analyzing them as well as extracting the entrapped MNPs from within the DENs, the methods have limited applications for recycling DECs in catalysis.

Thus, in order to overcome these inherent difficulties in separation and recycling of DECs from solutions, heterogenizing DECs on solid support materials has been receiving increased attention. Recently, a synthetic strategy has been used that involves the immobilization of Gn-PAMAM dendrimer-based DECs containing Pt nanoparticles (PtNPs) within the pores of mesoporous material, SBA-15 (Witham et al. (2010) Nat. Chem., 2:36-41). The resulting material, labeled as Gn-PAMAM-SBA-15, was shown to combine the advantages of both "homogeneous" and "heterogeneous" catalysts and exhibited the "true" features of heterogeneous catalysts (Iwasawa et al. (2004) J. Am. Chem. Soc., 126: 6554-6555). However, the long cylindrical channel pores of SBA-15 mesoporous silica support in which the DECs are encapsulated still pose some limitations for reactants to reach all the PtNPs (or the DECs). Moreover, the DECs in this case are noncovalently immobilized in the support material; thus, they are more likely to leach out (Andres et al. (2007) New J. Chem., 31:1161-1191). Covalent attachment of dendrimers or dendrons onto the surfaces of the channels of mesoporous silicas were achieved using a different synthetic strategy (Jiang et al. (2006) J. Am. Chem. Soc., 128:716-717; Wang et al. (2005) Chem. Eur. J., 11:4975-4982; Reynhardt et al. (2005) Adv. Funct. Mater., 15:1641-1646; Reynhardt et al. (2004) Chem. Mater., 16:4095-4102). In these cases, the dendrimers were synthesized in situ within amine-functionalized SBA-15 by multistep procedures involving the Michael-type addition reaction between the amino groups of the material and methyl acrylate, followed by amidation of the resulting ester groups with ethylenediamine. Furthermore, the covalently supported dendrimers were used to synthesize PdNPs in situ for catalysis (Jiang et al. (2006) J. Am. Chem. Soc., 128:716-717). However, this material also has the DENs within the "small" cylindrical channel pores of SBA-15, possibly limiting the reactants access to all of the DENs. Covalent attachment of dendrimers on a more accessible outer surface of relatively polydisperse and small size (average size ~40 nm) amorphous silica nanoparticles was demonstrated (Hagiwara et al. (2010) Synlett., 1990-1996). The resulting supported PAMAMs were used to anchor a metal complex (palladium(II) acetate), and ionic liquids noncovalently for the Suzuki-Miyaura reaction. There have been other examples on silica-supported dendrimers containing metal complexes for heterogeneous catalysis of various reactions (Reynhardt et al. (2004) Chem. Mater., 16:4095-4102; Bourque et al. (1999) J. Am. Chem. Soc., 121:3035-3038; Bourque et al. (2000) J. Am. Chem. Soc., 122:956-957; Alper et al. (2000) Can. J. Chem., 78:920-920; Chanthateyanonth et al. (2003) J. Mol. Catal. A: Chem., 201:23-31; Chanthateyanonth et al. (2004) Adv. Synth. Catal., 346:1375-1384; Reynhardt et al. (2003) J. Org. Chem., 68:8353-8360; Andres et al. (2007) New J. Chem., 31:1161-1191).

Other notable examples on supported DECs include metal oxides such as silica, alumina, and titania used either to support or to encapsulate DENs (Lang et al. (2003) J. Am. Chem. Soc., 125:14832-14836; Hoover et al. (2006) J. Phys. Chem. B, 110:8606-8612; Auten et al. (2008) Appl. Catal. B: Environ., 81:225-235; Scott et al. (2004) Chem. Mater., 16:5682-5688). The dendrimer shells were then removed by high-temperature treatment during catalyst activation, leaving metal oxide-supported MNPs or catalysts. In a related but slightly different approach, the sol-gel process was used to encapsulate DENs within silica shell using silicic acid (Knecht et al. (2004) Chem. Mater., 16:4890-4895). This resulted in ~80 nm polydisperse silica nanoparticles containing several randomly distributed DENs composed of PAMAM-entrapped Au nanoparticles or quantum dots within the silica nanoparticles. Many of the DENs in the resulting materials appeared to be visibly buried within a thick layer of silica as seen from their reported transmission electron microscopy (TEM) images. The accessibility of the DENs in these materials to external probe molecules or reactants for catalysis is not clear.

Herein, the synthesis and highly efficient recyclable catalytic properties of novel $SiO_2$@Pd-PAMAM core-shell microspheres consisting of etched silica microsphere cores and highly accessible DEN shells are reported. The efficient catalytic activities of the $SiO_2$@Pd-PAMAM core-shell microspheres are confirmed by their ability to catalyze the hydrogenation of various olefins, alkynes, keto, and nitro groups, yielding ~100% conversion with high turnover numbers (TONs) under 10 bar $H_2$ pressure, at room temperature and in reaction times ranging from 10 minutes to 3 hours. Furthermore, the microspheres are shown to be recyclable catalysts in up to five cycles with barely losing their catalytic activities. The $SiO_2$@Pd-PAMAM core-shell microspheres' high catalytic activity is possibly the result of the accessibility of the DECs or PdNPs on the outer surface in the core-shell nanostructure as well as the stability of the PdNPs. The stability and ease of recyclability of the $SiO_2$@Pd-PAMAM core-shell microspheres as catalysts are most likely due to the attachment of the DECs on relatively bigger etched $SiO_2$ microspheres via covalent bonds.

In accordance with the instant invention, silica-dendrimer core shell microspheres are provided. The microspheres comprise an etched silica core covalently attached (optionally via a linker) to at least one dendrimer. Dendrimers include without limitation poly(amido amine) (PAMAM) dendrimers and polypropyleneimine (PPI) dendrimers. In a particular embodiment, the dendrimers are $NH_2$-terminated, OH-terminated, or carboxylate-terminated. In a particular embodiment, the dendrimers have generations ranging from about G3 to about G6. The microspheres may comprise dendrimers of different generations.

The microspheres may further comprise at least one catalyst, particularly wherein the dendrimer encompasses the catalyst. In a particular embodiment, the catalyst is a metal catalyst (e.g., a nanoparticle of a metal catalyst). Metal catalysts include, without limitation: platinum, ruthenium, iron, cobalt, gold, chromium, molybdenum, tungsten, manganese, technetium, rhenium, osmium, rhodium, iridium, nickel, palladium, copper, silver, zinc, tin, aluminum, and combinations (e.g., bimetallic and trimetallic combinations) of these in form of alloys or core-shell structures. In a particular embodiment, the catalyst is palladium nanoparticles.

The instant invention also encompasses methods of synthesizing the silica-dendrimer core shell microspheres. In a particular embodiment, the method comprises a) etching silica microspheres and b) covalently attaching at least one dendrimer to the etched silica microsphere, thereby creating silica-dendrimer core shell microsphere. In a particular embodiment, the method further comprises entrapping a catalyst (e.g., palladium) in the dendrimer, particularly after the dendrimer has been covalently attached to the silica microsphere.

Methods of etching the silica core are known in the art. For example, U.S. Patent Application Publication No. 2010/0093013 provides examples of etching silica with KOH or KCN. In a particular embodiment of the instant invention, the silica is etched with NaOH or KOH.

The dendrimers may be covalently attached to the silica cores by a linker. In a particular embodiment, the etched silica cores are functionalized to assist in the covalent attachment of the dendrimers to the silica core. For example, the etched silica core may be functionalized with a vinyl group, e.g., by grafting vinyltriethoxysilane onto the silica microsphere. The vinylsilica microspheres may then be epoxidated into epoxy-silica microspheres, e.g., through the reaction of m-chloroperoxybenzoic acid with the vinylsilica. The epoxysilica microspheres may then be reacted with at least one dendrimer to generate the silica-dendrimer core shell microsphere. One or more catalysts may then be added (e.g., entrapped) by the dendrimers of the silica-dendrimer core shell microspheres.

The silica-dendrimer core shell microspheres comprising at least one catalyst may be used in any appropriate chemical reaction. For example, the catalyst containing silica-dendrimer core shell microspheres may be used in a hydrogenation reaction or Heck coupling reaction. In a particular embodiment, Pd containing silica-dendrimer core shell microspheres selectively catalyze the reaction of vinyl or nitro groups over arene groups.

II. Core-Shell-Shell Nanospheres

A synthetic method to a highly efficient heterogeneous nanocatalyst, comprising of silica nanosphere ($SiO_2$) decorated with palladium nanoparticles (Pd-NP) that are further encapsulated within a nanoporous silica shell (Porous-$SiO_2$), is reported herein. Briefly, monodisperse, 5 nm and 20 nm Pd nanoparticles are synthesized and anchored onto silica nanospheres of ~250 nm in diameter. These core-shell nanospheres are then coated with a secondary silica shell by the sol-gel process. This is followed by controlled etching of the outer silica shell to yield nanoporous silica shell around the Pd-NP. The thickness of the nanoporous silica shell and its pore structures are controlled by changing the synthetic conditions. The resulting nanoporous silica shell is proved to permit reactants to reach the Pd-NP while at the same time protecting them from aggregation. These new nanomaterials, dubbed $SiO_2$/Pd Nanoparticles/Nanoporous $SiO_2$ (or $SiO_2$/Pd-NP/Porous-$SiO_2$) core-shell-shell nanospheres behave as heterogeneous nanocatalyst exhibiting high catalytic activity and turn-over-numbers (TONs) in hydrogenation reaction of various substrates at room temperature and 20 bar hydrogen pressure. The core-shell-shell nanospheres are proven to be versatile catalysts as they are also able to catalyze C—C coupling reactions effectively. Moreover, these heterogeneous nanocatalysts are stable showing negligible Pd leaching and aggregation, and can be recycled multiple times without loss of catalytic activity.

Palladium-based heterogeneous catalysts have long received great attention owing to their ability to catalyze a variety of useful chemical reactions as well as their advantage of easy recovery and regeneration (Park et al. (2008) Small 4:1694; Ko et al. (2006) Angew. Chem. Int. Ed., 45:7564; Jiang et al. (2006) J. Am. Chem. Soc., 128:716; Yoon et al. (2005) J. Am. Chem. Soc., 127:17174; Narayanan et al. (2005) J. Catal., 234:348; Wu et al. (2009) Green Chem., 11:798). Because of their high surface areas and greater stability, nanostructured materials have recently attracted a great deal of interest for supporting active catalytic sites including metallic nanoparticles such as Pd nanoparticles (Pd-NP) for the preparation of efficient heterogeneous catalysts (Lee et al. (2008) Adv. Mater., 20:1523; Arnal et al. (2006) Angew. Chem. Int. Ed., 118:8404; Ikeda et al. (2006) Angew. Chem. Int. Ed., 45:7063; Scott et al. (2005) J. Am. Chem. Soc., 127:1380; Song et al. (2006) J. Am. Chem. Soc., 128:3027). Pd-NP have now become among the most interesting catalysts because of their size and shape-dependent as well as efficient catalytic activities in a number of reactions (Narayanan et al. (2003) J. Am. Chem. Soc., 125:8340). The most efficient catalytic activity for Pd-NP, and also other metallic nanomaterials, could be ideally attained if the nanomaterials' surface reactive sites were "naked". However, without surface capping agents and stabilizers, the surface atoms of metallic nanoparticles with their typically high surface energy become susceptible to aggregation into bulk material. Consequently, many metal nanoparticles cannot attain their maximum possible catalytic activity and selectivity either because of the presence of their surface passivating ligands or because of their aggregation without them (Budroni et al. (2006) Angew. Chem. Int. Ed., 118:3406; Comotti et al. (2004) Angew. Chem. Int. Ed., 116:5936; Narayanan et al. (2004) J. Am. Chem. Soc., 126:7194). In particular, Pd-NP catalysts are known to aggregate easily into bulk Pd precipitate without strong capping agents around them (Diallo et al. (2007) Angew. Chem. Int. Ed., 46:8644; Thathagar et al. (2006) Angew. Chem. Int. Ed., 45:2886; Mazumder et al.

(2009) J. Am. Chem. Soc., 131:4588; Xu et al. (2008) J. Phys. Chem. C, 112:13419; Hong et al. (2007) Chem. Mater., 19:961). Therefore, the development of highly efficient, stable Pd-based heterogeneous catalysts containing "naked nanoparticles" or nanoparticles with loosely bound surface ligands still remains challenging.

To prepare heterogeneous catalysts with metallic nanoparticles including Pd-NP or to prevent nanoparticles from coalescence, various types of inorganic shells such as silica, carbon and metal oxides around the nanoparticles can be used (Ikeda et al. (2006) Angew. Chem. Int. Ed., 45:7063; Ge et al. (2008) Angew. Chem. Int. Ed., 47:8924; Joo et al. (2009) Nat. Mater., 8:126; Shokouhimehr et al. (2007) Angew. Chem. Int. Ed., 46:7039; Kim et al. (2003) Chem. Commun., 790; Yin et al. (2004) Science 304:711; Yu et al. (2008) J. Phys. Chem. C, 112:2244). Such metal/inorganic type core-shell nanostructures are often generated by using two sequential synthetic steps; i.e. the preparation of metal nanoparticles followed by the deposition of the inorganic material around them using appropriate synthetic methods (Liz-Marzan et al. (1996) Langmuir, 12:4329; Nooney et al. (2002) Adv. Mater., 14:529). For instance, the synthesis of metal-silica core-shell nanospheres with a single metal nanoparticle core that is coated isotropically by a dense silica shell via the well-known Stober method has been reported (Stober et al. (1968) J. Colloid Interface Sci., 26:62). Very recently, the synthesis of core-shell nanosphere catalysts consisting of a single Pd nanoparticle core encapsulated within a porous silica shell has also been achieved (Park et al. (2008) Small 4:1694). However, these core-shell nanospheres have polydisperse size distributions and most of them contain only one metal nanoparticle per each core-shell nanospheres (Park et al. (2008) Small 4:1694; Joo et al. (2009) Nat. Mater., 8:126; Stober et al. (1968) J. Colloid Interface Sci., 26:62). In light of the reports that a large number of edge and corner atoms in metal nanocrystals is required to enhance their catalytic performance (Narayanan et al. (2005) J. Phys. Chem. B, 109: 12663; Lim et al. (2007) Angew. Chem. Int. Ed., 46:9279), it was herein conceived that utilizing smaller and shaped nanoparticles in large number per a single core-shell-shell type nanosphere having a nanoporous shell may result in better catalytic performance.

Herein, the successful synthesis of such novel core-shell-shell nanospheres is reported, with each nanosphere containing several octahedral-shaped 5 nm or 20 nm Pd-NP sandwiched between a silica nanosphere core and a nanoporous silica shell (Porous-$SiO_2$). The resulting materials are labeled as $SiO_2$/Pd-NP/Porous-$SiO_2$ core-shell-shell nanospheres. By using these $SiO_2$/Pd-NP/Porous-$SiO_2$ core-shell-shell nanospheres as heterogeneous catalyst, highly efficient and recyclable catalytic hydrogenation and C—C coupling reactions at room temperature have been demonstrated (Mahesh et al. (2005) J. Org. Chem., 70:4118). Furthermore, the Pd-NP sandwiched between the silica core and the nanoporous silica shell showed good stability and no leaching and aggregation. These novel Pd-based heterogeneous nanocatalysts have applications in many other Pd-catalyzed reactions.

In accordance with the instant invention, core-shell-shell nanospheres are provided. The core-shell-shell nanospheres comprise a silica core (optionally etched) attached (optionally via a linker) to at least one catalyst and an etched silica outer layer which encompasses the catalyst. In a particular embodiment, the catalyst is a metal catalyst (e.g., a nanoparticle of the metal catalyst). Metal catalysts include, without limitation: platinum, ruthenium, iron, cobalt, gold, chromium, molybdenum, tungsten, manganese, technetium, rhenium, osmium, rhodium, iridium, nickel, palladium, copper, silver, zinc, tin, aluminum, and combinations (e.g., bimetallic and trimetallic combinations) of these in form of alloys or core-shell structures. In a particular embodiment, the catalyst is palladium nanoparticles.

The instant invention also encompasses methods of synthesizing the core-shell-shell nanospheres. In a particular embodiment, the method comprises attaching (e.g., covalently attaching) and/or coating at least one catalyst to the silica nanosphere core, adding a silica shell (or other metal or metal oxide as described hereinabove), and etching the silica shell (e.g., such that it is nanoporous). "Nanoporous" refers to a material having an average pore diameter in the nanometer range, particularly in the range of about 0.1 to about 100 nm, particularly about 1 to about 50 nm, more particularly about 1 to about 20 nm.

The catalyst (e.g., Pd nanoparticle) may be attached to the silica cores (e.g., about 50 nm to about 500 nm, particularly about 250 nm) directly or by a linker. In a particular embodiment, the silica cores (optionally etched) are functionalized to assist in the attachment of the catalysts to the silica core. For example, the silica core may be functionalized with $NH_2$ groups, e.g., by reacting silica nanospheres with 3-aminopropyltriethoxysilane. The —$NH_2$ functionalized silica nanospheres may then be reacted with at least one catalyst (e.g., Pd nanoparticle (e.g., about 1 to about 30 nm, particularly about 5 to about 20 nm)) to generate a catalyst coated silica nanosphere.

The outer silica shell may then be added to the catalyst coated silica nanosphere and then the outer shell may be etched. In a particular embodiment, the outer shell is added by the sol-gel process using tetraethyl orthosilicate. In certain embodiments, the outer shell may be about 10 nm to about 200 nm in thickness, more particularly about 20 nm to about 100 nm in thickness, more particularly about 50 nm in thickness. Methods of etching the silica core are known in the art. For example, U.S. Patent Application Publication No. 2010/0093013 provides examples of etching silica with KOH or KCN. In a particular embodiment of the instant invention, the silica is etched with a base such as NaOH or KOH. The amount of etching (e.g., amount of etching time) will define the pore sizes of the outer shell. In a particular embodiment, the outer shell is etched in the absence or presence of polyvinylpyrrolidone (PVP) or other agent that enables in depth and uniform etching of the outer shell, such as polyacrylic acid and polyethyleneimine. In a particular embodiment, the outer shells are etched for less than 150 minutes, particularly about 80 to about 100 minutes.

The core-shell-shell nanospheres comprising at least one catalyst may be used in any appropriate chemical reaction. For example, the catalyst containing core-shell-shell nanospheres may be used in a hydrogenation reaction or Heck coupling reaction. In a particular embodiment, Pd nanoparticle containing core-shell-shell nanospheres are used.

III. Core-Shell-Hollow Shell Nanostructures

The synthesis and catalytic activities of highly stable hollow nanoreactors, dubbed $SiO_2$/Pd/h-$ZrO_2$, which consist of silica microsphere ($SiO_2$)-supported Pd nanoparticle multicores (Pd) that are encapsulated with a hollow and nanoporous $ZrO_2$ shell (h-$ZrO_2$) is provided herein. The $SiO_2$/Pd/h-$ZrO_2$ nanoreactors are fabricated by first synthesizing $SiO_2$/Pd/$SiO_2$/$ZrO_2$ microspheres, and then etching the inner $SiO_2$ shell of the $SiO_2$/Pd/$SiO_2$/$ZrO_2$ microspheres with dilute NaOH solution. The hollow and nanoporous $ZrO_2$ shell of the nanoreactors serves two important functions: 1) it provides reactants a direct access to the Pd nanoparticle multicores inside the $SiO_2$/Pd/h-$ZrO_2$ nanoreactors during catalysis, and 2) it stabilizes the Pd nanoparticles or protects them from aggregation/sintering. Fabricating such structures capable of protecting the Pd nanoparticles from aggregation/sintering is particularly interesting considering the fact that the Pd nanoparticles, which have high tendency to aggregate due to their high surface energies, have 'naked' surfaces or no organic surface passivating ligands that are often necessary to stabilize metallic nanoparticles. The $SiO_2/Pd/h-ZrO_2$ nanoreactors show excellent catalytic activity, as shown in hydrogenation of olefins and nitro group, even at room temperature and under moderate hydrogen pressure. This is resulted from the $SiO_2/Pd/h-ZrO_2$ microspheres' high surface area and their small, stable and naked Pd nanoparticles. Furthermore, the $SiO_2/Pd/h-ZrO_2$ nanoreactor catalysts remain stable after reactions and are recyclable multiple times without losing their high catalytic activities.

Heterogeneous catalysts have been receiving great attention because of their abilities to catalyze a variety of useful chemical reactions and their advantageous properties of being easily recoverable and reusable after catalytic reactions (Park et al. (2008) Small 4:1694-1697; Ko et al. (2006) Angew. Chem. Int. Ed., 45:7564-7567; Jiang et al. (2006) J. Am. Chem. Soc., 128:716-717; Yoon et al. (2005) J. Am. Chem. Soc., 127:17174-17175; Narayanan et al. (2005) J. Catal., 234:348-355; Wu et al. (2009) Green Chem., 11:798-803). Owing to their high surface areas, and in many cases, inherent nanosize-dependent electronic properties, nanostructured materials have been increasingly used as support materials to anchor active catalytic sites such as metallic nanoparticles, and to produce heterogeneous catalysts (Lim et al. (2007) Angew. Chem. Int. Ed., 46:9279-9282; Arnal et al. (2006) Angew. Chem. Int. Ed., 118:8404-8407; Lee et al. (2008) Adv. Mater., 20:1523-1528; Ikeda et al. (2006) Angew. Chem. Int. Ed., 45:7063-7066; Scott et al. (2005) J. Am. Chem. Soc., 127:1380-1381; Song et al. (2006) J. Am. Chem. Soc., 128:3027-3037). Extensive research has also been devoted to developing new and better methods for effectively immobilizing metallic nanoparticle catalysts on high surface area nanostructured and nanoporous support materials (Abu-Reziq et al. (2006) J. Am. Chem. Soc., 128:5279-5282). The immobilization of nanoparticle catalysts on nanostructured support materials can lead to not only new types, and in some cases, efficient heterogeneous catalysts, but also easily recyclable and reusable nanocatalyts. Unfortunately, however, many metallic nanoparticle catalysts, especially those composed of Pd, Au and Pt nanoparticles, are unstable due to their high tendency to aggregate or sinter at elevated reaction temperatures, even after being immobilized on solid support materials. Thus, their catalytic activities often decay rapidly after a single use in catalytic reactions (Albers et al. (2001) J. Mol. Catal. A, 173:275; Narui et al. (1999) Appl. Catal. A, 179:165; Grunwaldt et al. (2007) Chem. Commun., 4635). Hence, there has been a growing interest over the past several years to developing new synthetic strategies to metal nanoparticle-containing heterogeneous nanocatalysts, having not only improved catalytic activities, but also robust structures that result in long term stability and allow easy recovery and reuse.

Supported nanoparticle catalysts are often stabilized by supporting the nanoparticles on, or by encapsulating them within, organic polymers and various types of inorganic materials such as silica, carbon and different metal oxides (Leadbeater et al. (2002) Chem. Rev., 102:3217-3274; McNamara et al. (2002) Chem. Rev., 102:3275-3300; Ge et al. (2008) Angew. Chem. Int. Ed., 47:8924-8928; Joo et al. (2009) Nature Mater., 8:126-131; Shokouhimehr et al. (2007) Angew. Chem. Int. Ed., 46:7039-7043; Kim et al. (2003) Chem. Commun., 790-791; Yin et al. (2004) Science 304: 711-714; Yu et al. (2008) J. Phys. Chem. C, 112:2244-2247). Besides leading to easily recyclable heterogeneous nanocatalysts, the immobilization of nanoparticles on solid support materials often reduces the tendencies of the nanoparticles to coalesce during catalytic reactions, and in some cases it also results in more selective/efficient catalysts. Recently, metal oxide microspheres have emerged as support materials for metallic nanoparticles, producing new classes of stable nanocatalysts. For instance, spherical $SiO_2$ microsphere containing a Pd nanoparticle per microsphere was synthesized, and the resulting nanocomposite material was shown to have high catalytic activity in ethylene hydrogenation and CO oxidation reactions without the Pd nanoparticles undergoing aggregation (Park et al. (2008) Small 4:1694-1697). In another example, a novel synthetic approach to hollow $SiO_2$ microsphere-based nanoreactors, denoted as yolk@shell silica-coated Au nanoparticles, has been reported and the materials' catalytic activities in catalytic reduction of p-nitrophenol was shown (Lee et al. (2008) Chem. Mater., 20:5839-5844). Other metal oxides, coupled with $SiO_2$ microspheres, have also been used to stabilize metallic nanoparticle catalysts. For example, a hollow spherical shaped nanoreactor composed of ~5 nm Au core that is encapsulated within a hollow spherical $ZrO_2$ shell was synthesized and shown to catalyze an oxidation reaction of CO (Huang et al. (2009) Small 5:361-365; Arnal et al. (2006) Angew. Chem. Int. Ed., 45:8224-8227). However, in each of these cases, the $SiO_2$ microsphere-based nanoreactors contain one metal nanoparticle per a microsphere support, making the system 'underutilized'. Furthermore, the metal nanoparticles used in these systems are relatively bigger in sizes—a size that is not the most conducive for many catalytic reactions.

Here, the synthesis of a highly stable and efficient catalytic nanoreactor is reported, which consists of $SiO_2$ microsphere-supported metal nanoparticle multicores that are further coated by a hollow and nanoporous $ZrO_2$ shell. This is demonstrated for Pd nanoparticles—which are known to have high tendency to aggregate or sinter due to their high surface energies—as model systems. However, the work can easily be extended to other metallic nanoparticles. The $SiO_2/Pd/h-ZrO_2$ nanoreactor is fabricated by first synthesizing $SiO_2/Pd/SiO_2/ZrO_2$ nanospheres, and then etching the inner $SiO_2$ shell of the $SiO_2/Pd/SiO_2/ZrO_2$ nanospheres with dilute aqueous base solution. The resulting nanoreactor is labelled as $SiO_2/Pd/h-ZrO_2$ core-shell-shell microsphere, in which $SiO_2$ refers to its $SiO_2$ core, Pd represents its Pd nanoparticle multicores supported onto the $SiO_2$ core, and h-$ZrO_2$ denotes its hollow and nanoporous $ZrO_2$ shell. The hollow and nanoporous $ZrO_2$ shell of the material is shown to serve two important functions: 1) it provides reactants a direct access to the Pd nanoparticle multicores of the $SiO_2/Pd/h-ZrO_2$ nanoreactor during catalysis, and 2) it stabilizes and protects the Pd nanoparticles from aggregation/sintering. The $SiO_2/Pd/h-ZrO_2$ core-shell-shell microspheres show excellent catalytic activities when tested using hydrogenation as a model catalytic reaction. Furthermore, the microspheres are recyclable, at least five times, without losing their catalytic activities.

In accordance with the instant invention, core-shell-hollow shell nanostructures are provided. The core-shell-hollow shell nanostructures comprise a silica core (optionally etched) attached (optionally via a linker) to at least one catalyst and a hollow nanoporous outer sphere which encompasses the catalyst coated core. In a particular embodiment, the catalyst is a metal catalyst (e.g., a nanoparticle of the metal catalyst). Metal catalysts include, without limitation: platinum, ruthenium, iron, cobalt, gold, chromium, molybdenum, tungsten, manganese, technetium, rhenium, osmium, rhodium, iridium, nickel, palladium, copper, silver, zinc, tin, aluminum, and combinations (e.g., bimetallic and trimetallic combinations) of these in form of alloys or core-shell structures. In a particular embodiment, the catalyst is palladium nanoparticles.

In a particular embodiment, hollow nanoporous outer sphere comprises one or more inorganic oxides, particularly metal oxides. Examples of suitable metal oxides for the outer shell include without limitation nickel, cobalt, manganese, titanium, vanadium, zirconium, iron, cerium, zinc, and aluminum oxides. In a particular embodiment, the outer shell comprises $ZrO_2$.

The instant invention also encompasses methods of synthesizing the core-shell-hollow shell nanostructures. In a particular embodiment, the method comprises attaching (e.g., covalently attaching) and/or coating at least one catalyst to the silica nanosphere core, adding a silica shell (or other metal or metal oxide as described hereinabove), adding an outer shell (e.g., of a metal oxide), and etching away the silica shell.

The catalyst (e.g., Pd nanoparticle) may be attached to the silica cores (e.g., about 50 nm to about 500 nm, particularly about 250 nm) directly or by a linker. In a particular embodiment, the silica cores (optionally etched) are functionalized to assist in the attachment of the catalysts to the silica core. For example, the silica core may be functionalized with $NH_2$ groups, e.g., by reacting silica nanospheres with 3-aminopropyltriethoxysilane. The —$NH_2$ functionalized silica nanospheres may then be reacted with at least one catalyst (e.g., Pd nanoparticle (e.g., about 1 to about 30 nm, particularly about 5 to about 20 nm)) to generate a catalyst coated silica nanosphere.

The silica shell may then be added to the catalyst coated silica nanosphere. In a particular embodiment, the outer shell is added by the sol-gel process using tetraethyl orthosilicate. In certain embodiments, the silica shell may be about 10 nm to about 200 nm in thickness, more particularly about 20 nm to about 100 nm in thickness, more particularly about 50 nm in thickness.

The hollow outer shell may then be added to the core-shell-shell nanospheres. In a particular embodiment, the outer shell (e.g., Zr) is added in the presence of a surfactant (e.g., Brij 30) to assist in the formation of a nanoporous outer shell upon removal of the surfactant. Other surfactants include, without limitation, such as Pluronics® (poly(ethylene glycol)-poly (propylene glycol) block copolymers and poly(ethylene glycol)-polypropylene glycol)-poly(ethylene glycol) block copolymer; e.g., Pluronics® 123) and cetyltrimethylammonium bromide, which may produce nanoporous structures with slightly different pore sizes In a particular embodiment, the outer shell is about 1 nm to about 50 nm, particularly about 5 nm to about 35 nm, particularly about 10 nm to about 25 nm, particularly about 18 nm in thickness.

Upon the addition of the outer shell, the silica shell may then be removed (e.g., by etching). Methods of etching the silica core are known in the art. For example, U.S. Patent Application Publication No. 2010/0093013 provides examples of etching silica with KOH or KCN. In a particular embodiment of the instant invention, the silica shell is removed by a base such as NaOH or KOH. In a particular embodiment, the silica shell is removed without substantial removal of the silica core. In a particular embodiment, at least about 75%, particularly at least about 90% of the silica shell is removed.

The core-shell-hollow shell nanostructures comprising at least one catalyst may be used in any appropriate chemical reaction. For example, the catalyst containing core-shell-hollow shell nanostructures may be used in a hydrogenation reaction or a Heck coupling reaction. In a particular embodiment, Pd nanoparticle containing core-shell-hollow shell nanostructures are used.

IV. Definitions

The following definitions are provided to facilitate an understanding of the present invention:

As used herein, the term "catalyst" refers to a substance that increases the rate of a chemical reaction while not being consumed in the reaction.

As used herein, the term "selective" refers to the capability of the catalyst to cause the production of specific products by selectively catalyzing a specific reaction, particularly in a mixture of similarly reactive compounds or from competitive reactions.

As used herein, the term "turnover number" refers to the number of moles of reactant that a mole of catalyst can convert to product before becoming inactivated.

As used herein, the term "etch" refers to a process by which a portion of a layer is reacted away, dissolved or otherwise removed.

As used herein, a "dendrimer" refers to repeatedly branched molecules. Dendrimers are typically characterized by their structure perfection. Dendrimers are macromolecules having a core and at least one shell of branching structures emanating from the core. Dendrimers include one or more shells or "generations" (e.g., G1, G2, G3, etc.).

As used herein, "linker" refers to a chemical moiety comprising a covalent bond or a chain of atoms that covalently attaches at least two compounds, for example, a dendrimer to a silica core. The linker can be linked to any synthetically feasible position of the compounds, but preferably in such a manner as to avoid blocking the compounds desired activity. Linkers are generally known in the art. Exemplary linkers may comprise at least one optionally substituted; saturated or unsaturated; linear, branched or cyclic alkyl or carbonyl group or an optionally substituted aryl group. In a particular embodiment, the linker may contain from 0 (i.e., a bond) to about 500 atoms, about 1 to about 100 atoms, or about 1 to about 50 atoms. The linker may also be a polypeptide (e.g., from about 1 to about 20 amino acids). The linker may be biodegradable under physiological environments or conditions. The linker may be non-degradable and can be a covalent bond or any other chemical structure which cannot be cleaved under physiological environments or conditions.

A "carrier" refers to, for example, a diluent, adjuvant, preservative, anti-oxidant, solubilizer, emulsifier, buffer (e.g., Tris HCl, acetate, phosphate), water, aqueous solution, saline solution, dextrose and glycerol solutions, or vehicle with which a nanoparticle of the present invention can be contained.

The following examples provide illustrative methods of practicing the instant invention, and are not intended to limit the scope of the invention in any way.

EXAMPLE 1

Experimental Section

Chemicals and Reagents

Anhydrous ethanol, aqueous ammonium hydroxide solution (28%), tetraethyl orthosilicate (TEOS, 98%), Pd/C (1%), sodium borohydride ($NaBH_4$), m-chloroperoxybenzoic acid, styrene, phenylacetylene, potassium hydroxide, cyclohexene, n-hexene, acetone, acetyleacetonate, styrene oxide, 4-chloroaniline, trans-stilbene, 4-nitrostyrene, acetonitrile, methanol, and sodium tetrachloropalladate(II) ($Na_2PdCl_4$)

were obtained from Sigma-Aldrich. Palladium(II) acetylacetonate (99%) was purchased from Strem Chemicals, Inc. Methylene chloride and hydrochloric acid were obtained from Fisher Scientific. Poly-(amidoamine) (PAMAM) dendrimers (G4) as 10-25% in methanol was obtained from Dendritech NanoTechnologies, Inc., Midland, Mich.

Synthesis of Silica Microspheres

The synthesis of the spherical silica microspheres was carried out as described (Stober et al. (1968) J. Colloid Interface Sci., 26:62-66; Asefa et al. (2008) J. Mater. Chem., 18:5604-5614). In a 250 mL plastic bottle, aqueous ammonia solution (10 mL), ethanol (100 mL), and distilled water (3.6 mL) were added and stirred vigorously for 2 minutes. Then, TEOS (5.84 g) was added into the solution under moderate stirring to hydrolyze TEOS. After 3 hours of stirring, the solution was centrifuged and the supernatant was decanted carefully. The precipitate was washed three times with 3×40 mL of 1:1 ethanol/water solution by sonication, centrifugation, and decantation. Finally, the precipitate was dispersed by sonication in 40 mL 1:1 ethanol/water solution. This resulted in 450 nm silica microspheres.

Synthesis of Etched Silica Microsphere Cores ($SiO_2$)

The 450 nm silica microspheres synthesized above were etched with 0.01 M aqueous potassium hydroxide (KOH) solution. This is performed to create nanocorrugated surface and increase the microspheres' surface area and consequently help the microspheres anchor the PAMAM dendrimers more effectively. Typically, 250 mg of the silica microspheres was suspended in 0.01M KOH solution (100 mL) and stirred for 2 hours. The resulting etched silica microspheres were centrifuged, and the supernatant was decanted. The particles were washed three times with 3×20 mL Millipore water via sonication, centrifugation, and decantation. They were then dried in a desiccator under vacuum at room temperature (RT). The etched silica microspheres were labeled as $SiO_2$.

Grafting Vinyltriethoxysilane (VTS) on the Silica Microspheres

The etched $SiO_2$ microspheres were dried at 100° C. for 12 hours prior to grafting by vinyltriethoxysilane (VTS). In a 500 mL round-bottom flask, 500 mg of the etched $SiO_2$ microspheres was dispersed in dry toluene (250 mL). VTS (3 mL) was then added into the flask, and the solution was refluxed at 80° C. for 6 hours. The resulting vinyl-functionalized silica microspheres were collected by centrifugation and washed via sonication, centrifugation, and decantation using 3×10 mL of toluene, 3×10 mL of methylene chloride, and finally 3×10 mL of ethanol. The precipitate was then dried at RT to produce the vinylsilica microspheres.

Epoxidation of Vinylsilica Microspheres into Vinyl Oxide (Epoxysilica) Microspheres In a 200 mL round-bottom flask, 500 mg of the above synthesized vinylsilica microspheres was dispersed in acetonitrile (50 mL). After adding excess m-chloroperoxybenzoic acid (500 mg) into the solution, it was stirred at RT for 24 hours. The resulting epoxysilica microspheres were collected by centrifugation. After decanting the supernatant, the precipitate was washed three times with acetonitrile (3×10 mL) and then three times with ethanol (3×10 mL) via sonication, centrifugation, and decantation. The resulting vinyl oxide-functionalized silica microspheres were then dried and labeled as epoxysilica microspheres.

Ring-Opening of Epoxy Groups of Epoxysilica Microspheres by Amine Groups of G4 PAMAM Dendrimer In a 100 mL round-bottom flask 400 mg of above prepared epoxysilica microspheres was mixed with G4 PAMAM dendrimer (0.5 mL) and anhydrous acetonitrile (50 mL), and the solution was stirred for 24 hours at RT. The 0.5 mL of 10-25% stock solution of G-4 PAMAM dendrimer in methanol, which was obtained from Dendritech NanoTechnologies, Inc., was calculated to have 3.5-8.8 μmol of PAMAM. The resulting PAMAM dendrimer-functionalized silica microspheres were collected by centrifugation and washed via sonication, centrifugation, and decantation with anhydrous acetonitrile (50 mL), followed by anhydrous ethanol (50 mL), and let to dry. This produced $SiO_2$@PAMAM dendrimer core-shell microspheres, which were found to have 5.9 μmol PAMAM/g sample by thermogravimetric analysis (TGA).

Entrapping Palladium Nanoparticles within the PAMAM Dendrimers of $SiO_2$@PAMAM Core-Shell Microspheres (Synthesis of $SiO_2$@Pd-PAMAM Core-Shell Microspheres)

$SiO_2$@PAMAM dendrimer core-shell microspheres (250 mg) were dispersed by sonication in distilled water (10 mL). The solution was then treated with 2M HCl (3 mL) for 30 minutes at RT, until its pH became 2.00. This was performed in order to quaternize the remaining terminal primary amine groups in the PAMAM shell of the $SiO_2$@PAMAM microspheres. This will, in turn, help the amine groups on the external surface of the core-shell microspheres not to anchor Pd(II) ions and not to lead to the uncontrolled growth of Pd particles on the outer surface of the core-shell microspheres. After this step, 0.05 M $K_2PdCl_4^-$(aq) solution (250 μL) was slowly added, making the G4 PAMAM dendrimer to palladium(II) ratio 3:5. The solution was stirred at RT for 30 minutes to let Pd(II) ions anchor within the cores of the PAMAM dendrimers. Then, 1 M $NaBH_4$(aq) solution (500 μL) was added. This caused the solution to change its color from yellowish to golden brown, indicating the transformation of Pd(II) to Pd(0) (or Pd nanoparticles). The solid material was separated by centrifugation; washed twice with 2×20 mL distilled water via sonication, centrifugation, and decantation; and then dried at room temperature in a desiccator. The resulted material was labeled as $SiO_2$@Pd-PAMAM core-shell microspheres. The sample was kept in a desiccator until its use in catalytic reactions.

Synthesis of $SiO_2$@Pd Microspheres

A reference core-shell microsphere, labeled as $SiO_2$/Pd, containing no PAMAM shell was also synthesized as described (Li et al. (2011) ChemCatChem, 3:1277-1280). In a typical synthesis, etched silica microspheres ($SiO_2$) (100 mg) were dispersed in distilled water (10 mL) by sonication for 1 minute and then treated with 20 wt % aqueous $HNO_3$ for 24 hours. After filtration, the particles were washed with distilled water. After drying overnight at 110° C., the resulting $SiO_2$ microspheres (100 mg) were stirred with Pd(II) acetylacetonate/acetylacetone solution (2 mL) at room temperature for 24 hours. The concentration of Pd(II) ions with respect to $SiO_2$ microspheres was set to 0.05 wt % Pd in order to produce small size Pd(0) nanoparticles, as reported (Li et al. (2011) ChemCatChem, 3:1277-1280). The solvent was then slowly evaporated at 110° C. under stirring. The obtained solid was dried overnight at 110° C. and then calcined in air at 800° C. for 4 hours. Before the sample was used in catalysis, it was treated with $NaBH_4$ in order to reduce any PdO, possibly formed on the sample's surface during and after synthesis, into Pd(0). The solid sample was then let to dry at RT resulting in $SiO_2$@Pd microspheres, which were kept in a desiccator until use in catalytic reactions.

Catalytic Hydrogenation Reaction

The hydrogenation reactions were carried out in a 50 mL high-pressure reactor (Parr Instrument Co.). The reactor was equipped with a heating arrangement, overhead stirrer, thermowell, and pressure gauge as well as a transducer, a gas inlet, a gas outlet, and a sampling valve. The reactor has controllers to set temperatures, pressure and agitation speeds to maximum values of 350° C., 4000 psig pressure and 1500 rpm, respectively. The reactor was charged with reactant (0.01 mol), methanol (20 mL), and $SiO_2$@Pd-PAMAM core-shell microsphere catalyst (or control sample) (5 mg) and tightly closed, leak-proof. The reactants included styrene, phenylacetylene, cyclohexene, n-hexene, acetone, acetylacetonate, styrene oxide, 4-chloroaniline, trans-stilbene, and 4-nitrostyrene. The reactor was flushed three times with nitrogen and then three times more with hydrogen before each reaction. Then hydrogen gas was introduced into the reactor to the desired pressure, and the heater was turned on to achieve the desire reaction temperature under a slow stirring rate at ~100 rpm for uniform heat distribution. After attaining the desired temperature, the reaction was initiated by increasing the agitation speed to 500 rpm. The absorption of hydrogen gas due to reaction was monitored from the pressure drop in the reactor. The reaction was stopped when the gas absorption ceased. The reactor was cooled, and the reaction mixture was analyzed by gas chromatography (GC) and gas chromatography-mass spectrometry (GC-MS).

Instrumentation

FTIR spectra were obtained from samples loaded onto a KBr disk (25×4 mm) using a Thermo-Nicolet IR200 spectrometer. Thermogravimetric analysis (TGA) was performed using a TA Q50 thermogravimetric analyzer with a temperature ramp of 10° C./minute from room temperature to 780° C. under nitrogen gas flow. The UV-vis diffuse reflectance spectra of the samples were obtained with a Lambda 850 spectrophotometer (PerkinElmer) by sandwiching the powder samples between two 3×3 cm quartz slides. Powder X-ray diffraction (XRD) patterns were recorded on a Siemens, Daco-Mp instrument having Cu Kα radiation with wavelength of 1.54 Å. The diffractometer was set to 40 kV accelerating voltage and 30 mA, and the data were obtained by setting a wide scan range of 2θ from 20° to 80° with step size of 0.015° and dwell time of 5 seconds. Transmission electron microscope (TEM) images were obtained with a TOPCON microscope operating at 200 kV on samples prepared on carbon/Formvar-coated Cu grids. The catalytic reactions were analyzed by using an Agilent 6850 GC instrument equipped with an HP-1 column (1% dimethylpolysiloxane, 30 m length, 0.25 mm i.d., and 0.25 μm film thickness) and a flame ionization detector. The products were further confirmed by a HP 5890 (MSD-5972) GC-MS instrument containing a HP-5 MS 50 m×0.200 mm×0.33 μm capillary column. Elemental analyses of the materials were carried out by Robertson Microlit Laboratories (Ledgewood, N.J.).

Results

Synthesis and Structural Analysis

For the synthesis of $SiO_2$@Pd-PAMAM and $SiO_2$@Pd core-shell microspheres, first 450 nm silica microspheres, which were synthesized by the Stober method (Stober et al. (1968) J. Colloid Interface Sci., 26:62-66), were etched with KOH (FIG. 1). This produced ~305 nm size nanocurrugated/nanoporous silica microspheres, labeled here as $SiO_2$. The etched silica microspheres were chosen here as support materials for dendrimers or dendrimer-encapsulated catalysts (DECs) because it has been found that such etched silica microspheres were more conducive to support metallic nanoparticles as well as biomolecules by the virtue of their nanocurrugated surface, nanoporous structure, high surface area, and relatively larger density of surface silanol groups (Asefa et al. (2008) J. Mater. Chem., 18:5604-5614; Biradar et al. (2010) ChemCatChem, 8:1004-1010).

To attach G4 PAMAM dendrimers or the DECs onto $SiO_2$, first, vinyltriethoxysilane (VTS) was grafted on the surface of the etched silica microspheres. This produced vinyl-functionalized silica (vinylsilica) microspheres. The surface vinyl groups were then converted to epoxides using m-chloroperoxybenzoic acid at room temperature. After centrifugation and washing with anhydrous acetonitrile, epoxysilica microspheres were obtained. On these epoxysilica microspheres, amine-terminated G4 PAMAM dendrimers were covalently anchored through nucleophilic ring opening of the epoxides by the primary amine groups of the G4 PAMAM dendrimers, resulting in $SiO_2$@PAMAM core-shell microspheres. The reaction does not need any catalyst as the silica surface itself or its residual silanol groups served as a mild catalyst for the epoxide ring-opening reaction (Sreedhar et al. (2007) J. Mol. Catal. A: Chem., 272:159-163; Chakraborti et al. (2004) Org. Biomol. Chem., 2:1277-1280). Furthermore, since the terminal primary amine groups of the PAMAM dendrimers are more accessible, they are capable of opening up the epoxides under the reaction conditions used (Sreedhar et al. (2007) J. Mol. Catal. A: Chem., 272:159-163; Bonollo et al. (2007) Synlett, 2683-2686). Once one of the few primary amine groups of PAMAM dendrimers anchor onto the epoxysilica microspheres, the other primary amine groups that are not close enough to the epoxy groups remain as they are on the $SiO_2$@PAMAM core-shell microspheres. These residual primary amine groups were converted to quaternary ammonium ions by stirring the microspheres in dilute HCl solution in order to prevent the amine groups from anchoring Pd(II) ions. This, in turn, prevented the uncontrolled growth of bigger Pd particles on the external surface of PAMAM shell. After this step, Pd(II) ions were anchored by using the residual amido groups within the dendrimer cores. The Pd(II) ions were then reduced into Pd(0) by following Crooks' method (Niu et al. (2001) J. Am. Chem. Soc., 123:6840-6846). This generated Pd nanoparticles (PdNPs) within the cores of the PAMAM shells, resulting in the $SiO_2$@Pd-PAMAM core-shell microspheres (or $SiO_2$ supported DEC nanocatalysts).

The materials after each step of syntheses were characterized by FTIR spectroscopy (FIG. 2A-2E). The FTIR spectrum of $SiO_2$ microspheres showed a broad O—H stretching peak between 2500 and 3500 $cm^{-1}$ and a strong Si—O—Si stretching band centered at ~980 $cm^{-1}$. The spectrum for vinylsilica microspheres showed C—H stretching and vibrational modes corresponding to the vinyl groups at ~3065 and ~1410 $cm^{-1}$, respectively, and an additional C=C stretching band as a shoulder at ~1610 $cm^{-1}$ (Grieken et al. (2010) Microporous Mesoporous Mater., 131:321-330). Upon epoxidation, the stretching peak corresponding to C—H of C(O)—C—H remained at ~3065 $cm^{-1}$, and a peak corresponding to epoxide appeared at ~909 $cm^{-1}$ (Macan et al. (2004) J. Thermochim. Acta, 414:219-225; Jiang et al. (2005) J. Photochem. Photobiol. A: Chem., 174:165-170). After the epoxysilica microspheres were reacted with G4 PAMAM dendrimers, a new N—H deformation peak corresponding to amide groups at ~1555 $cm^{-1}$ appeared.

The $N_2$ gas adsorption/desorption isotherms for the all the samples are shown in FIG. 2F. The Brunauer-Emmett-Teller (BET) surface areas of unetched $SiO_2$, etched $SiO_2$, vinylsilica and epoxysilica microspheres, and $SiO_2$@PAMAM and SiO2@Pd-PAMAM core-shell microspheres were 20, 29, 25, 17, 15, and 13 $m^2 g^{-1}$, respectively (Table 1). Their TGA results (FIG. 3 and Table 2) showed a slight weight loss below ~120° C. in all the cases, which was attributed to the loss of physisorbed water from the samples. The weight loss from the samples in the range 150-780° C. on the thermogravimetric traces was attributed mainly to the loss of organic groups. In this temperature range, the weight losses from vinylsilica and epoxysilica microspheres and $SiO_2$@PAMAM core-shell microspheres were 5.9, 9.5, and 17.9%, respectively. These weight losses correspond to the loss of vinyl, epoxy, and PAMAM-epoxy species, respectively. The trend in increase in wt % loss from vinylsilica to epoxysilica microspheres and then to $SiO_2@$-PAMAM clearly confirmed the successful anchoring of more organic groups, including the dendrimers, on the $SiO_2$ microspheres in subsequent steps of the syntheses. The wt % epoxy and PAMAM groups on the samples were calculated from the difference in the values of these weight losses as shown in Table 2. Further careful analysis of the TGA results indicated that there were ~2.25 mmol of epoxides per gram of epoxysilica microspheres. Similar calculation gave ~5.90 µmol of PAMAM per gram of $SiO_2@$PAMAM core-shell microspheres. Geometrical calculation along with the density of silica of ~2 g/cm$^3$ (Philipse et al. (1989) J. Colloid Interface Sci., 128:121-136) reveals the existence of ~$3.38 \times 10^{13}$ silica microspheres in a gram of ~305 nm monodisperse $SiO_2$ microspheres. This calculation is reasonable considering the fact that the silica microspheres are monodisperse. When this is combined with the mmol of epoxides and PAMAM per gram of sample, it gives ~$4.01 \times 10^7$ epoxides and ~$1.05 \times 10^5$ PAMAMs per $SiO_2@$PAMAM core-shell microsphere. Geometrical calculation is also used to obtain the theoretical surface area of 9.87 m$^2$ for a gram of ~305 nm smooth spherical microspheres. This area is half as much as the experimental BET surface area of ~20 m$^2$/g, which was obtained by $N_2$ sorption measurement for the etched ~305 nm silica microspheres. The difference between the two surface areas is mainly because the etched microspheres have nanocorrugated and nanoporous surface, while the geometrical calculation is applied to smooth spherical silica microspheres.

TABLE 1

BET surface area results obtained from $N_2$ gas adsorption experiments of the different $SiO_2$-Based microspheres including $SiO_2@$Pd-PAMAM microspheres.

| SAMPLE NAME | BET SURFACE AREA M$^2$/G |
|---|---|
| $SiO_2$ microspheres | 20 |
| etched $SiO_2$ microspheres | 29 |
| vinylsilica microspheres | 25 |
| epoxysilica microspheres | 17 |
| $SiO_2@$PAMAM | 15 |
| $SiO_2@$Pd-PAMAM | 13 |

TABLE 2

Weight losses of organic groups calculated from TGA traces for the different samples.

| Sample | Composition | % Wt Loss in the Range 200-750°C. | % Wt Change Compared to the Proceeding Sample | Moles of Functional Groups |
|---|---|---|---|---|
| $SiO_2$ | $SiO_2$ | 4.7 | | |
| vinyl-silica | $SiO_2$—$(CH=CH_2)_n$ | 5.9 | 1.2 | NA$^a$ |
| epoxy-silica | $SiO_2$—$[CH(O)CH_2]_n$ | 9.5 | 3.6 | 2.3 mmol epoxide/g |
| $SiO_2@$PAMAM | $SiO_2$—$[CH(O)CH_2]_{n-m}$ $(PAMAM)_m$ | 17.9 | 8.4 | 5.9 µmol PAMAM/g |

$^a$The exact amount of functional group in this case (i.e., vinyl groups) is hard to determine as the weight change from $SiO_2$ to vinylsilica is not necessarily only due to the addition of vinyl groups but also due to the loss of some of the Si—OH (silanol) groups during grafting of the vinyltriethoxysilane on them.

Figure 4:
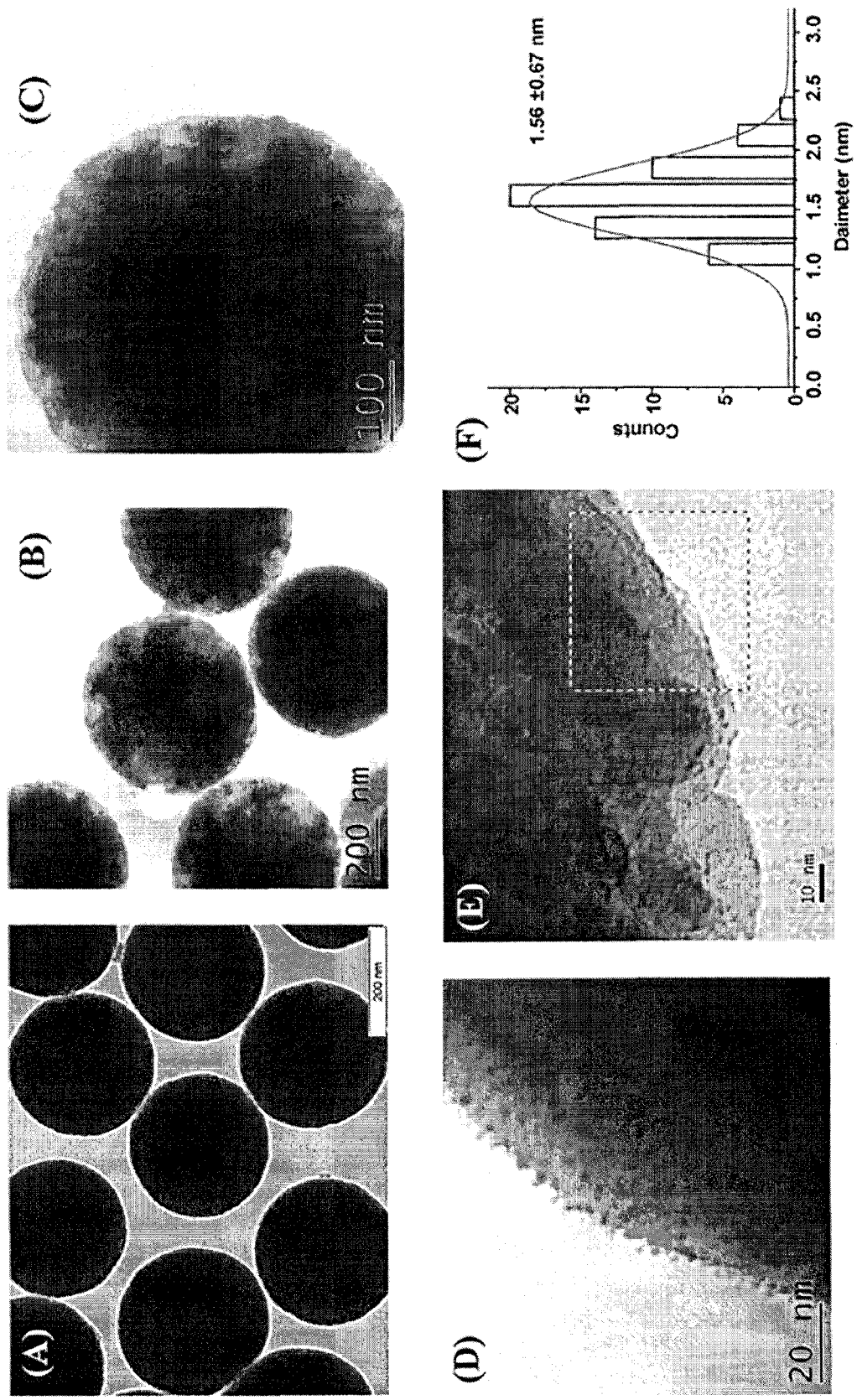
Figure 4G:
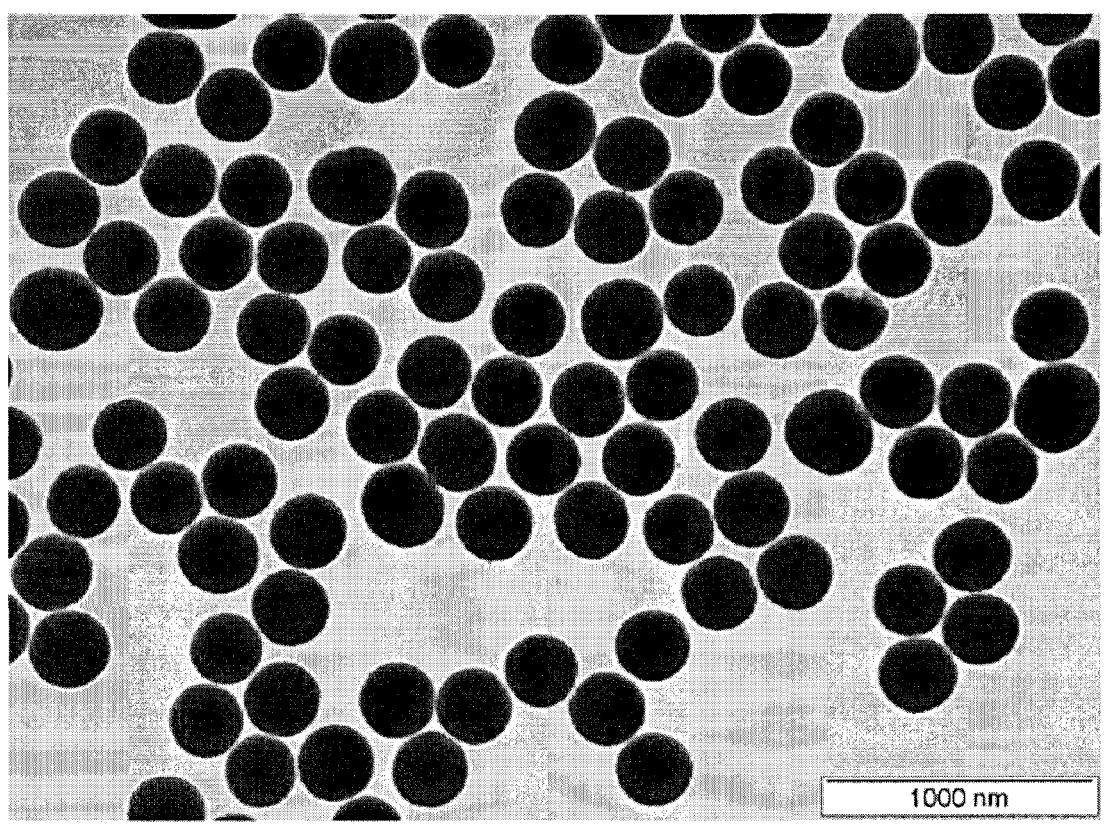
Figure 4G:
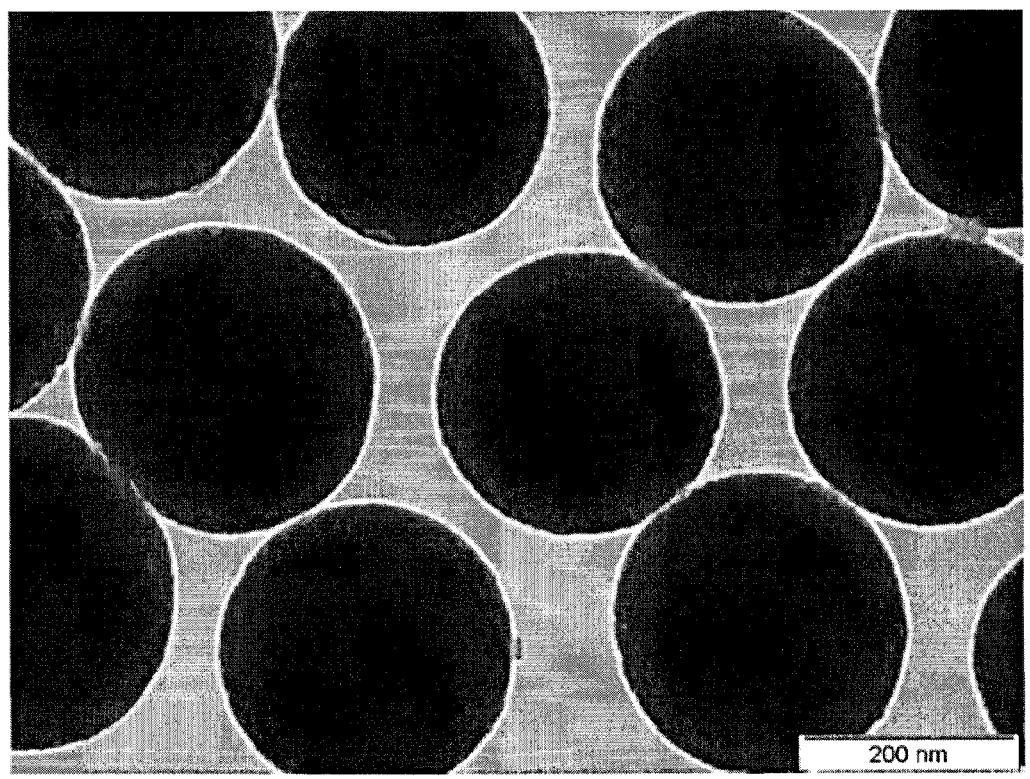
Figure 4H:
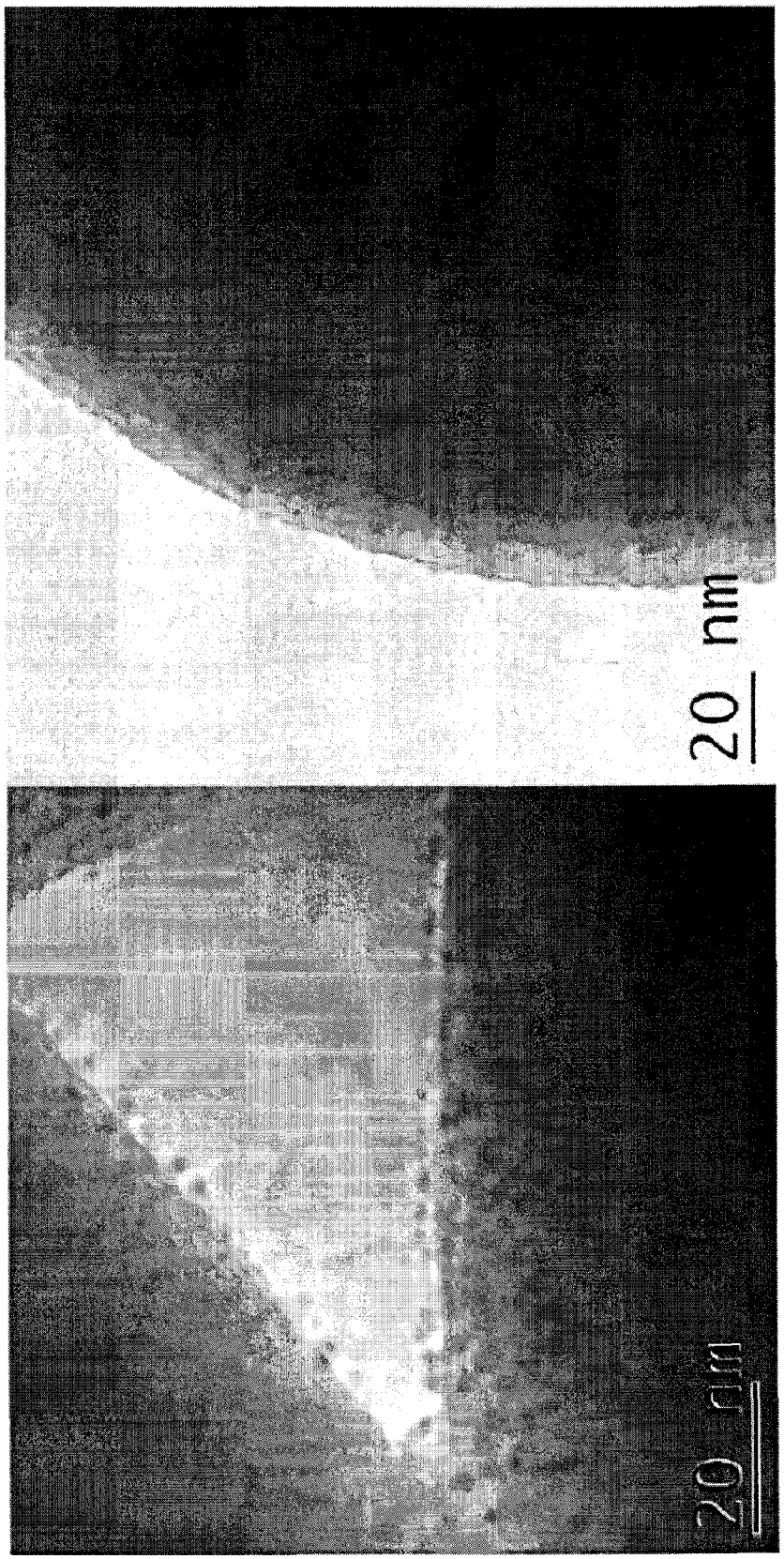
Figure 5:
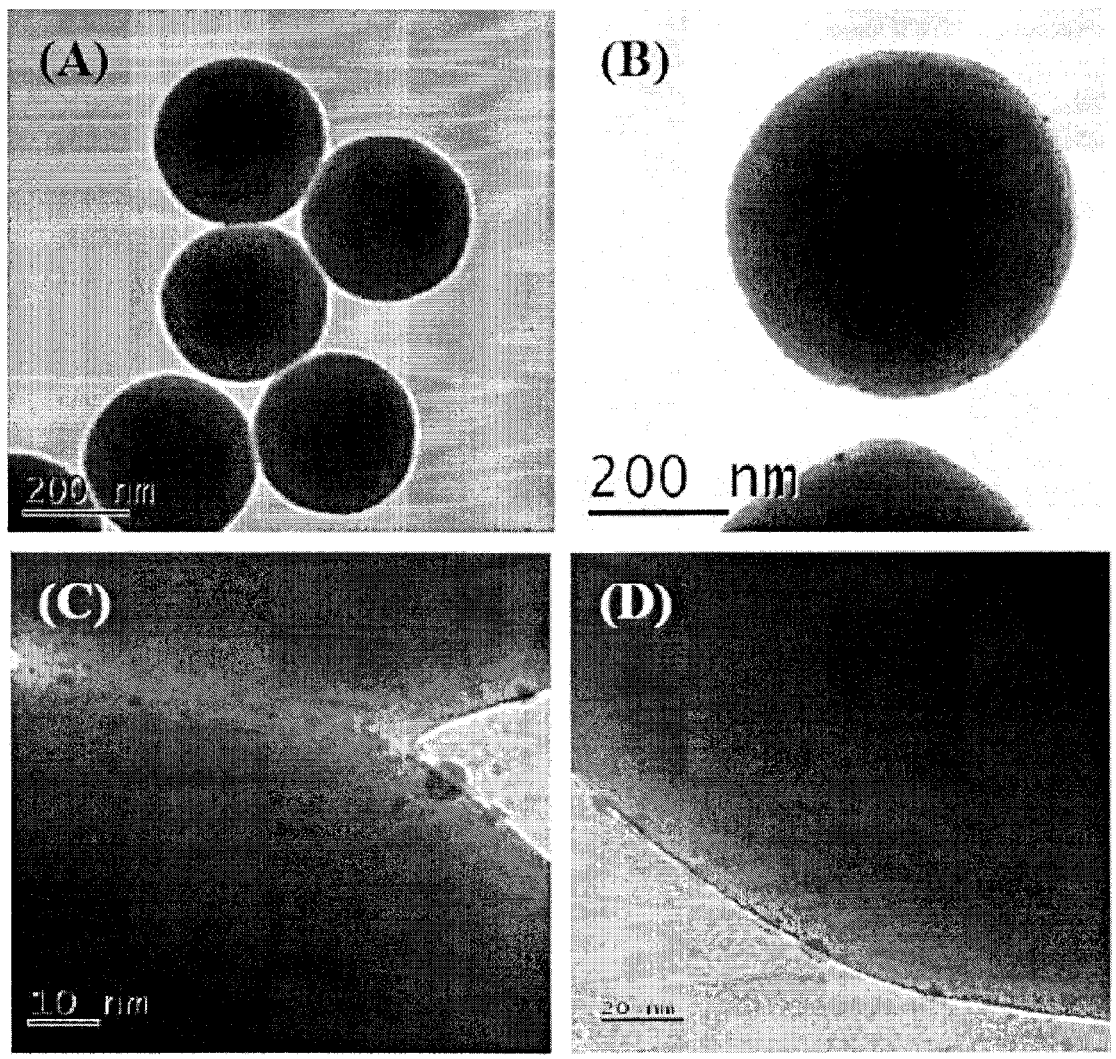
Figure 5E:
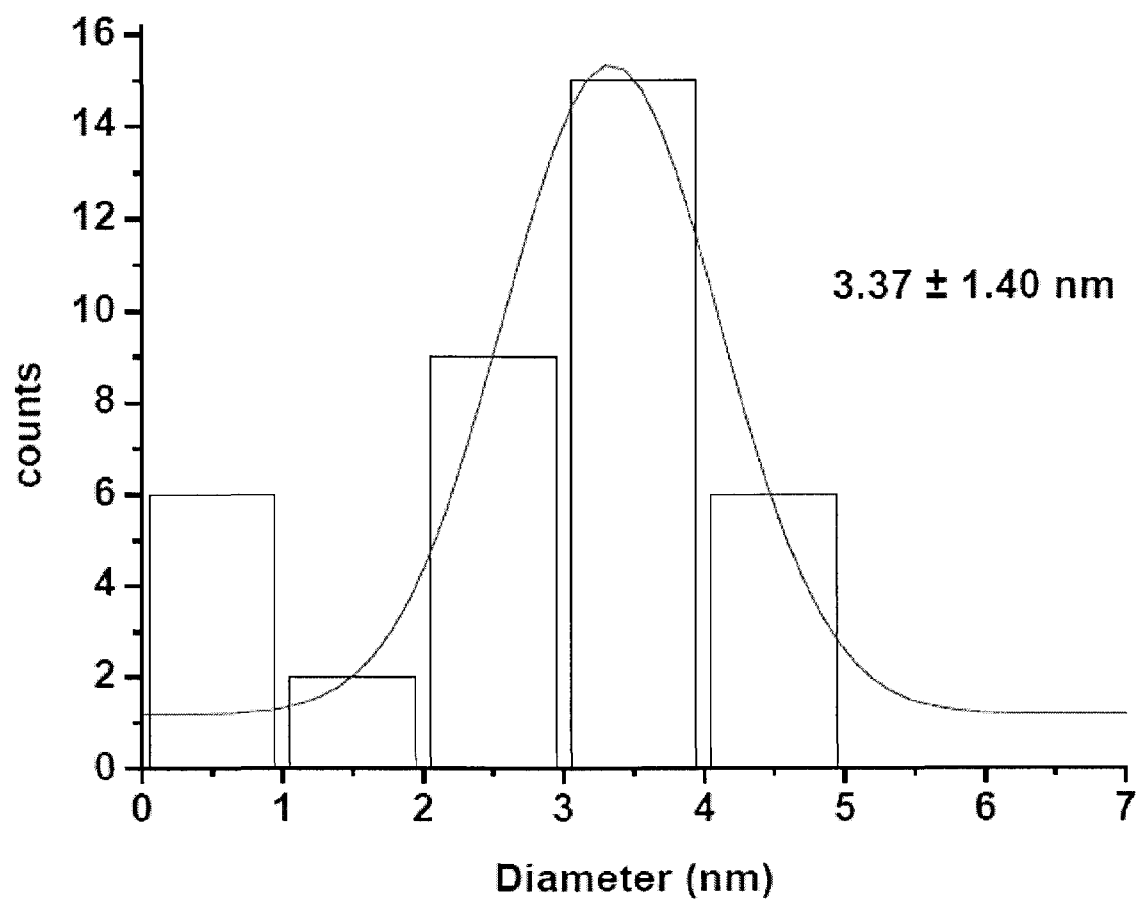

The TEM image of the SiO2@Pd-PAMAM dendrimer core-shell microspheres is shown in FIGS. 4 and 5. The images clearly show that large numbers of PdNPs are supported on the surface of the $SiO_2@$Pd-PAMAM core-shell microspheres. The average size of the PdNPs is 1.56±0.67 nm (FIG. 4F). The control experiment involving simple impregnation of Pd(II) on $SiO_2$ microspheres with no PAMAM shells around them also produced PdNPs, or the sample labeled here as $SiO_2@$Pd. The formation of PdNPs directly on the $SiO_2$ microspheres is driven by the possible electrostatic interaction between Pd(II) ions and the silanol (Si—OH) groups of the $SiO_2$ microspheres and the subsequent reduction of the Pd(II) ions into supported PdNPs (FIG. 5). However, the number of PdNPs formed in this case was visibly much fewer compared to those on the $SiO_2@$Pd-PAMAM dendrimer core-shell microspheres, indicating the importance of the PAMAM dendrimers. Furthermore, and most importantly, the PdNPs in $SiO_2@$Pd appeared to be slightly bigger in size, with sizes up to ~3.37±1.40 nm. In addition, their particle size distribution appeared more polydispersed (see FIG. 5) compared to those in $SiO_2@$Pd-PAMAM dendrimer core-shell microspheres.

The formation of PdNPs in $SiO_2@$Pd-PAMAM dendrimer core-shell microspheres was confirmed by UV-vis spectroscopy, powder X-ray diffraction (XRD), and elemental analyses. The UV-vis spectrum of $SiO_2@$Pd-PAMAM core-shell microspheres showed an absorption band at ~229 nm (FIG. 6A) corresponding to PdNPs (Huang et al. (2009) Chem. Commun., 31:4687-4689; Teranishi et al. (1998) Chem. Mater., 10:594-600). Pd(0) nanoparticles, especially very small ones, have no strong plasmon band in the visible region, and they rather have only broad UV-vis absorption bands near UV region with no discernible peak (Huang et al. (2009) Chem. Commun., 31:4687-4689; Moreno et al. (2011) J. Am. Chem. Soc., 133:4389-4397; Agostini et al. (2010) Langmuir 26:11204-11211; Sadeghmoghaddam et al. (2011) J. Mater. Chem., 21:307-312). The strong and sharp bands in the range of 210-300 nm, particularly at ~210 and ~230 nm, could be due to various MLCT bands of Pd$^{2+}$ complexes (Agostini et al. (2010) Langmuir 26:11204-11211; Sadeghmoghaddam et al. (2011) J. Mater. Chem., 21:307-312). The UV-vis spectra for $SiO_2@$Pd-PAMAM microspheres, in fact, look very similar to the UV-vis spectrum reported for tannin-stabilized Pd(0) nanoparticles (Huang et al. (2009) Chem. Commun., 31:4687-4689).

Furthermore, the wide-angle XRD pattern of the $SiO_2@$Pd-PAMAM microspheres (FIG. 6B) exhibited a broad peak at 39.25° that was attributed to the (111) reflection of Pd (Kim et al. (2003) Nano Lett., 3:1289-1291). The broad XRD peak is to be expected for such small Pd nanoparticles encapsulated within the dendrimers of the $SiO_2@$Pd-PAMAM microspheres. The XRD pattern of the Pd nanoparticles in $SiO_2@$Pd-PAMAM microspheres appears similar to the XRD pattern recently reported for small Pd nanoparticles within mesoporous silica (Jiang et al. (2006) J. Am. Chem. Soc., 128:716-717).

The presence and wt % of Pd in $SiO_2@$Pd-PAMAM core-shell microspheres was further determined by elemental analysis which showed 534 ppm (0.053 wt %) Pd. This was calculated to be 2.5 mmol Pd per gram of SiO2@Pd-PAMAM core-shell microspheres.

Catalytic Studies

The catalytic properties of the $SiO_2@$Pd-PAMAM microspheres were investigated by using the microspheres as catalyst in hydrogenation reaction of various substrates under 10 bar hydrogen pressure and at room temperature (RT) (Table 3). Control experiments involving attempted hydrogenation reaction without any catalyst or with silica microspheres containing no Pd ($SiO_2$ and $SiO_2$@PAMAM) gave almost no reaction or no hydrogenation product. However, the $SiO_2$@Pd-PAMAM microspheres catalyzed the hydrogenation reactions of various substrates well, giving the corresponding hydrogenated products, as confirmed by GC and GC-MS (Tables 3 and 4 and FIG. 7). For instance, the hydrogenation of styrene in the presence of $SiO_2$@Pd-PAMAM core-shell microspheres resulted in ethylbenzene with ~100% conversion in 10 minutes at RT and with a high net rate of 23 880 $h^{-1}$. This showed that the catalytic activity of the $SiO_2$@Pd-PAMAM core-shell microspheres was even higher than that of the very active shaped Pd nanoparticle catalysts in nanoporous silica (Wang et al. (2010) J. Mater. Chem., 20:7834-784). The catalytic efficiency of the $SiO_2$@Pd-PAMAM core-shell microspheres was also compared with commercially available 1 wt % Pd/C catalyst. When the latter was used as catalysts for hydrogenation of styrene under the same conditions, ~100% conversion in 10 minutes was obtained; however, the TOF of the Pd/C catalyzed reaction was found to be about half as much as that of SiO2@Pd-PAMAM core-shell microspheres. Whereas the 1 wt % Pd/C for this reaction yielded a net rate of 10 260 $h^{-1}$ (Table 3, entry 3), the $SiO_2$@Pd-PAMAM core-shell microspheres gave a net rate of 24 000 $h^{-1}$. Furthermore, the $SiO_2$@Pd-PAMAM core-shell microspheres were found to be highly recyclable at least five times with almost no change in their catalytic property giving similar net rate, where as the 1 wt % Pd/C lost its activity, significantly giving a net rate of 4800 $h^{-1}$ after the third recycle (see FIG. 8).

TABLE 3

Hydrogenation of various substrates by $SiO_2$@Pd-PAMAM dendrimer core-shell microsphere catalyst[a].

| Entry | Substrate | Products | Time, min | % Conversion | % Selectivity | TOF, $h^{-1}$ |
|---|---|---|---|---|---|---|
| 1[b] | styrene | ethylbenzene | 10 / 120 | 9 / 80 | ~100 / ~100 | 1812 |
| 2 | styrene | ethylbenzene | 10 | ~100 | ~100 | 24000 |
| 3[c] | styrene | ethylbenzene | 10 | ~100 / 40[d] | ~100 | 10840 / 4800 |
| 4 | phenylacetylene | ethylbenzene | 15 | ~100 | ~100 | 16000 |
| 5 | cyclohexene | cyclohexane | 20 | ~100 | ~100 | 12000 |
| 6 | 1-pentene | pentane | 60 | ~100 | ~100 | 4000 |
| 7 | acetone | isopropanol | 120 | ~100 | ~100 | 2000 |
| 8 | 2,4-pentanedione | 4-hydroxy-2-pentanone | 120 | 95 | ~100[f] | 2000 |
| 9 | styrene oxide | 1-phenylethanol / phenylacetaldehyde | 180 | ~100 | 65[g]:35[h] | 1333 |

TABLE 3-continued

Hydrogenation of various substrates by SiO$_2$@Pd-PAMAM dendrimer core-shell microsphere catalyst[a].

| Entry | Substrate | Products | Time, min | % Conversion | % Selectivity | TOF, h$^{-1}$ |
|---|---|---|---|---|---|---|
| 10 | 4-chloronitrobenzene | 4-chloroaniline | 150 | ~100 | 96 | 1240 |
| 11 | trans-stilbene | 1,2-diphenylethane | 25 | ~100 | ~100 | 10600 |
| 12 | 4-nitrostyrene | 4-ethylaniline | 90 | ~100 [i]<br>35 [j]<br>88 [k] | ~100 [l]<br>~35 [m]<br>~88 [n] | 1240 |

[a] Reaction conditions: substrate: 0.01 mol; methanol: 20 mL; catalyst: 5 mg (0.0053 wt % Pd in the SiO$_2$@Pd-PAMAM dendrimer core-shell microspheres; 10 bar H$_2$ pressure; temperature: 20° C.
[b] Catalyst used was Pd@SiO$_2$.
[c] Catalyst used was 1% Pd/C.
[d] Third recycle of 1% Pd/C.
[e] Temperature: 50° C.
[f] 4-Hydroxypentan-2-one.
[g] 1-Phenylethanol.
[h] Phenylacetaldehyde.
[i] In 15 minutes, all the double bonds were hydrogenated.
[j] In 2.5 hours, 35% of the nitro groups were additionally hydrogenated.
[k] In 8 hours, 88% of the nitro groups were additionally hydrogenated.
[l] In 15 minutes, 100% selectively to 4-nitroethylbenzene product was obtained.
[m] In 2.5 hours, 35% of 4-ethylaniline and 65% 4-nitroethylbenzene were obtained.
[n] In 8 hours, 88% 4-ethylaniline and 12% 4-nitroethylbenzene were obtained.

Another control experiment involving a catalytic reaction with a catalyst prepared by physisorption of premade Pd-PAMAM nanoparticles (or DECs) on the surface of SiO$_2$ microspheres was performed. This catalyst gave significantly lower catalytic activity in catalytic hydrogenation of styrene, and most importantly, it resulted in severe leaching of the DECs into the reaction solution. These microspheres were also found to contain less Pd-PAMAM per silica microsphere. This clearly indicates the advantage of covalent attachment of the Pd-PAMAM DECs onto the SiO$_2$ microspheres in order to increase the stability of the DECs.

To study the scope of the catalytic activity of the SiO$_2$@Pd-PAMAM microspheres, the catalytic hydrogenation reactions of substrates other than styrene were explored (Table 3). For instance, the SiO$_2$@Pd-PAMAM core-shell microspheres catalyzed the hydrogenation of phenylacetylene to ethylbenzene. The hydrogenation of phenylacetylene was found to be slightly slower than that of styrene (Table 3, entry 4). This was, however, to be expected considering the fact that the hydrogenation of phenylacetylene to ethylbenzene goes through two hydrogenation steps, i.e., phenylacetylene to styrene and then styrene to ethylbenzene. The catalyst, nevertheless, still exhibited high catalytic activity and TOF even for such two-step hydrogenation reaction. The hydrogenation of another reactant, cyclohexene, took place with almost ~100% conversion in 20 minutes in the presence of the SiO$_2$@Pd-PAMAM core-shell microspheres under the same reaction condition (Table 3, entry 5). In addition, the SiO$_2$@Pd-PAMAM core-shell microspheres catalyzed n-hexene with ~100% conversion in 60 minutes (Table 3, entry 6). More interestingly, although ketones undergo hydrogenation rather relatively slowly (Deshmukh et al. (2008) Catal. Lett., 120:257-260), the SiO$_2$@Pd-PAMAM core-shell microspheres catalyzed the hydrogenation of acetone and acetylacetone efficiently and with high TOF. The catalytic hydrogenation of acetone with SiO$_2$@Pd-PAMAM core-shell microspheres gave a sole product, isopropanol, with ~100% conversion in 2 hours at 50° C., whereas the catalytic hydrogenation acetylacetonate gave 4-hydroxypentan-2-one with 95% conversion in 2 hours (Table 3, entries 7 and 8).

The hydrogenation of styrene oxide into 1-phenylethanol—an important compound in the fragrance industry (Telkar et al. (2004) Appl. Catal. A: Chem., 273:11-19)—was also demonstrated using the SiO$_2$@Pd-PAMAM core-shell microspheres as catalyst. The reaction gave ~100% conversion in 3 hours, yielding 65% of 1-phenylethanol and 35% of phenylacetaldehyde products (Table 3, entry 9). The catalytic activity of the SiO$_2$@Pd-PAMAM microspheres was also tested with 4-chloronitrobenzene—a less reactive compound to undergo hydrogenation (Meng et al. (2010) J. Catal., 269:131-139). The SiO$_2$@Pd-PAMAM core-shell microspheres catalyzed the reaction with 100% conversion and 96% selectivity to 4-chloroaniline product in 2.5 hours and at a slightly elevated temperature of 50° C. (Table 3, entry 10). The SiO$_2$@Pd-PAMAM core-shell microspheres were also found to catalyze the hydrogenation of trans-stilbene to generate 1,2-diphenylethane successfully with ~100% conversion in 25 minutes (Table 3, entry 11). The SiO$_2$@Pd-PAMAM core-shell microspheres' selectivity to catalytically hydrogenate different functional groups was tested using 4-nitrostyrene, which has a nitro group and a vinyl group that can undergo hydrogenation (Table 3, entry 12). In the initial period of the reaction, only the vinyl groups underwent catalytic hydrogenation in the presence of the SiO$_2$@Pd-PAMAM core-shell microspheres almost completely in ~15 minutes. Then, the nitro groups followed and underwent hydrogenation into amine groups almost completely in ~2.5 hours.

The reusability of $SiO_2$@Pd-PAMAM core-shell microspheres as catalyst was tested using styrene hydrogenation as a model reaction (Table 4). This was performed by collecting the $SiO_2$@Pd-PAMAM core-shell microspheres from the preceding reaction via simple centrifugation and then reusing them as catalyst in the next cycle. The $SiO_2$@Pd-PAMAM core-shell microspheres were proven to be effectively recyclable catalysts at least in five cycles with barely losing their catalytic activities. Their TOF remained between 23,780 and 23,880 $h^{-1}$ after five cycles. On the other hand, the $SiO_2$@Pd microspheres (control sample), which contained no PAMAM on their shells, also catalyzed the hydrogenation of styrene to ethylbenzene with similar catalytic efficiency, giving 98% conversion in 10 minutes and 23,750 $h^{-1}$ TOF in the first cycle. However, they quickly lost their catalytic activities after recycling, giving only 61, 54, and 40% conversions and 14,783, 13,086, and 9693 $h^{-1}$ TOFs, respectively, after the first, second and third cycles (Table 5). These TOF values were significantly lower than the corresponding values obtained for the $SiO_2$@Pd-PAMAM core-shell microspheres.

TABLE 4

Results for the recycle catalytic reactions for $SiO_2$@Pd-PAMAM core-shell microsphere catalysts for the hydrogenation of styrene[a].

| entry | recycle no. | t, min | % conv | % selectivity[b] | net rate, $h^{-1}$ [c] |
|---|---|---|---|---|---|
| 1 | 0 | 7 | 76.5 | ~100 | 23 880 |
| 2 | 1 | 7 | 76.5 | ~100 | 23 880 |
| 3 | 2 | 7 | 76.2 | ~100 | 23 810 |
| 4 | 3 | 7 | 76.2 | ~100 | 23 810 |
| 5 | 4 | 7 | 76.2 | ~100 | 23 810 |
| 6 | 5 | 7 | 76.0 | ~100 | 23 780 |

[a]Reaction conditions: styrene: 0.01 mol; methanol: 20 mL; catalyst: 5 mg (0.0053 wt % Pd in the $SiO_2$@Pd-PAMAM core-shell microspheres); 10 bar$H_2$ pressure; temperature: 20° C.; reaction time: 10 minutes.
[b]Selectivity to ethylbenzene product.
[c]The net rate was calculated by dividing the mmol of product formed in 7 minutes by mmol of catalyst used in the reaction and then normalizing all the results for 1 hour for comparison purposes. It is worth mentioning that the hydrogenation reaction of styrene with the catalyst is extremely fast, getting almost into completion within 10 minutes of reaction time. The reaction was monitored by measuring the drop in $H_2$ pressure in the reactor due to the hydrogenation reaction as precisely as possible using a pressure gauge that comes with the Parr reactor. Furthermore, the reaction times were collected with stop watches as precisely as possible. Moreover, because of the unavoidable slight loss of catalyst during recovery, the amount of reactant used in the next cycle was scaled down accordingly in order to maintain the reactant/catalyst ratio as constant as possible in all of the five cycles for comparison purposes.

TABLE 5

Catalytic activities of $SiO_2$@Pd microspheres in multiple cycles of catalytic test[a].

| entry | recycle no. | % conv | % selectivity[b] | net rate, $h^{-1}$ [c] |
|---|---|---|---|---|
| 1 | 0 | 98 | ~100 | 23 750 |
| 2 | 1 | 61 | ~100 | 14 783 |
| 3 | 2 | 54 | ~100 | 13 086 |
| 4 | 3 | 40 | ~100 | 9 693 |
| 5 | 4 | 23 | ~100 | 5 573 |
| 6 | 5 | 19 | ~100 | 4 604 |

[a]Reaction conditions: substrate: 0.01 mol; methanol: 20 mL; catalyst: 5 mg (0.05 wt % Pd in the $SiO_2$@Pd microspheres; 10 bar $H_2$ pressure; temperature: 20° C.; and reaction time: 10 minutes.
[b]Selectivity to ethylbenzene product.
[c]The net rate was calculated by dividing the mmol of product formed in the specified time by mmol of catalyst used in the reaction and then normalizing all the results for 1 hour for comparison purposes.

Furthermore, leaching tests for the $SiO_2$@Pd-PAMAM core-shell microspheres in the catalytic reactions were conducted. The catalytic reaction of the supernatant, after separating the $SiO_2$@Pd-PAMAM core-shell microspheres from the reaction mixture, gave only 1% styrene conversion in an additional 10 minutes, indicating the "true" heterogeneous catalytic nature of the $SiO_2$@Pd-PAMAM core-shell microspheres. This result was corroborated by ICP-OES analysis of palladium in the reaction mixture after the first, third, and fifth reaction cycles, which showed <1 ppm palladium in the solutions.

Notably, under the experimental conditions the hydrogenation reaction performed using the $SiO_2$@Pd-PAMAM microspheres as catalysts, the arene groups of styrene and the substrates did not undergo hydrogenation, while the vinyl and nitro functional groups did. This may be because the arene groups are too big to penetrate through DENs and reach to the Pd nanoparticles or the arene groups do not undergo catalysis with the $SiO_2$@Pd-PAMAM microsphere catalysts under the conditions employed. Whatever the case might be, this difference in reactivity between the vinyl and arene groups can be taken advantage of and utilized to perform selective catalysis of only vinyl or nitro groups in the presence of arene groups. Indeed, it has been shown that the rational design of the periphery of dendrimers allows preferential size-dependent selective hydrogenation of smaller α-allylic alcohols (Oh et al. (2005) Langmuir 21:10209-10213).

It is also worth noting that the conditions employed for hydrogenation reaction, 10 atm $H_2$ pressure, is relatively, but not surprisingly, high. There are literature reports on hydrogenation reactions using lower $H_2$ pressure, for instance 100 Torr of $H_2$ (~0.13 atm) (Molero et al. (2005) Catal. Lett., 101:145-149; Cremer et al. (1996) J. Am. Chem. Soc., 118: 2942-2949). However, in many of these cases, the reactions are often done under vacuum and for gas phase hydrogenation of substances such as ethylene. Furthermore, in most of these cases, although the $H_2$ pressure is set to be low, the other gases such as ethylene or argon make up the overall pressure. For instance, ethylene pressures between 50 and 300 Torr and $H_2$ pressures from 45 to 600 Torr at 300 and 475 K were used to do ethylene hydrogetation in gas phase (Molero et al. (2005) Catal. Lett., 101:145-149). In another example, near 1 atm of total pressure of ethylene and $H_2$ was used at 295 K to perform ethylene hydrogenation (Cremer et al. (1996) J. Am. Chem. Soc., 118:2942-2949). It was further reported that at such intermediate pressures of 100 Torr of $H_2$ gas the richest surface chemistry with infrared-visible sum frequency generation (SFG), which was used to monitor the surface vibrational spectrum in situ during ethylene hydrogenation on Pt(111) at 295 K, was obtained. Thus, these low pressures are chosen mainly to perform experiments of these types in ultrahigh vacuum (UHV) systems to probe reaction mechanisms.

On the other hand, experiments herein using very low $H_2$ pressure are not very feasible because the alkene is in liquid form and the reaction mixture is in solution phase. In hydrogenation of alkenes in liquid phase, the hydrogen pressures are often set to a much higher pressures than 100 Torr to get reasonable yield/TOF (Oyamada et al. (2011) J. Org. Chem., 7:735-739; Xu et al. (2011) J. Adv. Synth. Catal., 353:1260-1264). For instance, 0.15 MPa or 1.48 atm (a much higher pressure than 100 Torr) was used for hydrogenation of various organic compounds (Oyamada et al. (2011) J. Org. Chem., 7:735-739). They obtained (the highest) TON of 2700 in 1.5 hours (or a TOF value of 1800 $h^{-1}$), which was much lower than the one obtained here, which was 24 000 however, the pressure used here case was high, i.e., 9.8 atm. In another example, 1.5 MPa or 14.8 atm $H_2$ pressure was used for hydrogenation of various nitroaromatices in solution phase using Pt nanoparticles (Xu et al. (2011) J. Adv. Synth. Catal., 353:1260-1264). Although the H$_2$ pressure used in their case was actually higher than the one used here, the conversion of the nitro groups in their catalytic reactions also reached ~90-100% only in 1-10 hours.

To further evaluate the catalytic activities of the SiO$_2$@Pd-PAMAM core-shell microspheres, the hydrogenation of styrene under lower pressure (1 atm or 1.01 bur) of H$_2$ was also conducted in the presence of the SiO$_2$@Pd-PAMAM core-shell microspheres. Only 7% conversion was obtained in 4.5 minutes. Soon after this, the H$_2$ pressure dropped to 0.27 atm and the reaction barely continued afterwards. When setting the pressure in the reaction mixture to 1 atm again, the reaction gave 6% more reactant conversion, followed by a significant drop in the H$_2$ pressure as well as in the reaction rate.

In addition, the net rate of SiO$_2$@Pd-PAMAM core-shell microsphere catalyst (i.e., ~24 000 h$^{-1}$) was compared with values reported for similar catalysts in the literature. For instance, compared with the catalytic activity of nanoporous silica encapsulated Pd nanoparticle catalysts (Wang et al. (2010) J. Mater. Chem., 20:7834-784) and that gave net rate of 2800-5400 h$^{-1}$, the catalytic activity of the SiO$_2$@Pd-PAMAM core-shell microspheres was higher. Furthermore, compared with the highest TOF value of 4.37 s$^{-1}$ for Pd catalysts (Mastalir et al. (2003) J. Catal., 220:372-381), the one obtained herein for SiO$_2$@Pd-PAMAM core-shell microspheres (~24 000 h$^{-1}$) was again higher. Typical TOF values ranged from 4.3 to 66.2 s$^{-1}$ (which were 258 to 3972 h$^{-1}$ when converted into h-1 for comparison purposes) for different silica-supported palladium nanomaterials were reported (Mekasuwandumrong, O. (2009) Ind. Eng. Chem. Res., 48:2819-2825). This result also showed that the catalytic activity of the SiO$_2$@Pd-PAMAM microspheres was higher than that of these Pd catalysts. In other work, ~100% conversion of alkene in much longer reaction time of 40 minutes, but under much lower reaction pressure than those used herein, was reported (Jackson, et al. (1996) Appl. Catal. A: Gen., 134:91-99). A catalyst with 2% Pd on Davisil 643 was also reported to catalyze hydrogenation at 1 bar pressure of alkyne into alkene almost completely in 10 minutes, with further conversion of the resulting alkene into alkane after ~20 minutes more (Nijhuis et al. (2003) Appl. Catal. A: Gen., 238:259-271). Comparing the above results, it is clear that the SiO$_2$@Pd-PAMAM microsphere catalysts perform better. In fact, only in case of Pt nanoparticles, does one find a much higher net rate (i.e., 65 041 h$^{-1}$ for hydrogenation of nitrobenzene) than those obtained herein (Pasricha et al. (2009) Small 5:1467-1473).

EXAMPLE 2

Experimental

Materials and Reagents

Anhydrous ethanol, aqueous ammonium hydroxide solution (28%), citric acid and sodium hydroxide (Certified, A.C.S.) were purchased from Fisher Scientific. 3-Aminopropyltriethoxysilane (APTS, 99%) was obtained from Acros Organics. Tetraethyl orthosilicate (TEOS, 98%), sodium tetrachloropalladate(II) (Na$_2$PdCl$_4$), polyvinylpyrrolidone (PVP, MW=~55000), and dimethyl sulfoxide (DMSO) were obtained from Sigma-Aldrich. Polyvinylpyrrolidone K15 (PVP K15, Mw~10000) was purchased from Fluka. Unless mentioned otherwise, Millipore water with a high resistivity of 18 M-Ω was used for the synthesis of the materials.
Synthesis of Pd nanoparticles (Pd NP)

Octahedral shaped Pd-NPs were synthesized as reported (Lim et al. (2007) Angew. Chem. Int. Ed., 46:9279). In a typical synthesis, PVP and citric acid (275 mg) were dissolved in water (8.0 mL) in a 25-mL, three-necked flask containing a Teflon-coated magnetic stir bar and refluxed at 90° C. in air with stirring. Sodium tetrachloropalladate(II) (7.3 mM) was dissolved in water (3.0 mL) at room temperature, and this aqueous solution was then rapidly added into the flask with a pipette. The molar ratio of Na$_2$PdCl$_4$ to PVP was kept at 1:5 in all the experiments. The reaction mixture was heated at 90° C. in air for 3 hours to obtain 5 nm Pd-NP or 26 hours to obtain 20 nm Pd-NP.
Synthesis and Surface Functionalization of Monodisperse Silica Nanospheres (SiO$_2$)

Monodisperse silica nanospheres were synthesized by following the Stober method (Stober et al. (1968) J. Colloid Interface Sci., 26:62). Typically, 6.2 mL of TEOS was added to 6.5 mL of ammonium hydroxide solution (28 wt %) in 100 mL of ethanol and 7.1 mL of Millipore water under stirring to hydrolyze TEOS. After 15 hours of stirring, a colloidal solution of silica nanospheres of 250 nm diameter was obtained. After washing with ethanol through centrifugation and redispersion two times, 1 g of the silica nanospheres was transferred into a mixture of isopropanol (180 mL) and APTS (1.5 mL) and stirred at 80° C. for 2 hours to functionalize the silica surface with amino groups. After washing with isopropanol twice via centrifugation and decantation, —NH$_2$ terminated silica nanospheres were obtained. The resulting —NH$_2$ terminated silica nanospheres were then dispersed in de-ionized water (20 mL).
Synthesis of SiO$_2$/Pd-NP Core-Shell Nanospheres Pd-NP were adsorbed onto the —NH$_2$ functionalized silica nanospheres by adding the above —NH$_2$ terminated SiO$_2$ nanospheres (4.8 mL) into the solution containing Pd-NP (12 mL, 7.3 mM on the basis of Pd atoms) that was further diluted in 125 mL de-ionized water under sonication. The solution was allowed to equilibrate for 10 minutes. The colloidal solution was then centrifuged and the precipitate was washed with water once and dispersed in de-ionized water (8.6 mL). This gave a colloidal solution of SiO$_2$/Pd-NP core-shell nanospheres.
Synthesis of SiO$_2$/Pd-NP/SiO$_2$ Core-Shell-Shell Nanospheres The solution containing SiO$_2$/Pd-NP nanospheres from above (2 mL) was dispersed in a mixture of ethanol (100 mL), water (12.5 mL), and ammonium hydroxide solution (5 mL). Then, 0.25 mL TEOS was added into this solution to encapsulate the SiO$_2$/Pd-NP with a silica shell. After 12 hours of stirring, the solution was centrifuged and the precipitate was washed with ethanol. The final precipitate was dispersed in de-ionized water (25 mL) giving a colloidal solution of SiO$_2$/Pd-NP/SiO$_2$ core-shell-shell nanospheres.
Etching of Silica Shell of SiO$_2$/Pd-NP/SO$_2$ Nanospheres To etch the silica shell into nanoporous silica (Porous-SiO$_2$), 1 g of PVP K15 was dissolved in the solution containing SiO$_2$/Pd-NP/SiO$_2$ nanospheres (25 mL) under stirring. This solution was then refluxed at 100° C. for 3 hours. After cooling down the solution to room temperature, NaOH (0.8 g) was added into the solution and stirred for 3 hours under ambient condition to etch the silica shell. After centrifugations and washing with distilled water and ethanol three times in each case, SiO$_2$/Pd-NP/Porous-SiO$_2$ core-shell-shell nanospheres were obtained. The particles were finally dispersed in ethanol for TEM imaging and in methanol for catalysis studies.

Catalytic Hydrogenation Reaction

The catalytic hydrogenation reactions were carried out in a 250 mL high-pressure reactor supplied by Parr Instrument Company. The reactor was equipped with a heating arrangement, overhead stirrer, thermowell, and pressure gauge as well as transducer, gas inlet, gas outlet, and sampling valve. The reactor has the provision to set temperatures and agitation speeds through controllers. In a typical hydrogenation reaction, a known amount of substrate was dissolved in solvent and the etched $SiO_2$/Pd-NP/Porous-$SiO_2$ catalyst was charged into the reactor. It should be mentioned that the size of Pd-NP in the $SiO_2$/Pd-NP/Porous-$SiO_2$ used for all catalytic experiments was 5 nm. The relative ratio of substrate to catalyst used is compiled in Table 6. The reactor was flushed thrice with nitrogen and then thrice with hydrogen before every reaction. Hydrogen gas was introduced into the reactor to the desired pressure after setting the stirrer to slow stirring rate for uniform heat and reactant distribution. After attaining the desired temperature, the reaction was initiated by increasing the agitation speed to 550 rpm. The consumption of hydrogen gas due to the reaction was monitored from the pressure drop in the reactor. The reaction was stopped when the gas consumption ceased. The reactor contents were cooled, and the liquid sample was analyzed with gas chromatography (GC), GC-MS, and $^1$H NMR spectroscopy.

Heck Coupling Reaction

In a 25 mL round bottom flask, $SiO_2$/Pd-NP/Porous-$SiO_2$ catalyst (10 mg) was dispersed in DMSO (10 mL) via sonication. Styrene (1.3 mmol), iodobenzene (1.0 mol), and $Et_3N$ (1.5 mmol) were then added and the reaction was stirred at 120° C. The formation and yield of trans-stilbene were monitored by GC-MS, GC and $^1$HNMR (Mahesh et al. (2005) J. Org. Chem., 70:4118).

Instrumentations

Nitrogen gas adsorptions were measured with Micromeritics Tristar 3000 volumetric adsorption analyzer after degassing the samples at 160° C. for 12 hours. The TEM images were taken by using an FEI Tecnai T-12 S/TEM instrument. The samples for TEM analysis were prepared by sonicating the samples in ethanol for 3 min, casting a few drops of the solution on a formvar-carbon coated copper grid and letting the solution dry under ambient conditions. The GC was performed on Agilent HP 6850 containing a flame ionization detector and an HP-1, MS 30 m×0.200 mm×0.25 µm capillary column. The GC-MS experiment was conducted with HP-5890 equipped with 5972 MSD and an HP-5 MS 50 m×0.200 mm×0.33 µm capillary column. The $^1$H NMR spectra of the reaction mixtures were obtained with a Bruker DPX-300 NMR spectrometer.

Results

The $SiO_2$/Pd-NP/Porous-$SiO_2$ core-shell-shell nanospheres, consisting of shaped Pd nanoparticles (Pd-NP) sandwiched between a silica nanosphere core and a nanoporous silica shell, were prepared in four steps as illustrated in FIG. 9. In step 1, silica nanospheres were synthesized and used as a support core material for Pd-NP. To perform this, nearly monodisperse, 250-nm silica nanospheres ($SiO_2$) were synthesized using the Stober method, and their surfaces were modified with 3-aminopropyltrimethoxysilane (APTS) (Stober et al. (1968) J. Colloid Interface Sci., 26:62; Narayanan et al. (2005) J. Phys. Chem. B, 109:12663). Then, octahedral shaped, ~5 nm (or ~20 nm) Pd-NP were chemisorbed on the aminopropyl-terminated silica nanospheres in Step 2, resulting in $SiO_2$/Pd-NP core-shell nanospheres. The octahedral Pd-NP were synthesized by reducing different concentration of aqueous solution of Pd salt with citric acid (FIG. 10; Lim et al. (2007) Angew. Chem. Int. Ed., 46:9279). In Step 3, the $SiO_2$/Pd-NP core-shell nanospheres were coated with a silica shell producing $SiO_2$/Pd-NP/$SiO_2$ core-shell-shell nanospheres. The deposition of the silica shell around the $SiO_2$/Pd-NP was performed by the sol-gel process using tetraethyl orthosilicate (TEOS) as the silica source in ethanol (Lu et al. (2002) Nano Lett., 2:785). Finally, in Step 4, controlled etching of the outer silica shell with an aqueous NaOH solution generated a nanoporous silica shell and $SiO_2$/Pd-NP/Porous-$SiO_2$ core-shell-shell nanospheres. By changing the etching conditions, particularly the etching time, the pore structure of the silica shell was tuned or optimized.

Figure 10:
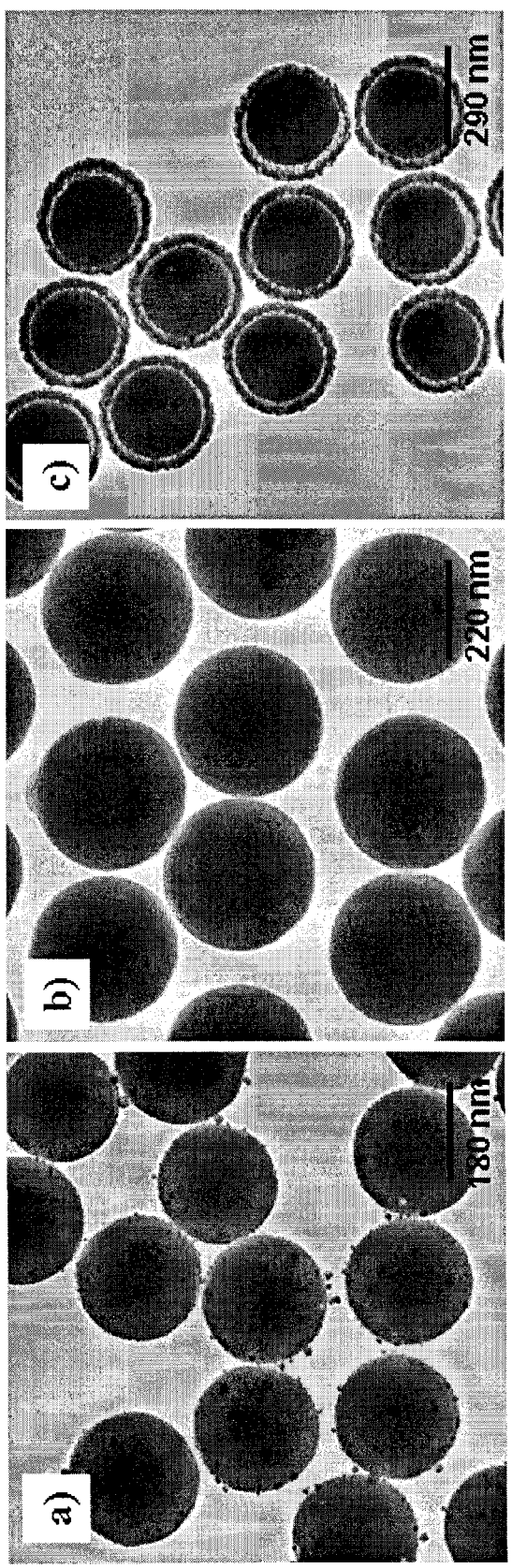
Figure 10:
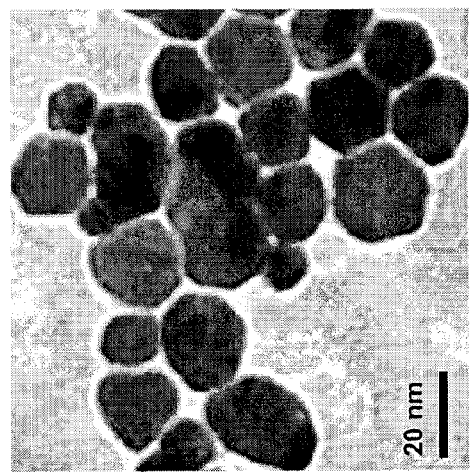

Representative TEM images of some of the materials described in FIG. 9 are shown in FIGS. 10-12. The more magnified TEM images in FIG. 11 and the less magnified TEM images in FIG. 10 show that the 20 nm Pd-NP are randomly dispersed around the $SiO_2$ nanospheres. Then, the coating of silica shell with controlled thickness around the Pd-NP is achieved reproducibly by stirring the $SiO_2$/Pd-NP nanospheres in different concentrations of TEOS as shown in FIGS. 11B and 12. The thickness of the silica shell was found to depend linearly on the amount of TEOS used for a given $NH_4OH$ concentration and deposition time. For instance, TEM images show an increase of thickness of the silica shell from 20 nm to 100 nm upon increasing the amount of TEOS from 0.1 mL to 0.6 mL in the solution (FIG. 13). Interestingly, when the amount of TEOS was increased to 0.6 mL, in addition to thicker silica shells, some smaller Pd-NP/$SiO_2$ type core-shell nanospheres also formed (FIG. 13). The use of an optimum amount (0.25 mL) of TEOS guaranteed the formation of a uniform 50-nm-thick silica shell (FIG. 11). In addition to the amount of TEOS, it is worth mentioning that the thickness of the silica shell can also depend on the reaction time and concentration of $NH_4OH$. Higher concentration of TEOS or large amount of $NH_4OH$ can lead to thicker silica shells for a given deposition time (Stober et al. (1968) J. Colloid Interface Sci., 26:62).

The nanoporous silica shell around the Pd-NP was achieved by selective etching of the outer silica shell with NaOH solution in the presence of PVP (Zhang et al. (2008) Nano Lett., 8:2867). PVP was added in this step not to stabilize the Pd-NP but rather to enable uniform in depth etching or continuous exfoliation of the inner part of the silica nanospheres. Without PVP, only the outermost layer of the silica shell will get etched predominantly resulting in non-uniformly etched or a rather non-porous silica shell. The PVP helps the uniform etching of the cores of silica or slows the etching of the outer surface by forming strong interaction with the outermost surface of the particles (Zhang et al. (2008) Nano Lett., 8:2867). FIGS. 9 and 12 show a more magnified, a less magnified and a large area TEM image, respectively, of $SiO_2$/Pd-NP/Porous-$SiO_2$ nanospheres that were etched for 120 minutes. As can be seen from these TEM images, multiple Pd-NP are sandwiched between a solid silica nanoparticle core and a nanoporous silica shell. In addition to PVP, changing the etching time allows tuning the pore sizes and structures of the porous silica shell. For instance, upon increasing the etching time from 50 to 100 minutes, $SiO_2$/Pd-NP/Porous-$SiO_2$ core-shell-shell nanospheres with concentric pores around the Pd-NP formed (FIG. 14). Longer etching times of 150 minutes resulted in complete dissolution or removal of the second silica shell. $SiO_2$/Pd-NP/Porous-$SiO_2$ nanospheres with a uniform nanoporous shell were obtained by using optimal etching time of 80 minutes. The resulting etched $SiO_2$/Pd-NP/Porous-$SiO_2$ core-shell-shell nanospheres were readily dispersible in water and remained stable for several months. In addition to 20 nm Pd-NP, the synthesis was proven to work well for 5 nm Pd-NP producing $SiO_2$/Pd-NP/Porous-$SiO_2$ core-shell-shell nanospheres (FIG. 15).

The nanoporosity of the silica shell of the $SiO_2$/Pd-NP/Porous-$SiO_2$ nanospheres was confirmed by nitrogen gas adsorption. FIG. 16 shows representative nitrogen gas adsorption/desorption isotherms with the corresponding pore size distribution of the sample displayed in the inset for $SiO_2$/Pd-NP/Porous-$SiO_2$ sample etched for 80 min. A Brunauer-Emmett-Teller (BET) surface area and single-point total pore volume of 115 $m^2$ $g^{-1}$ and 0.31 $cm^3$ $g^{-1}$, respectively, were obtained for this sample. The values obtained for surface area and pore volume per unit mass of this sample are large, especially when considering the fact that the sample has relatively larger mass due to its solid silica core as well as a heavy metal, Pd. For instance, the surface areas of mesoporous materials which have a fully porous structure throughout and contain no heavy metal typically give surface areas of ~200-1,000 $m^2$/g and pore volumes of ~0.5-1 $cm^3$/g depending on the type of synthetic method used (Sharma et al. (2007) Angew. Chem. Int. Ed., 46:2879; Man et al. (2008) J. Mol. Catal. A, 288:1). The average BJH pore diameter calculated from desorption branch of the nitrogen isotherm for $SiO_2$/Pd-NP/Porous-$SiO_2$ nanospheres etched for 80 minutes was found to be 11.3 nm. Gas adsorption measurement of $SiO_2$/Pd-NP/Porous-$SiO_2$ nanospheres etched for slightly longer time of 100 minutes was also performed (FIG. 17). An increase in the average BJH pore diameter and a broader pore size distribution were observed upon increasing the etching times. For instance, the pore diameters for the sample etched for 100 minutes gave a rather broad pore size distribution with pores prominently>~18 nm (FIG. 17). This was consistent with TEM images (FIG. 14) which showed a more porous silica shell and slightly bigger pore sizes as the etching time increases.

The Pd-NP assembled within the $SiO_2$/Pd-NP and $SiO_2$/Pd-NP/Porous-$SiO_2$ core-shell-shell nanospheres were also characterized by X-ray powder diffraction (XRD) (FIG. 18). The results showed that diffraction intensities of the Pd-NP were relatively low and had pronounced peak broadening. This is to be expected for small nanoparticles and more so for those embedded within silica shell. Nevertheless, the diffraction patterns clearly indicated the presence of Pd and no significant palladium oxide phase (Xiong et al. (2005) J. Am. Chem. Soc., 127:17118). This, however, does not necessarily rule out the possibility of the presence of a monolayer of PdO on the Pd nanoparticles. Further comparison of the diffraction pattern of Pd-NP in the $SiO_2$/Pd-NP core-shell nanospheres with those in the $SiO_2$/Pd-NP/Porous-$SiO_2$ core-shell-shell nanospheres indicated essentially no change in Pd nanocrystal size as calculated by Scherrer equation. This can also be clearly seen by the absence of no further broadening of diffraction peaks of the Pd-NP after the deposition of the silica shell around Pd-NP. Therefore, it can be concluded from the XRD analysis that the Pd-NP encapsulated within the nanoporous silica shell remained stable and are most likely pure Pd and not PdO. The latter was also supported by the fact that the $SiO_2$/Pd-NP/Porous-$SiO_2$ material showing active catalytic activity in hydrogenation and C—C coupling reactions; i.e. Pd but not PdO is expected to show such catalytic activity).

Styrene hydrogenation (Lan et al. (2009) Chem. Eur. J., 15:3670; Deshmukh et al. (2008) Angew. Chem. Int. Ed., 47:8615; Huang et al. (2004) Angew. Chem. Int. Ed., 43:1397) was used as a model reaction to explore the catalytic activity of the encapsulated Pd-NP in the $SiO_2$/Pd-NP/Porous-$SiO_2$ core-shell-shell nanospheres (Table 6). In a control experiment where no Pd-NP was present (or upon using the silica nanospheres or etched silica nanospheres), the hydrogenation reaction did not occur. However, when $SiO_2$/Pd-NP/Porous-$SiO_2$ core-shell-shell nanospheres etched for 80 minutes were introduced into the reaction mixture, the reaction proceeded even at room temperature and 20 bar $H_2$ pressure giving ethylbenzene as the sole product. Interestingly, the styrene hydrogenation reached almost ~100% reactant conversion within 25 minutes at room temperature. In this catalytic reaction, the turn-over-frequency (TOF), defined as mol of styrene converted per total mol of metal per hour, reached 5000 $h^{-1}$. This high TOF suggests the existence of high catalytic efficiencies for Pd-NP encapsulated within the nanoporous silica shell in the $SiO_2$/Pd-NP/Porous-$SiO_2$ core-shell-shell nanospheres. Comparison of the catalytic efficiencies or TOF values of the instant catalyst with respect to other previously reported Pd catalysts or conventional commercial catalysts was a bit difficult to do precisely because of the different reaction conditions, materials and substrates employed in the different cases as well as the absence of complete catalysis data in some of the previous reports (Lan et al. (2009) Chem. Eur. J., 15:3670; Park et al. (2006) Synthesis, 3790; Wilson et al. (2006) J. Am. Chem. Soc., 128:4510; Mukherjee et al. (2008) J. Nanopart. Res., 10:429; Ruta et al. (2008) J. Phys. Chem. C, 112:13635; Kidambi et al. (2004) J. Am. Chem. Soc., 126:2658). However, the data was compared with at least those reported complete catalytic data. For instance, the TOF value for hydrogenation of styrene at ~20 bar $H_2$ pressure and at room temperature obtained for $SiO_2$/Pd-NP/Porous-$SiO_2$ is three times higher than that for one of the most efficient polymer supported Pd-catalysts reported for similar reaction at a higher temperature of 35° C. and 1 atm $H_2$ pressure (Lan et al. (2009) Chem. Eur. J., 15:3670). In another work, a yield of 98% in 1.5 hours for reactant to Pd catalyst ratio of 2:1 at room temperature and 1 atm $H_2$ pressure was reported while in the instant case a ~100% yield in 0.5 hour for substrate to catalyst ratio of 2000:1 at room temperature and 20 bar $H_2$ pressure for a similarly reacting compound was obtained (Park et al. (2006) Synthesis, 3790). This means a 3000 times greater TOF value for the catalyst although a higher hydrogen pressure using the instant methods.

Without being bound by theory, the high TOF of the catalytic activity of $SiO_2$/Pd-NP/Porous-$SiO_2$ nanospheres was probably a result of one or more of the following: (1) the stability (or absence of aggregation) of the Pd-NP by the virtue of the nanoporous silica shell around them; (2) the high surface area of the smaller size of Pd nanoparticles; (3) the presence of stable Pd-NP with naked surface (or poorly bound surface ligands around them); (4) the presence of many nanoparticles per each silica nanosphere support; (5) the faceted nature or octahedral shape of the nanoparticles; shaped nanoparticles often give higher catalytic activities compared to their spherical counterparts (Sun et al. (2002) Science 298:2176); and (6) an easy access of reactants to the surfaces of Pd-NP through the nanoporous silica shell.

TABLE 6

Hydrogenation of various substrates by $SiO_2$/Pd-NP/Porous-$SiO_2$ core-shell-shell nanosphere catalysts. [a]

| Substrate | Product | t [h]/T [° C.] | Conv. [%] [b] | Sel. [%] [c] | TOF [$h^{-1}$] |
|---|---|---|---|---|---|
| (styrene) | (ethylbenzene) | 0.5/25 | 100 | 100 | 5181 |

TABLE 6-continued

Hydrogenation of various substrates by SiO$_2$/Pd-NP/Porous-SiO$_2$ core-shell-shell nanosphere catalysts. [a]

| Substrate | Product | t [h]/T [° C.] | Conv. [%] [b] | Sel. [%] [c] | TOF [h$^{-1}$] |
|---|---|---|---|---|---|
| phenylacetylene | ethylbenzene | 0.5/25 | 100 | 100 | 5407 |
| cyclohexene | cyclohexane | 1/50 | 96 | 100 | 2812 |
| nitrobenzene | aniline | 3/50 | 91 | 100 | 263 |

[a] Reaction conditions: Substrate: 8.73 mmol; methanol: 40 mL; catalyst: 10 mg (3.59 wt. % Pd in the etched SiO$_2$/Pd-NP/Porous-SiO$_2$ nanospheres); 3.9 mol % Pd in the reaction mixture, with respect to mole of reactant and 20 bar H$_2$ pressure.
[b] Percent conversion of the reactant to product(s).
In all the cases, only one type of hydrogenated product was obtained, making the catalytic selectivity 100%;
[c] Selectivity to a particular hydrogenated product.

To study the scope of the catalytic activity of the encapsulated Pd-NP of the SiO$_2$/Pd-NP/Porous-SiO$_2$ nanospheres, hydrogenation reactions of some other compounds were also explored. Table 6 summarizes the catalytic activity of the porous SiO$_2$/Pd-NP/Porous-SiO$_2$ nanospheres in the hydrogenation of these other compounds. For instance, hydrogenation of phenyacetylene was achieved efficiently and almost quantitatively in 30 minutes using the SiO$_2$/Pd-NP/Porous-SiO$_2$ core-shell-shell nanospheres as catalyst. Furthermore, SiO$_2$/Pd-NP/Porous-SiO$_2$ nanospheres catalyzed reaction gave selectively only one product, ethylbenzene. Because the hydrogenation of phenylacetylene can form two possible products: styrene and ethylebenzene, this reaction is suitable for studying the degree of catalytic selectivity of hydrogenation. The two-step hydrogenation of phenylacetylene selectively (~100%) into ethylbenzene took place only in 30 minutes with high TOF in the presence of SiO$_2$/Pd-NP/Porous-SiO$_2$ nanosphere catalyst (Table 6). Furthermore, effective hydrogenation of cyclohexene to cyclohexane also proceeded well in the presence of SiO$_2$/Pd-NP/Porous-SiO$_2$ nanospheres, indicating the applicability of the materials as catalysts for relatively less reactive unsaturated compounds. In addition, the hydrogenation reaction of a more stable nitrobenzene into aniline was obtained in 97% yield after 3 hours reaction time and at a slightly elevated temperature of 50° C. with the SiO$_2$/Pd-NP/Porous-SiO$_2$ nanosphere catalyst. The slightly lower catalytic efficiency of the nanospheres in hydrogenating aniline compared to olefins is in line with the intrinsic lower tendency of nitro groups to undergo hydrogenation compared to olefins (Trapp et al. (2008) Chem. Eur. J., 14:4657). The fact that the encapsulated Pd-NP in SiO$_2$/Pd-NP/Porous-SiO$_2$ showing higher catalytic activities for Pd-catalyzed hydrogenation compared to other materials in similar reactions (Lan et al. (2009) Chem. Eur. J., 15:3670; Park et al. (2006) Synthesis, 3790) could be attributed to the most conducive structure that they have including stable and "naked" Pd-NP that are stabilized and encapsulated within a nanoporous silica shell.

The recyclability of the SiO$_2$/Pd-NP/Porous-SiO$_2$ nanospheres as heterogeneous catalyst was also demonstrated successfully (FIG. 19). Upon completion of the reaction, the SiO$_2$/Pd-NP/Porous-SiO$_2$ nanospheres were recovered from the reaction mixture by simple centrifugation and used in the next reaction run. The recovered nanospheres showed only a very slight decrease in their catalytic activity. The slight loss of catalytic efficiency was most likely due to the loss of catalyst during the handling and centrifugation. The TEM image (FIG. 20) of the SiO$_2$/Pd-NP/Porous-SiO$_2$ nanospheres collected after the fifth successive reaction cycle exhibited no observable change in the structures of the SiO$_2$/Pd-NP/Porous-SiO$_2$ nanoparticles and their nanoporous silica shell. The TEM image (FIG. 20), however, is not high resolution enough to clearly show the Pd-NP. Nevertheless, based on the absence of significant change in catalytic activity, the Pd-NP did not undergo aggregation to form bulk Pd nor changed their structures and shapes after the catalytic reactions.

The catalytic reaction of the supernatant of the reaction mixture after separating the SiO$_2$/Pd-NP/Porous-SiO$_2$ nanospheres from it was also run in order to determine whether leaching of Pd occurred. Only 3% styrene conversion was observed even after 25 minutes reaction time when the supernatant was stirred by itself after removing the SiO$_2$/Pd-NP/Porous-SiO$_2$ nanospheres from it. From this result, it is clear that the nanoporous silica shell has effectively stabilized and prevented the Pd-NP from aggregation and leaching while at the same time leaving their surfaces somewhat "naked" to give high catalytic activity.

In addition to hydrogenation of a series of alkenes, the nanospheres are proved to catalyze the Heck coupling reaction between styrene and iodobenzene forming trans-stilbene with ~100% yield in 12 hours (FIG. 21). Furthermore, the catalyst showed good recyclability in the Heck coupling reaction as well.

This nanocatalyst exhibits several advantages in comparison to conventional catalysts embedded in bulk supports (Mohapatra et al. (2008) Langmuir 24:11276). Firstly, a large number of Pd-NP was incorporated within a given silica support to impart the materials a high catalytic activity per unit mass. Secondly, the nanoporous silica shell around Pd-NP not only provided reactants to reach to the surface of Pd-NP but also hindered their aggregation with neighboring Pd-NP. Finally, the reported nanosphere catalyst could easily be dispersed in reaction solutions while at the same time recoverable with simple centrifugation and recycling after reactions with no significant loss of their catalytic activity.

In summary, SiO$_2$/Pd-NP/Porous-SiO$_2$ core-shell-shell type nanospheres and nanocatalysts were synthesized which contain silica core and nanoporous silica shell with octahedral shaped Pd nanoparticles sandwiched in between the two. The silica core was synthesized by the Stöber method where as the outer nanoporous silica shell was synthesized by the sol-gel process followed by controlled etching in basic solution. This silica shell was permeable enough to let reactants reach to the Pd nanoparticles while at the same time protected them from aggregation. The resulting SiO$_2$/Pd-NP/Porous-SiO$_2$ core-shell-shell nanosphere showed excellent catalytic activity and selectivity in hydrogenation reactions of phenylacetylene, nitrobenzene, and two different types of olefins at room temperature and ambient H$_2$ pressure as well as in C—C bond coupling reaction. This high catalytic activity and selectivity, even at room temperature, was a result of the assembly of 5 nm size octahedral shaped multiple Pd-NP assembled within high surface area core-shell-shell type nanostructured material. Furthermore, the structure of the material allowed Pd-NP to remain stable, even after being recycled multiple times, while maintaining their high catalytic activity. The instant materials are a stable recyclable catalyst in Pd-catalyzed reactions. Furthermore, the synthetic method can be extended to generate other metallic and metal oxide based nanosphere materials and efficient nanocatalysts.

EXAMPLE 3

Experimental

Materials and Reagents

Ethanol (denatured), aqueous ammonium hydroxide solution (28%), citric acid and sodium hydroxide (Certified, A.C.S.) were purchased from Fisher Scientific. 3-Aminopropyltriethoxysilane (APTS, 99%) was obtained from Acros Organics. Tetraethyl orthosilicate (TEOS, 98%), sodium tetrachloropalladate(II) ($Na_2PdCl_4$), polyvinylpyrrolidone (Mw~55000), Birj 30 and zirconium(IV) n-butoxide $Zr(OBu)_4$ were obtained from Sigma-Aldrich. Polyvinylpyrrolidone K15 (Mw~10000) was purchased from Fluka.

Synthesis of Pd Nanoparticles

First, Pd nanoparticles were synthesized by using an optimum molar ratio of 7.3 mM $Na_2PdCl_4$ to 0.13 mM citric acid, and a 5:1 molar ratio of PVP to the Pd precursor in the solution (Lim et al. (2007) Angew. Chem. Int. Ed., 46:9279-9282). In the typical synthesis, 0.40 mol poly(vinylpyrrolidone) (PVP; MW=55,000) and citric acid (1.43 mmol, 0.275 g) were dissolved in water (8.0 mL) in a 25-mL, three-necked flask equipped with a reflux condenser and a teflon-coated magnetic stir bar, and the solution was heated to 90° C. in air with stirring. Sodium tetrachloropalladate(II) (80.3 mmol, 7.3 mM) was dissolved in water (3.0 mL) at room temperature, and this aqueous solution was then rapidly added to the flask with a pipette. The molar ratio of $Na_2PdCl_4$ to the repeating unit of PVP was kept at 1:5 in the experiment. The reaction mixture was heated at 90° C. in air for 3 hours to produce ~5 nm Pd nanoparticles.

Synthesis of $SiO_2$/Pd Core-Shell Microspheres

To prepare $SiO_2$ microsphere-supported Pd nanoparticles, monodisperse silica microspheres were first synthesized as described (Pachon et al. (2008) Appl. Organomet. Chem., 22:288-299; Wang et al. (2010) J. Mater. Chem., 20:7834-7841; Asefa et al. (2008) J. Mater. Chem., 18:5604-5614; Shi et al. (2007) Langmuir 23:9455-9462). The $SiO_2$ microspheres were then functionalized with APTS to form amine-functionalized $SiO_2$ microspheres. The —$NH_2$ functionalized $SiO_2$ microspheres (4.8 mL) was mixed with the solution containing Pd nanoparticles (12 mL, 7.3 mM on the basis of Pd atoms and diluted in 125 mL de-ionized water under sonication) to let the Pd nanoparticles adsob onto the —$NH_2$ functionalized $SiO_2$ microspheres. The solution was allowed to equilibrate for 10 minutes. The colloidal solution was then centrifuged, washed with 10 mL de-ionized water and dispersed in de-ionized water (8.6 mL), giving colloidal $SiO_2$/Pd core-shell microspheres.

Synthesis of $SiO_2$/Pd/$SiO_2$ Core-Shell-Shell Microspheres $SiO_2$/Pd/$SiO_2$ core-shell-shell microspheres were synthesized by successive self-assembly and sol-gel process (Pastoriza-Santos et al. (2004) Phys. Chem. Chem. Phys., 6:5056-5060). The $SiO_2$/Pd microsphere solution from above (2 mL) was dispersed in a mixture of ethanol (100 mL), water (12.5 mL) and aqueous ammonia (5 mL). Then, 0.25 mL TEOS was added into it to let grow $SiO_2$ grow and encapsulate the Pd nanoparticles of $SiO_2$/Pd core-shell microspheres with a $SiO_2$ shell. The product was centrifuged (5,000 rpm for 5 minutes) and the precipitate was washed with 10 ML ethanol. The final precipitate was dispersed in ethanol (25 mL), resulting in $SiO_2$/Pd/$SiO_2$ core-shell-shell microspheres.

Synthesis of $SiO_2$/Pd/$SiO_2$/$ZrO_2$ Core-Shell-Shell-Shell Microspheres

A colloidal solution $SiO_2$/Pd/$SiO_2$ microspheres (2 mL), water (0.25 mL), Brij 30 (0.25 mL) and ethanol (100 mL) were mixed. After stirring the solution for 40 minutes, $Zr(OBu)_4$ (0.45 mL) was added into the solution. The reaction mixture was further stirred for another 8 hours. The solid product was collected through centrifugation, and then re-dispersed in water (40 mL) and aged for 12 hours. Removal of the organics and crystallization of the resulting zirconia ($ZrO_2$) were achieved by heating the particles in air from room temperature to 850° C. at the rate of 3° C. $min^{-1}$ and keeping it further at 850° C. for 2 hours. The sample was then slowly cooled down to room temperature. This procedure helped the formation of nanoporous $ZrO_2$ shell by removing the Brij 30 surfactants from the surfactant/$ZrO_2$ shell.

Synthesis of $SiO_2$/Pd/$ZrO_2$ Core-Shell-Shell Microspheres (hollow $SiO_2$/Pd/$ZrO_2$ Nanoreactors)

The synthesis of hollow $SiO_2$/Pd/$ZrO_2$ core-shell-shell microspheres was accomplished by removing the inner $SiO_2$ shells of $SiO_2$/Pd/$SiO_2$/$ZrO_2$ core-shell-shell-shell microspheres by stirring them in a solution of 25 mL, 1 M NaOH for 12 hours. After centrifugation of the solution, decantation of the supernatant and washing the precipitate with distilled water and ethanol (3×10 mL each), the hollow $SiO_2$/Pd/h-$ZrO_2$ core-shell-shell microspheres were obtained.

Catalytic Hydrogenation Reaction

The hydrogenation reaction was carried out in a (250 mL) high-pressure stirred reactor supplied by Parr Instrument Company. The reactor was equipped with a heating arrangement, overhead stirrer, thermowell and pressure gauge as well as a transducer, gas inlet, gas outlet, and sampling valve. The reactor has the provision to set temperatures and agitation speeds through controllers. In a typical hydrogenation reaction, a known amount of substrate was dissolved in solvent and the hollow $SiO_2$/Pd/h-$ZrO_2$ core-shell-shell microsphere catalyst was charged into the reactor. For the relative amount of substrates and catalyst used, please refer to Table 7. The reactor was flushed thrice with nitrogen and then thrice with hydrogen. Hydrogen gas was then introduced into the reactor to the 20 bar pressure after setting the reaction temperature; the heater was put under slow stirring rate for uniform heat distribution. After attaining the desired temperature, the reaction was initiated by increasing the agitation speed to 550 rpm. The absorption of hydrogen gas due to reaction was monitored from the pressure drop in the reactor. The reaction was stopped when the gas absorption ceased. The reactor contents were cooled, and the liquid sample was analyzed on an Agilent 6850 Gas Chromatograph (GC) equipped with a HP-1 (1% dimethyl polysiloxane, 30 m length, 0.25 mm internal diameter, 0.25 μm film thickness) with flame ionization detector. The products were further confirmed by using HP-5971 Gas Chromatograph Mass spectrometer (GC-MS) equipped with an HP-5 MS 50 m×0.200 mm×0.33 μm capillary column.

Results

Synthesis of Nanocatalysts

The hollow $SiO_2$/Pd/h-$ZrO_2$ core-shell-shell microspheres and their parent material, $SiO_2$/Pd/$SiO_2$/$ZrO_2$ microsphere, were synthesized by following the synthetic steps illustrated in FIG. 22. In step 1, silica microspheres were used to support pre-made Pd nanoparticles. In a typical synthesis, first nearly monodisperse, 260 nm $SiO_2$ microspheres were synthesized using the Stober method (Stober et al. (1968) J. Colloid Interface Sci., 26:62-69), and their surfaces were modified by 3-aminopropyltrimethoxysilane (APTS) to form aminopropyl-terminated $SiO_2$ microspheres (Pastoriza-Santos et al. (2004) Phys. Chem. Chem. Phys., 6:5056-5060). Then, ~5 nm Pd nanoparticles were covalently attached to the aminopropyl-terminated silica microspheres in step 2. The Pd nanoparticles were synthesized by reducing an aqueous solution of Pd salt with citric acid (Lim et al. (2007) Angew. Chem. Int. Ed., 46:9279-9282). In step 3, the $SiO_2$ microspheres decorated with Pd nanoparticles, denoted as $SiO_2$/Pd, were further coated by a silica shell. The deposition of the silica shell around the $SiO_2$/Pd core-shell microspheres was performed by the sol-gel process using tetraethyl orthosilicate (TEOS) as the silica source in ethanol. This produced $SiO_2$/Pd/$SiO_2$ core-shell-shell type microspheres. In step 4, the $SiO_2$/Pd/$SiO_2$ core-shell-shell microspheres were further coated by surfactant/zirconia ($ZrO_2$) shell (Arnal et al. (2006) Chem. Mater., 18:2733-2739). Briefly, the $SiO_2$/Pd/$SiO_2$ core-shell-shell microspheres were mixed with a solution containing Brij 30 surfactant, zirconium butoxide and some water, and the solution was aged for 12 hours. This produced $SiO_2$/Pd/$SiO_2$/$ZrO_2$ core-shell-shell-shell microspheres having surfactant/$ZrO_2$ shells. The solid $SiO_2$/Pd/$SiO_2$/$ZrO_2$ core-shell-shell-shell microspheres were separated, washed with water and calcined at 1073 K for 2 hours, producing $SiO_2$/Pd/$SiO_2$/h-$ZrO_2$ core-shell-shell-shell microspheres. Finally, controlled etching of the silica shell with an aqueous NaOH solution resulted in the hollow $SiO_2$/Pd/h-$ZrO_2$ core-shell-shell microspheres, which consisted of $SiO_2$ core, $SiO_2$-supported Pd nanoparticle multicores, and a hollow and nanoporous $ZrO_2$ shell around the Pd nanoparticles. Furthermore, by varying the etching times, the second silica shell of $SiO_2$/Pd/$SiO_2$/$ZrO_2$ nanocomposites was removed gradually to produce different types of hollow $SiO_2$/Pd/h-$ZrO_2$ core-shell-shell microspheres.

The TEM images of the $SiO_2$/Pd/h-$ZrO_2$ core-shell microspheres obtained after each synthetic step are shown in FIG. 23. More magnified TEM images are included in FIG. 24. The TEM images show that Pd nanoparticles are randomly dispersed around the surfaces of $SiO_2$/Pd core-shell microspheres (FIGS. 23A and 24A). In the TEM images of $SiO_2$/Pd/$SiO_2$ core-shell-shell microspheres (FIGS. 23B and 24B), a uniform silica shell that is formed from the hydrolysis and condensation of TEOS around $SiO_2$/Pd core-shell microspheres, is clearly visible. The TEM images in FIG. 23B and FIG. 24B, further indicate that a 50 nm thick silica shell is produced for the given ratio of TEOS: $SiO_2$/Pd core-shell microspheres used.

The TEM images (FIGS. 23C and 24C) further display that the successful coating of $ZrO_2$ shell around the $SiO_2$/Pd/$SiO_2$ core-shell-shell microspheres takes place from the hydrolysis and condensation of $Zr(OBu)_4$ in the presence of Brij 30 surfactant. Subsequent calcination in air, followed by etching in basic solution, of the resulting $SiO_2$/Pd/$SiO_2$/$ZrO_2$ core-shell-shell-shell microspheres remove the surfactant and the inner $SiO_2$ shell, respectively, from the material and produce a hollow and nanoporous $ZrO_2$ shell. This gives the $SiO_2$/Pd/h-$ZrO_2$ core-shell-shell microspheres shown in FIGS. 23D and 24D.

Successful formation of $ZrO_2$ shell around the $SiO_2$/Pd/$SiO_2$ core-shell-shell microspheres as well as the thickness of the $ZrO_2$ shell are found to depend on the relative amount of $Zr(OBu)_4$ used in the synthesis (FIGS. 25 and 26). The TEM images in FIGS. 25 and 26A indicate that 0.2 mL of $Zr(OBu)_4$ is not enough to completely or uniformly coat the given amount of $SiO_2$/Pd/$SiO_2$ core-shell-shell microspheres with a $ZrO_2$ shell. It instead results in only some islands of $ZrO_2$ on the surface of $SiO_2$/Pd/$SiO_2$ core-shell-shell microspheres, as seen in FIGS. 25 and 26A. On the other hand, 1 mL of $Zr(OBu)_4$ forms a thick, ~36 nm, $ZrO_2$ shell around $SiO_2$/Pd/$SiO_2$ core-shell-shell microspheres. After more experiments, a range of 0.4-0.5 mL of $Zr(OBu)_4$ is determined to be the most optimum under the experimental conditions as it gives not only a uniform, but also a moderately thick enough $ZrO_2$ shell. From this, 0.45 mL of $Zr(OBu)_4$, which produces a uniform ~18 nm-thick $ZrO_2$ shell, is chosen and used to synthesize the $SiO_2$/Pd/$SiO_2$/$ZrO_2$ core-shell-shell-shell microspheres (FIGS. 23C, 25E, 25F, 26E and 26F). This choice is also made in order 1) to form a thick/stable, and yet porous enough, $ZrO_2$ shell after removing the Brij 30 surfactant from it, and 2) then to allow aqueous NaOH reach and etch the inner $SiO_2$ shell at moderate rate in the subsequent step and form stable hollow $SiO_2$/Pd/h-$ZrO_2$ core-shell-shell microspheres.

As shown in FIG. 27 and FIG. 28, the moderate and continuous etching of the inner silica shell of $SiO_2$/Pd/$SiO_2$/$ZrO_2$ gradually leads to yolk-shell type $SiO_2$/Pd/h-$ZrO_2$ microspheres. This is evidenced by the reduced contrast between the center and the shell of the microspheres in the TEM images as well as the displacement of the $SiO_2$/Pd cores from the center position to the edges in the etched microspheres. The size of the hollow structure of the $SiO_2$/Pd/h-$ZrO_2$ core-shell-shell microspheres increases as the etching time increases. Upon increasing the etching time from 2 to 24 hours, etching of silica shell becomes apparent (FIGS. 27 and 28), and leads to interesting hollow nanostructures, consisting of $SiO_2$/Pd core encapsulated by a moderate-sized hollow and nanoporous $ZrO_2$ shell. Etching the samples for longer etching time of 48 hours, however, resulted in complete dissolution or removal of the inner silica shell, leaving behind a large-sized hollow and nanoporous $ZrO_2$ microsphere with Pd inside. By using an optimal etching time of 24 hours, $SiO_2$/Pd/h-$ZrO_2$ core-shell-shell microspheres having optimum size hollow and nanoporous $ZrO_2$ shells were obtained.

The morphology and the structure of the as-derived $SiO_2$/Pd/h-$ZrO_2$ core-shell-shell microspheres were further examined by field-emission scanning electron microscopy (FESEM) (FIG. 29). From the FESEM images, it can be clearly seen that the particles are spherical in shape and their structures remain intact after removal of their inner $SiO_2$ shell. It can also be noted that a few of the hollow $SiO_2$/Pd/h-$ZrO_2$ microspheres appear to have partially broken shells with visible inner cores (see FIG. 29).

In addition, the $SiO_2$/Pd/h-$ZrO_2$ core-shell-shell microspheres were characterized by $N_2$ gas adsorption. FIG. 30 shows a representative nitrogen adsorption/desorption isotherms for $SiO_2$/Pd/h-$ZrO_2$ core-shell-shell microspheres that were etched for 24 hours, with their corresponding pore size distribution displayed in the inset. The results clearly indicate that the $SiO_2$/Pd/h-$ZrO_2$ core-shell-shell microspheres are nanoporous or have a nanoporous $ZrO_2$ shell. The Brunauer-Emmett-Teller (BET) surface area and single-point total pore volume of the material are 27 $m^2 g^{-1}$ and 0.17 $cm^3 g^{-1}$, respectively. Their average BJH pore diameter calculated from desorption branch of the nitrogen isotherm is ~2.3 nm. This nanoporosity in the sample is clearly due to the pores formed in the $ZrO_2$ shell of $SiO_2$/Pd/h-$ZrO_2$ microspheres from the removal of the Brij surfactant. Furthermore, this nanoporosity is responsible for the permeability of the $ZrO_2$ shell both for the $OH^-$ ions of aqueous NaOH to etch the inner $SiO_2$ shell as well as for the reactants to reach the Pd nanoparticles during catalytic reactions.

The formation of $ZrO_2$ in the $SiO_2$/Pd/h-$ZrO_2$ core-shell-shell microspheres was confirmed by powder X-ray diffraction (XRD) (FIG. 31), which clearly showed the [112] tetragonal phases of $ZrO_2$ (Boobalan et al. (2010) J. Am. Ceram. Soc., 93:3651-3656; Trexlera et al. (2010) J. Mater. Res., 25:500-509). The (111) and (200) Bragg reflections of Pd nanoparticles are also easily observable particularly in the $SiO_2$/Pd core-shell microspheres. The presence of Pd was also further confirmed by ICP-AES, which showed 2.3 wt % Pd in the $SiO_2$/Pd/h-$ZrO_2$ core-shell-shell microspheres that was etched for 24 hours.

Nanocatalysis and Recyclable Catalysis

Hydrogenation was used as a model reaction to explore the catalytic activity of the encapsulated Pd nanoparticles within $SiO_2$/Pd/h-$ZrO_2$ core-shell-shell nanoreactors (Lan et al. (2009) Chem. Eur. J., 15:3670-3673; Deshmukh et al. (2008) Angew. Chem. Int. Ed., 47:8615-8617; Huang et al. (2004) Angew. Chem. Int. Ed., 43:1397-1399). First, a control experiment of hydrogenation reaction of styrene with $SiO_2$/h-$ZrO_2$ core-shell microspheres, which were etched for 24 hours but contained no Pd nanoparticles, was performed. The reaction mixture gave no hydrogenation product in 24 hours reaction time, as expected. However, when the corresponding $SiO_2$/Pd/h-$ZrO_2$ microspheres core-shell-shell microspheres, which contained Pd nanoparticles and were prepared by etching $SiO_2$/Pd/$SiO_2$/h-$ZrO_2$ for 24 hours, were introduced into the reaction mixture, the hydrogenation of styrene proceeded even at room temperature and under 20 bar $H_2$ pressure (Table 7). The reaction, in fact, reached almost completion (~100% conversion of styrene) in 20 minutes at room temperature, giving ethylbenzene as the sole product. The turn-over frequency (TOF), defined as mol of styrene converted per total mole of metal per hour, of the reaction was calculated to be 2,588 $h^{-1}$. This relatively high TOF is indicative of not only the existence of catalytically active Pd nanoparticles, but also the conducive nature of the nanoporous $ZrO_2$ shell for catalysis—allowing reactants to reach the $ZrO_2$ encapsulated Pd nanoparticles and products diffuse out of the hollow nanoreactor.

TABLE 7

Hydrogenation of various substrates by $SiO_2$/Pd/h-ZrO2 core-shell-shell microsphere catalysts.[a]

| Substrate | Product | Time [h] | Conversion [%] | Selectivity [%] | TOF $[h^{-1}]$ [b] |
|---|---|---|---|---|---|
| styrene | ethylbenzene | 0.3 | ~100 | ~100 | 5145 |
| nitrobenzene | aniline | 1.5 | 93 | ~100 | 1187 |
| 1-butylene | butane | 3 | 94 | ~100 | 493 |

[a] Reagents and reaction conditions: 1 mL substrate; methanol: 20 mL; catalyst: 10 mg (5.42 wt. % Pd in the $SiO_2$/Pd/h-$ZrO_2$ core-shell-shell microspheres); reaction temperature: 25° C.; and reactor pressure = 20 bar $H_2$ pressure.
[b] The TOFs were calculated by dividing the total conversion of reactant (or yield of product) in the given time shown in the table with the mole of Pd in the catalyst used, and then normalizing the results for 1 hour reaction time for comparison purposes.

To study the scope of the catalytic activity of the $SiO_2$/Pd/h-$ZrO_2$ core-shell-shell microspheres, attempted hydrogenation reactions of other compounds using the microspheres as catalysts were conducted. Table 7 summarizes the catalytic activities of $SiO_2$/Pd/h-$ZrO_2$ microspheres in the hydrogenation of nitrobenzene and 1-butylene. It is clearly seen that $SiO_2$/Pd/h-$ZrO_2$ microspheres also enabled the catalytic hydrogenation of nitrobenzene and 1-butylene efficiently and almost quantitatively. The corresponding control experiments involving reaction mixtures with $SiO_2$/h-$ZrO_2$ core-shell microspheres again resulted in negligible products. It is particularly interesting to see that the $SiO_2$/Pd/h-$ZrO_2$ core-shell-shell microspheres catalyze the hydrogenation of a relatively hard-to-hydrogenate compound, nitrobenzene, into aniline with 93% yield in 1.5 hour reaction time and at a room temperature (25° C.). Furthermore, the $SiO_2$/Pd/h-$ZrO_2$ core-shell-shell microspheres are proven to be capable of catalyzing the hydrogenation of 1-butylene to butane with 94% conversion in 3 hours.

These results indicate that the new $SiO_2$/Pd/h-$ZrO_2$ core-shell-shell microspheres can be applied for catalytic hydrogenation of a variety of linear unsaturated hydrocarbons as well as functional groups such as nitro groups in organic compounds. Furthermore, in case of hydrogenation of styrene and nitrobenzene, the vinyl and nitro groups, respectively, underwent hydrogenation sectively, without their benzene rings undergoing hydrogenation in the given reaction times.

The recyclability and reusability of the $SiO_2$/Pd/h-$ZrO_2$ microspheres as a heterogeneous catalyst was also investigated. This was performed by recovering the microspheres from a reaction mixture by centrifugation, and reusing them as catalysts in the next reactions (FIG. 32). The recycled microspheres successfully catalyze styrene hydrogenation in up to five cycles without showing major loss of catalytic activity. The small decrease of catalytic activity seems to be the result from the loss of catalyst during the handling and centrifugation of the microspheres. Interestingly, the TEM image (FIG. 33) for the $SiO_2$/Pd/h-$ZrO_2$ core-shell-shell microspheres collected after the fifth successive reaction cycles exhibited no observable change in the structure and morphology of the $SiO_2$/Pd/h-$ZrO_2$ core-shell-shell microspheres.

In addition, ICP-AES showed that there was only very small loss of Pd from $SiO_2$/Pd/h-$ZrO_2$ core-shell-shell microspheres after five reaction cycles. The content of Pd in the solution was also very low; only 460 ppm Pd or 4.32 μmol pd/g was found in the supernatant after the first cycle. These indicate that there was insignificant leaching of Pd from the $SiO_2$/Pd/h-$ZrO_2$ core-shell-shell microspheres into the reaction mixture. Furthermore, a filtration test, involving catalytic reaction of the supernatant after the solid catalyst from is separated from it, indicated that only 5% styrene conversion in 30 minutes took place, whereas ~100% styrene conversion in the presence of the microspheres under the same conditions was obtained. All these results indicate that the amount of Pd leaching from the $SiO_2$/Pd/h-$ZrO_2$ core-shell-shell microspheres is considerably low. As until now all known Pd NP systems are reported to leach, albeit very insignificantly in some cases (Pachon et al. (2008) Appl. Organomet. Chem., 22:288-299; Gaikwad et al. (2007) Chem. Eur. J., 13:6908-6913). Control experiments involving the $SiO_2$/Pd core-shell microspheres, however, showed significant leaching, higher degree of Pd loss and aggregation as well as catalytic activity (Stober et al. (1968) J. Colloid Interface Sci., 26:62-69). It is thus clear that the hollow and nanoporous $ZrO_2$ protected the nanoreactor from losing or leaching its Pd nanoparticles, and helped the material to maintain its robust catalytic activity. Furthermore, the conducive structure of the $SiO_2$/Pd/h-$ZrO_2$ core-shell-shell microspheres including their stable Pd nanoparticles, and their nanoporous $ZrO_2$ shell enabled the encapsulated Pd nanoparticles to perform effective and easily recyclable catalytic activities in hydrogenation reactions of various functional groups. The minor leaching in the core-shell-shell nanospheres may be further reduced by using thicker $ZrO_2$ shells having smaller pore diameters.

In summary, silica microsphere-supported Pd nanoparticles that are encapsulated with a hollow and nanoporous $ZrO_2$ shell were fabricated as yolk-shell catalytic nanoreactors. The hollow and nanoporous $ZrO_2$ shell of these microspheres, dubbed $SiO_2/Pd/h$-$ZrO_2$ microspheres, is permeable enough to allow reactants reach the Pd multicores, while at the same time let the Pd nanoparticles remain intact. The microspheres exhibit excellent catalytic activity and selectivity for the hydrogenation reaction, as shown with hydrogenation of two different olefins and a nitro functional group, at room temperature and under ambient $H_2$ pressure. This effective catalytic activity even at room temperature and moderate pressure was the result of the assembly of $SiO_2$-supported ~5 nm Pd nanoparticle multicores within a hollow and nanoporous $ZrO_2$ shell. Furthermore, the structure enabled the Pd nanoparticles to remain stable without losing their catalytic activities, even after several cycles of catalytic reactions. The protection of the Pd nanoparticles from aggregation/sintering by the nanoporous, hollow $ZrO_2$ shell is particularly interesting considering the fact that the Pd nanoparticles have 'naked' surfaces or no organic surface passivating ligands that are typically needed to stabilize metallic nanoparticles. This, in turn, allowed the Pd nanoparticles to exhibit high catalytic activities by the virtue of their ease of interaction with reactants, as demonstrated here with catalytic hydrogenation reactions. Thus, these materials are recyclable and efficient catalysts that can be used in catalytic hydrogenation of various substrates at room temperature and under moderate pressure.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A catalytic nanoparticle comprising a silica core covalently attached to at least one dendrimer encompassing at least one metal catalyst, wherein said silica core is etched.

2. The catalytic nanoparticle of claim 1, wherein said dendrimer is an amine-terminated poly(amido amine) (PAMAM) dendrimer.

3. The catalytic nanoparticle of claim 1, wherein said dendrimer is covalently attached to said silica core via a linker.

4. The catalytic nanoparticle of claim 1, wherein said metal catalyst is selected from the group consisting of platinum, ruthenium, iron, cobalt, gold, chromium, molybdenum, tungsten, manganese, technetium, rhenium, osmium, rhodium, iridium, nickel, palladium, copper, silver, zinc, tin, aluminum, and combinations thereof.

5. The catalytic nanoparticle of claim 4, wherein said metal catalyst is palladium.

6. The catalytic nanoparticle of claim 1, wherein said dendrimer is a poly(amidoamine) (PAMAM) dendrimer or a polypropyleneimine (PPI) dendrimers.

7. The catalytic nanoparticle of claim 3, wherein said linker is an alkyl, carbonyl, or an optionally substituted aryl group.

8. The catalytic nanoparticle of claim 1, wherein said metal catalyst is a nanoparticle of metal.

9. A method of synthesizing the catalytic nanoparticle of claim 1 comprising:
   a) etching silica core,
   b) covalently attaching at least one dendrimer to the etched silica core, and
   c) entrapping at least one metal catalyst in said dendrimer, thereby creating said catalytic nanoparticle.

10. A method of catalyzing a chemical reaction, said method comprising adding at least one catalytic nanoparticle of claim 1 to said chemical reaction.

11. The method of claim 10, wherein said chemical reaction is a hydrogenation reaction or a Heck coupling reaction.

12. A catalytic nanoparticle comprising a silica core attached to at least one metal catalyst and an etched silica outer layer, wherein said metal catalyst is a nanoparticle of metal, wherein said metal in said metal catalyst is selected from the group consisting of platinum, ruthenium, iron, cobalt, chromium, molybdenum, tungsten, manganese, technetium, rhenium, osmium, rhodium, iridium, nickel, palladium, copper, silver, zinc, tin, aluminum, and combinations thereof.

13. The catalytic nanoparticle of claim 12, wherein said metal is palladium.

14. A method of synthesizing the catalytic nanoparticle of claim 12 comprising:
   a) attaching at least one metal catalyst on a silica core,
   b) adding a silica outer layer onto the metal catalyst coated silica core, and
   c) etching the silica outer layer, thereby generating the catalytic nanoparticle.

15. A method of catalyzing a chemical reaction, said method comprising adding at least one catalytic nanoparticle of claim 12 to said chemical reaction.

16. The method of claim 15, wherein said chemical reaction is a hydrogenation reaction or a Heck coupling reaction.

17. A catalytic nanoparticle comprising a silica core coated with at least one metal catalyst, and a hollow, nanoporous shell, wherein said hollow, nanoporous shell comprises a metal oxide, wherein said hollow, nanoporous shell encapsulates the metal catalyst coated silica core, and wherein said metal catalyst is a nanoparticle of metal.

18. The catalytic nanoparticle of claim 17, wherein said metal in said metal catalyst is selected from the group consisting of platinum, ruthenium, iron, cobalt, gold, chromium, molybdenum, tungsten, manganese, technetium, rhenium, osmium, rhodium, iridium, nickel, palladium, copper, silver, zinc, tin, aluminum, and combinations thereof.

19. The catalytic nanoparticle of claim 18, wherein said metal is palladium.

20. The catalytic nanoparticle of claim 17, wherein said hollow, nanoporous shell comprises zirconium oxide.

21. The catalytic nanoparticle of claim 17, wherein said metal oxide is selected from the group consisting of nickel, cobalt, manganese, titanium, vanadium, zirconium, iron, cerium, zinc, and aluminum oxides.

22. The catalytic nanoparticle of claim 17, wherein said hollow, nanoporous shell consists of zirconium oxide.

23. A method of synthesizing the catalytic nanoparticle of claim 17 comprising:
   a) coating at least one metal catalyst on a silica core,
   b) adding a silica shell onto the metal catalyst coated silica core,
   c) coating the silica shell with a porous metal oxide, and
   d) removing the silica shell, thereby generating a hollow, nanoporous shell and an accessible catalytic nanoparticle.

24. A method of catalyzing a chemical reaction, said method comprising adding at least one catalytic nanoparticle of claim 17 to said chemical reaction.

25. The method of claim 24, wherein said chemical reaction is a hydrogenation reaction or a Heck coupling reaction.

* * * * *